(12) United States Patent
Egawa et al.

(10) Patent No.: US 6,800,629 B2
(45) Date of Patent: Oct. 5, 2004

(54) PYRAZINE DERIVATIVES OR SALTS THEREOF, PHARMACEUTICAL COMPOSITION CONTAINING THE SAME, AND PRODUCTION INTERMEDIATES THEREOF

(75) Inventors: Hiroyuki Egawa, Toyama (JP); Yousuke Furuta, Toyama (JP); Jun Sugita, Nyuzen-machi (JP)

(73) Assignee: Toyama Chemical Co., Ltd., Tokyo (JP)

( * ) Notice: Subject to any disclaimer, the term of this patent is extended or adjusted under 35 U.S.C. 154(b) by 83 days.

(21) Appl. No.: 10/219,294

(22) Filed: Aug. 16, 2002

(65) Prior Publication Data

US 2003/0130213 A1 Jul. 10, 2003

Related U.S. Application Data

(63) Continuation of application No. PCT/JP01/01038, filed on Feb. 14, 2001.

(30) Foreign Application Priority Data

Feb. 16, 2000 (JP) ........................................ 2000-037486
Feb. 18, 2000 (JP) ........................................ 2000-040439
Mar. 29, 2000 (JP) ........................................ 2000-090071

(51) Int. Cl.[7] .................. C07D 405/04; C07D 241/20; A61K 31/497; A61K 31/4965; A61P 31/12
(52) U.S. Cl. .................. 514/255.05; 544/337; 544/406; 544/409; 514/255.06
(58) Field of Search ................................ 544/406, 337; 514/255.05, 255.06

(56) References Cited

U.S. PATENT DOCUMENTS 5,562,859 A * 10/1996 Schlosser et al. ...... 252/299.61

FOREIGN PATENT DOCUMENTS

WO    WO 00/10569    2/2000

OTHER PUBLICATIONS

J. Davis, et al., "Synthesis and Antiviral Evaluation of Pyrazinones Substituted with Acyclic Chains", Nucleosides & Nucleotides, 17(5), pp. 875–893 (1998).

* cited by examiner

Primary Examiner—Mark L. Berch
Assistant Examiner—Kahsay Habte
(74) Attorney, Agent, or Firm—Oblon, Spivak, McClelland, Maier & Neustadt, P.C.

(57) ABSTRACT

Pyrazine derivatives represented by general formula [1]:

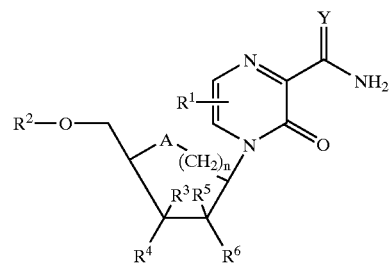

[1]

wherein the variables are as defined in the specification, or salts thereof have an excellent antiviral activity and are useful as a therapeutic agent for treating viral infections. Further, fluoropyrazine-carboxamide derivatives represented by general formula [2]:

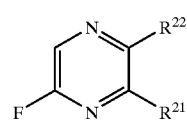

[2]

wherein the variables are as defined in the specification, or salts thereof are useful as an intermediate for production of the compounds of general formula [1], and as an intermediate for production of the fluoropyrazine-carboxamide derivatives of which one typical example is 6-fluoro-3-hyroxy-2-pyrazine-carboxamide having an antiviral activity.

9 Claims, No Drawings

PYRAZINE DERIVATIVES OR SALTS THEREOF, PHARMACEUTICAL COMPOSITION CONTAINING THE SAME, AND PRODUCTION INTERMEDIATES THEREOF

This case is a continuation of PCT/JP01/01038 filed on Feb. 14, 2001.

TECHNICAL FIELD

The present invention relates to novel pyrazine derivatives or salts thereof, a pharmaceutical composition containing the same, and production intermediates thereof.

BACKGROUND ART

As the antiviral agents clinically used today, acyclovir and vidarabine for controlling herpesvirus, ganciclovir and foscarnet for controlling cytomegalovirus, and interferon, etc. for controlling hepatitis virus can be referred to. Further, prevention by the use of vaccine is extensively adopted against influenza virus, and low molecular compounds such as amantadine hydrochloride and ribavirin are also used for this purpose. Further, zanamivir is also used lately.

On the other hand, as to the antiviral activity of nucleoside- and nucleotide-analogues having a pyrazine ring as a base, for example, it has hitherto been reported that the compounds of the following general formula:

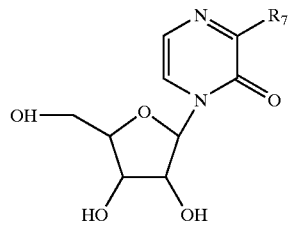

wherein $R^7$ represents hydrogen atom, methyl group or $C_{10}H_{21}$, have an antiviral activity. However, this type compounds show no "Visna virus activity" [Nucleosides & Nucleotides, Vol. 15, Nos. 11 and 12, Pages 1849–1861 (1996)]. Further, nucleoside- and nucleotide-analogues having a pyrazine ring substituted with a carbamoyl group have not yet been reported so far.

As problems of amantadine, that it is not effective against B type influenza even though it is effective against A type influenza, because of its action mechanism, that its resistance virus can appear, that it causes a nerve disturbance, etc. have been mentioned. On the other hand, although ribavirin shows a polymerase-inhibitory activity and effective against A type and B type influenza, it exhibits no sufficient clinical effect when used orally.

Thus, it has been desired to develop an antiviral agent having an infection-preventive effect against various viruses and especially against influenza virus and exhibiting a therapeutic effect.

In PCT/JP99/04429 (WO00/10569), there are mentioned nitrogen-containing heterocyclic carbamoyl derivatives represented by the following general formula [22]:

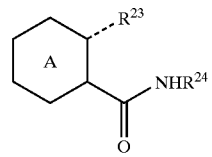

[22]

wherein ring A represents a substituted or unsubstituted pyrazine, pyrimidine, pyridazine or triazine ring, $R^{23}$ represents O or OH, $R^{24}$ represents hydrogen atom, acyl group or carbamoylalkyl group, and the broken line represents a single bond or a double bond, and salts thereof, which are useful as an antiviral agent. Although mention is made in the patent application of the process for producing the compounds represented by general formula [22] and the intermediates used for the production, there is no description in the above-mentioned patent application about usefulness of the fluoropyrazine derivatives of the present patent application as a production intermediate for the compounds represented by general formula [22]. It is described there that, among the compounds of general formula [22], those in which the substituent of the pyrazine ring is a fluorine atom, namely the compounds represented by the following general formula [23]:

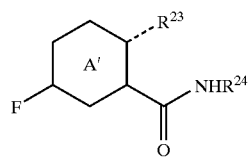

[23]

wherein ring A' is a pyrazine ring, and $R^{23}$, $R^{24}$ and the broken line have the same meanings as above, have a strong anti-influenza virus activity and are excellent as an antiviral agent.

DISCLOSURE OF THE INVENTION

With the aim of solving the problems mentioned above, the present inventors have conducted extensive studies. As a result, it has been found that a pyrazine derivative represented by the following general formula [1]:

[1]

wherein $R^1$ represents a hydrogen atom or a halogen atom; $R^2$ represents a hydrogen atom or a protected or unprotected monophosphoric, diphosphoric or triphosphoric acid group; $R^3$, $R^4$, $R^5$ and $R^6$ which may be the same or different represent a hydrogen atom, a halogen atom, an azido group, a substituted or unsubstituted, protected or unprotected hydroxyl or amino group or $R^4$ and $R^6$, taken conjointly, represent a bonding unit; A represents an oxygen atom or a methylene group; n represents 0 or 1; and Y represents an oxygen atom, a sulfur atom or an NH group, or a salt thereof has an excellent antiviral activity. Based on this finding, the present invention has been accomplished.

Further, it has also been found that a fluoropyrazine derivative represented by the following general formula [21]:

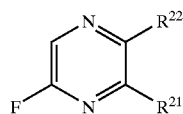

[21]

wherein $R^{21}$ represents a hydrogen atom, a methyl group, a halogenated methyl group, a methyl group substituted with a protected or unprotected mercapto group, a formyl group, a nitrile group, a halogenated carbonyl group or a protected or unprotected hydroxymethyl, aminomethyl, carbamoyl or carboxyl group; $R^{22}$ represents a hydrogen atom, a halogen atom, a protected or unprotected hydroxyl or amino group, a nitro group, an azido group or a substituted or unsubstituted phenylsulfanyl, phenylsulfinyl or phenylsulfonyl group; provided that a case that $R^{21}$ is a carbamoyl group or a carbamoyl group substituted with an acyl group and $R^{22}$ is a hydroxyl group and a case that $R^{21}$ is a hydrogen atom and $R^{22}$ is a hydrogen atom are excepted, or a salt thereof is an excellent intermediate for the industrial production of the fluoropyrazine-carboxamide derivative which is an intermediate for production of the compound represented by general formula [1] in which $R^1$ is a fluorine atom. Based on this finding, the present invention has been accomplished.

Further, it has also been found that the fluoropyrazine derivative represented by general formula [21] or a salt thereof is an excellent intermediate for the industrial production of the fluoropyrazine-carboxamide derivative represented by general formula [23] having an antiviral activity. Based on these findings, the present invention has been accomplished.

Hereunder, the present invention will be detailed.

As used in this specification, meanings of the following terms are as follows, unless otherwise defined. The term "halogen atom" means a fluorine atom, a chlorine atom, a bromine atom or an iodine atom; "halogenated methyl group" means a mono-, di- or tri-substituted halogenated methyl group such as fluoromethyl, chloromethyl, bromomethyl, iodomethyl, dichloromethyl, trifluoromethyl, trichloromethyl and the like; "halogenated carbonyl group" means a fluorocarbonyl, chlorocarbonyl, bromocarbonyl or iodocarbonyl group; "lower alkyl group" means a $C_{1-5}$ alkyl group such as methyl, ethyl, n-propyl, isopropyl, n-butyl, isobutyl, sec-butyl, tert-butyl, pentyl and the like; "lower alkoxy group" means a $C_{1-5}$ alkoxy group such as methoxy, ethoxy, n-propoxy, isopropoxy, n-butoxy, isobutoxy, sec-butoxy, tert-butoxy, pentyloxy and the like; "lower alkoxycarbonyl group" means a $C_{1-5}$ alkoxycarbonyl group such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl and the like; "lower alkylamino group" means a mono- or di-$C_{1-5}$ alkylamino group such as methylamino, ethylamino, propylamino, dimethylamino, diethylamino, methylethylamino and the like; "halogeno-lower alkyl group" means a halogeno-$C_{1-5}$ alkyl group such as fluoromethyl, chloromethyl, bromomethyl, dichloromethyl, trifluoromethyl, trichloromethyl, chloroethyl, dichloroethyl, trichloroethyl, chloropropyl and the like; "lower alkenyl group" means a $C_{2-5}$ alkenyl group such as vinyl, allyl and the like; "cycloalkyl group" means a $C_{3-6}$ cycloalkyl group such as cyclopropyl, cyclobutyl, cyclopentyl, cyclohexyl and the like; "aryl group" means a phenyl group, a naphthyl group or the like; and "heterocyclic group" means a 4- to 6-membered or fused heterocyclic group containing at least one hetero atom selected from oxygen atom, nitrogen atom and sulfur atom, such as azetidinyl, thienyl, furyl, pyrrolyl, imidazolyl, pyrazolyl, thiazolyl, isothiazolyl, oxazolyl, isoxazolyl, furazanyl, pyrrolidinyl, pyrrolinyl, imidazolidinyl, imidazolinyl, pyrazolidinyl, pyrazolinyl, 1,3,4-oxadiazolyl, 1,2,3-thiadiazolyl, 1,2,4-thiadiazolyl, 1,3,4-thiadiazolyl, 1,2,3-triazolyl, 1,2,4-triazolyl, thiatriazolyl, pyridyl, pyrazinyl, pyrimidinyl, pyridazinyl, pyranyl, morpholinyl, 1,2,4-triazinyl, benzothienyl, naphthothienyl, benzofuryl, isobenzofuryl, chromenyl, indolizinyl, isoindolyl, indolyl, indazolyl, purinyl, quinolyl, isoquinolyl, phthalazinyl, naphthylidinyl, quinoxalinyl, quinazolinyl, cinnolinyl, phthalidinyl, isochromanyl, chromanyl, indolinyl, isoindolinyl, benzoxazolyl, triazolopyridyl, tetrazolopyridazinyl, tetrazolopyrimidinyl, thiazolopyridazinyl, thiadiazolopyridazinyl, triazolopyridazinyl, benzimidazolyl, benzthiazolyl, 1,2,3,4-tetrahydroquinolyl, imidazo[1,2-b][1,2,4]-triazinyl, quinuclidinyl and the like.

In cases where the compound of the present invention and production intermediate thereof have a hydroxyl group, a mercapto group, an amino group, a carbamoyl group or a carboxyl group, those substituents may be protected with known protecting groups.

The terms "monophosphoric acid group", "diphosphoric acid group" and "triphosphoric acid group" mean groups of the following general formula:

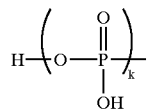

wherein k is 1, 2 and 3, respectively.

As protecting groups for the monophosphoric acid group, diphosphoric acid group and triphosphoric acid group, all the groups conventionally usable for protection of phosphoric acid groups can be referred to. Examples thereof include lower alkyl groups such as methyl, cyclopropylmethyl, tert-butyl, ethan-1,2-diyl and the like; halogeno lower alkyl groups such as 2,2,2-trichlorethyl, 2,2,2-trichloro-1,1-dimethylethyl, 2,2,2-tribromethyland the like; acyl lower alkyl groups such as 1-acetylethyl and the like; cyano lower alkyl groups such as 2-cyanoethyl and the like; lower alkylsulfonyl lower alkyl groups such as 2-methylsulfonylethyl and the like; arylsulfonyl lower alkyl groups such as 2-phenylsulfonylethyl and the like; alkenyl groups such as allyl and the like; aryl groups such as phenyl, o-hydroxyphenyl, o-chlorophenyl, p-chlorophenyl, 2,4-dichlorophenyl, p-nitrophenyl, 2-dimethylamino-4-nitrophenyl, 2-tert-butylphenyl, 2-chloromethyl-4-nitrophenyl, o-phenylene and the like; ar-lower alkyl groups such as benzyl, o-nitrobenzyl, p-nitrophenylethyl and the like; heterocyclic groups such as 8-quinolyl, 5-chloro-8-quinolyl and the like; etc. One or more kinds of the above-mentioned protecting groups may be used for the protection.

As protecting groups for carboxyl group, all the groups conventionally usable for protection of carboxyl group can be referred to. Examples thereof include lower alkyl groups such as methyl, ethyl, n-propyl, isopropyl, 1,1- dimethylpropyl, n-butyl, tert-butyl and the like; aryl groups such as phenyl, naphthyl and the like; ar-lower alkyl groups such as benzyl, diphenylmethyl, trityl, p-nitrobenzyl, p-methoxybenzyl, bis(p-methoxyphenyl)-methyl and the like; acyl-lower alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-lower alkyl groups such as 2,2,2-trichlorethyl and the like; lower alkyl-silyl-alkyl groups such as 2-(trimethylsilyl)ethyl and the like; acyloxyalkyl groups such as acetoxymethyl, propionyloxymethyl, pivaloyloxymethyl and the like; nitrogen-containing heterocycle-lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethylsilyl)ethoxymethyl and the like; ar-lower alkoxy-lower alkyl groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butynyl, allyl and the like; and lower alkyl-substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

As protecting groups for amino and lower alkylamino groups, all the groups conventionally usable for protection of amino groups can be referred to. Examples thereof include acyl groups such as trichloroethoxycarbonyl, tribromoethoxycarbonyl, benzyloxycarbonyl, p-nitrobenzyloxycarbonyl, o-bromobenzyloxycarbonyl, (mono-, di- and tri-) chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; ar-lower alkyl groups such as benzyl, diphenylmethyl, trityl and the like; arylthio groups such as 2-nitrophenylthio, 2,4-dinitrophenylthio and the like; alkane- or allene-sulfonyl groups such as methanesulfonyl, p-toluenesulfonyl and the like; di-lower alkylamino-lower alkylidene groups such as N,N-dimethylaminomethylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; di-aryl or di-ar-lower alkyl phosphoryl groups such as diphenyl phosphoryl, dibenzyl phosphoryl and the like; oxygen-containing heterocyclic alkyl groups such as 5-methyl-2-oxo-2H-1,3-dioxol-4-ylmethyl and the like; and lower alkyl-substituted silyl groups such as trimethylsilyl group and the like.

As protecting group for hydroxyl group and mercapto group, all the groups conventionally usable for protection of hydroxyl groups can be referred to. Examples thereof include acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichlorethoxycarbonyl, 2,2,2-tribromethoxycarbonyl, 2-(trimethylsilyl)ethoxycarbonyl, 2-(phenylsulfonyl)-ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichlorethyl, 2-trimethylsilylethyl and the like; lower alkenyl groups such as allyl and the like; ar-lower alkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; lower alkoxy- and lower alkylthio-lower alkyl groups such as methoxymethyl, methylthiomethyl, benzyloxymethyl, 2-methoxyethoxymethyl, 2,2,2-trichlorethoxymethyl, 2-(trimethylsilyl)ethoxymethyl, 1-ethoxyethyl and the like; alkane- or allene-sulfonyl groups such as methanesulfonyl, p-toluenesulfonyl and the like; substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like; substituted aryl groups such as hydroquinone, p-methoxyphenol and the like; enol-ether groups such as (2-methyl-3-oxo-1-cyclopenten-1-yl) and the like.

As protecting groups for carbamoyl group, all the groups conventionally usable for protection of carbamoyl group can be referred to. Examples thereof include ar-lower alkyl groups such as benzyl, 4-methoxybenzyl, 2,4-dimethoxybenzyl and the like; lower alkoxyalkyl groups such as methoxymethyl and the like; ar-lower alkoxy groups such as benzyloxymethyl and the like; substituted silyl lower alkoxy-lower alkyl groups such as tert-butyldimethylsiloxymethyl and the like; lower alkoxy groups such as methoxy and the like; ar-lower alkoxy groups such as benzyloxy and the like; lower alkylthio groups such as methylthio, triphenylmethylthio and the like; ar-lower alkylthio groups such as benzylthio and the like; substituted silyl groups such as tert-butyldimethylsilyl and the like; aryl groups such as 4-methoxyphenyl, 4-methoxymethylphenyl, 2-methoxy-1-naphthyl and the like; acyl groups such as trichloroethoxycarbonyl, trifluoroacetyl, tert-butoxycarbonyl and the like; etc.

As the substituent for the hydroxyl group represented by $R^3$, $R^4$, $R^5$, $R^6$, $Z^2$, $Z^3$, $Z^4$ and $Z^5$ which may be substituted, a protected or unprotected carboxyl group, a lower alkyl group, a lower alkoxycarbonyl group, an aryl group, a cycloalkyl group, a lower alkenyl group, a halogeno-lower alkyl group and a heterocyclic group can be referred to. One or more kinds selected from these substituents may be used for the substitution.

As the substituent for the amino group represented by $R^3$, $R^4$, $R^5$, $R^6$, $Z^2$, $Z^3$, $Z^4$ and $Z^5$ which may be substituted, a protected or unprotected carboxyl, hydroxyl, amino and lower alkylamino groups, a lower alkyl group, a lower alkoxy group, a lower alkoxycarbonyl group, an aryl group, a cycloalkyl group, a lower alkenyl group, a halogeno-lower alkyl group and a heterocyclic group can be referred to. One or more substituents selected from the above-mentioned groups may be used for the substitution.

As the substituent for the phenylsulfanyl group, phenylsulfinyl group and phenylsulfonyl group represented by $R^{22}$, lower alkyl groups such as methyl, ethyl and the like can be referred to.

As the salts of the compounds of general formulas [1] and [21], usually known salts at the site of basic group such as amino group, etc. and salts at the site of acidic group such as hydroxyl group, phosphoryl group, carboxyl group, etc. can be referred to. The salts at the site of basic group include, for example, salts with a mineral acid such as hydrochloric acid, hydrobromic acid, sulfuric acid and the like; salts with an organic acid such as tartaric acid, formic acid, citric acid, trichloroacetic acid, trifluoroacetic acid and the like; and salts with a sulfonic acid such as methanesulfonic acid, benzenesulfonic acid, p-toluenesulfonic acid, mesitylenesulfonic acid, naphthalenesulfonic acid and the like. The salts at the site of acidic group include salts with an alkali metal such as sodium, potassium and the like; salts with an alkaline earth metal such as calcium, magnesium and the like; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like.

Of the salts mentioned above, preferred are pharmacologically acceptable ones.

In some cases, the compounds of general formulas [1] and [21] and salts thereof have isomers such as optical isomers, geometrical isomers and tautomers. In such cases, the present invention involves those isomers, and further involves solvated products, hydrates and various crystalline forms, too.

Of the pharmaceutical compositions of the present invention, preferable pharmaceutical compositions are antiviral agents, and further preferable antiviral compositions are antiviral agents for controlling influenza virus, RS virus, AIDS virus, papilloma virus, adenovirus, hepatitis virus A, hepatitis virus B, hepatitis virus C, poliovirus, echo virus, coxsackie virus, enterovirus, rhinovirus, rotavirus, newcastle disease virus, mumps virus, vesicular stomatitis virus, and Japanese encephalitis virus. As yet further preferable antiviral agents, those against rotavirus, RS virus and influenza virus can be referred to. As yet more preferable one, the antiviral agent against influenza virus can be referred to.

Of the compounds of the present invention, preferable compounds are those in which $R^3$, $R^4$, $R^5$ and $R^6$ which may be the same or different represent a hydrogen atom, a halogen atom or a substituted or unsubstituted, protected or unprotected hydroxyl group or $R^4$ and $R^6$ are taken conjointly to form a bonding unit, and salts of such compounds; and further preferable compounds are those in which $R^2$ is a hydrogen atom or a protected or unprotected monophosphoric acid group or tri-phosphoric acid group; and yet further preferable compounds are those in which $R^2$ is a hydrogen atom or a protected or unprotected monophosphoric acid group, $R^3$, $R^4$, $R^5$ and $R^6$ which may be the same and different represent a hydrogen atom or a protected or unprotected hydroxyl group, A is an oxygen atom, and n is 0, and salts thereof; and further more preferable compounds are those in which $R^2$ is a hydrogen atom, and salts thereof.

As yet more preferable compounds, compounds in which $R^1$ is a hydrogen atom, a chlorine atom or a fluorine atom, or salts thereof can be referred to; and as further preferable compounds, those in which $R^1$ is a hydrogen atom or a fluorine atom, and salts thereof can be referred to.

Of the intermediate compounds of the present invention, preferable are those in which $R^{21}$ is a hydrogen atom, a methyl group, a halogenated methyl group, a formyl group, a nitrile group, a halogenated carbonyl group or a protected or unprotected hydroxymethyl, carbamoyl or carboxyl group, and salts thereof; and further preferable are those in which $R^{22}$ is a protected or unprotected hydroxyl or amino group, a halogen atom, a nitro group or an azido group, and salts thereof; and yet further preferable are those in which $R^{21}$ is a methyl group, a halogenated methyl group, a formyl group, a carbamoyl group, a nitrile group, a halogenated carbonyl group or a protected or unprotected hydroxylmethyl or carboxyl group, and salts thereof; and more preferable are those in which $R^{21}$ is a halogenated methyl group, a formyl group, a carbamoyl group, a nitrile group, a halogenated carbonyl group or a protected or unprotected hydroxymethyl or carboxyl group, and salts thereof; and further more preferable are those in which $R^{21}$ is a carbamoyl group, a protected or unprotected carboxyl group, a nitrile group or a halogenated carbonyl group, and salts thereof. Among the compounds mentioned above, however, those in which $R^{21}$ is a carbamoyl group or a carbamoyl group substituted with an acyl group and $R^{22}$ is a hydroxyl group and those in which $R^{21}$ is a hydrogen atom and $R^{22}$ is a hydrogen atom are excepted.

Among the compounds of the present invention, typical are, for example, those shown in Table I-1, wherein "Bn" represents a benzyl group and "–" represents a bonding unit.

TABLE I-1

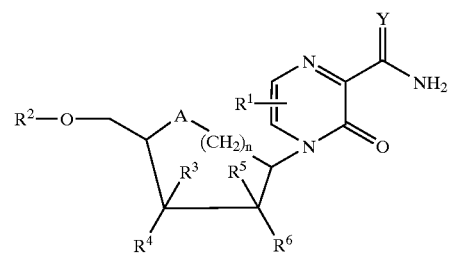

| $R^1$ | $R^2$ | $R^3$ | $R^4$ | $R^5$ | $R^6$ | A | n | Y |
|---|---|---|---|---|---|---|---|---|
| H | H | H | OH | H | OH | O | 0 | O |
| H | H | H | OH | H | OH | O | 0 | NH |

TABLE I-1-continued

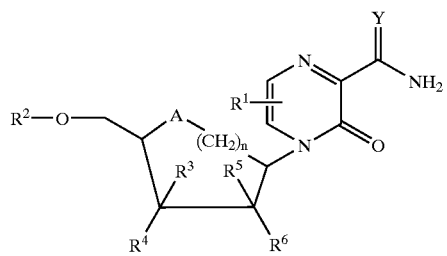

| R¹ | R² | R³ | R⁴ | R⁵ | R⁶ | A | n | Y |
|---|---|---|---|---|---|---|---|---|
| H | H | H | OH | H | OH | O | 0 | S |
| 6-F | H | H | OH | H | OH | O | 0 | O |
| 6-F | H | H | OH | H | OH | O | 0 | NH |
| 6-Cl | H | H | OH | H | OH | O | 0 | O |
| 6-F | H | H | OH | H | H | O | 0 | O |
| H | H | H | OH | H | H | O | 0 | O |
| H | H | H | OH | H | F | O | 0 | O |
| 6-F | H | H | OH | H | NH₂ | O | 0 | O |
| 6-F | H | H | NH₂ | H | OH | O | 0 | O |
| 6-F | H | H | OH | OH | H | O | 0 | O |
| H | H | H | OH | H | NH₂ | O | 0 | O |
| H | H | H | NH₂ | H | OH | O | 0 | O |
| H | H | H | OH | OH | H | O | 0 | O |
| H | H | H | OH | F | H | O | 0 | O |
| H | H | H | OH | N₃ | H | O | 0 | O |
| 6-F | H | H | N₃ | H | H | O | 0 | O |
| 6-F | H | H | H | H | H | O | 0 | O |
| 6-F | (HO)₂PO | H | OH | H | OH | O | 0 | O |
| H | H | H | N₃ | H | H | O | 0 | O |
| H | H | H | H | H | H | O | 0 | O |
| H | (HO)₂PO | H | OH | H | OH | O | 0 | O |
| H | (BnO)₂PO | H | OH | H | OH | O | 0 | O |
| 6-F | H | H | OH | H | OH | CH₂ | 0 | O |
| H | H | H | OH | H | OH | CH₂ | 0 | O |
| H | H | H | OH | OH | H | CH₂ | 0 | O |
| H | H | H | H | H | H | CH₂ | 0 | O |
| H | H | H | — | H | — | CH₂ | 0 | O |
| H | H | H | OH | H | H | O | 1 | O |
| H | H | H | OH | H | OH | O | 1 | O |
| 6-F | H[OP(O)OH]₃ | H | OH | H | OH | O | 0 | O |
| H | H[OP(O)OH]₃ | H | OH | H | OH | O | 0 | O |
| 6-F | [CH₂=CHCH₂O]P(O) | H | OH | H | OH | O | 0 | O |
| H | [CH₂=CHCH₂O]P(O) | H | OH | H | OH | O | 0 | O |

Typical intermediates for the compounds of the present invention are shown in the following Table II-1 to 5, wherein "Et" represents an ethyl group, "Ac" represents an acetyl group, "Ph" represents a phenyl group, "Bz" represents a benzoyl group, "tBu" represents a tert-butyl group, "OPh (p-OH)" represents a parahydroxyphenyloxy group, and "$C_6H_7O$" represents a 2-methyl-3-oxo-1-cyclopenten-1-yl group.

TABLE II-1

| R²¹ | R²² |
|---|---|
| H | OCH₃ |
| H | NH₂ |
| CH₃ | H |
| CH₃ | OH |
| CH₃ | OCH₃ |
| CH₃ | NH₂ |
| CH₃ | F |
| CH₂OH | H |
| CH₂OH | OH |
| CH₂OH | OCH₃ |
| CH₂OH | NH₂ |
| CH₂OH | F |
| CH₂Cl | H |
| CH₂Cl | OH |
| CH₂Cl | OCH₃ |
| CH₂Cl | NH₂ |
| CH₂Cl | F |
| CH₂Br | H |
| CH₂Br | OH |
| CH₂Br | NH₂ |

TABLE II-2

| R²¹ | R²² |
|---|---|
| CHO | H |
| CHO | OH |
| CHO | OCH₃ |
| CHO | NH₂ |
| CHO | F |
| CONH₂ | H |
| CONH₂ | OCH₃ |
| CONH₂ | NH₂ |
| CONH₂ | Cl |

TABLE II-2-continued

| R²¹ | R²² |
|---|---|
| CONH₂ | F |
| CONH₂ | NO₂ |
| CONH₂ | N₃ |
| COOH | H |
| COOH | OH |
| COOH | OCH₃ |
| COOH | NH₂ |
| COOH | F |
| COOH | NO₂ |
| COOH | N₃ |

TABLE II-3

| R²¹ | R²² |
|---|---|
| COOCH₃ | H |
| COOCH₃ | OH |
| COOCH₃ | OCH₃ |
| CQOCH₃ | NH₂ |
| COOCH₃ | F |
| COOCH₃ | NO₂ |
| COOEt | H |
| COOEt | OH |
| COOEt | OCH₃ |
| CN | H |
| CN | OH |
| CN | OCH₃ |
| CN | NH₂ |
| CN | F |
| CN | NO₂ |
| CN | N₃ |
| CN | OCH₂Ph |
| CN | OCH₂CH=CH₂ |
| CN | OPh(p-OH) |
| CN | SPh |
| CN | SOPh |
| CN | SO₂Ph |
| CN | OSO₂CH₃ |
| CN | OC₆H₇O |
| COCl | OH |
| COCl | OCH₃ |
| COCl | NH₂ |
| COCl | F |
| COF | OCH₃ |
| COF | NH₂ |
| COF | F |

TABLE II-4

| R²¹ | R²² |
|---|---|
| CONHAc | H |
| CONHAc | OCH₃ |
| CONHAc | NH₂ |
| CONHAc | Cl |
| CONHAc | F |
| CONHAc | NO₂ |
| CONHAc | N₃ |
| CONHBz | OCH₃ |
| CONHBz | NH₂ |
| CONHBz | Cl |
| CONHBz | F |
| CONHBz | NO₂ |
| CONHBz | N₃ |
| CONHC(O)tBu | OCH₃ |
| CONHC(O)tBu | NH₂ |
| CONHC(O)tBu | Cl |
| CONHC(O)tBu | F |
| CONHC(O)tBu | NO₂ |
| CONHC(O)tBu | N₃ |

TABLE II-5

| R²¹ | R²² |
|---|---|
| CONHCH₂Ph | OCH₃ |
| CONHCH₂Ph | NH₂ |
| CONHCH₂Ph | Cl |
| CONHCH₂Ph | F |
| CONHCH₂Ph | NO₂ |
| CONHCH₂Ph | N₃ |
| CONHCH₂OCH₂Ph | OCH₃ |
| CONHCH₂OCH₂Ph | NH₂ |
| CONHCH₂OCH₂Ph | Cl |
| CONHCH₂OCH₂Ph | F |
| CONHCH₂OCH₂Ph | NO₂ |
| CONHCH₂OCH₂Ph | N₃ |

Next, production process of the compounds of the present invention are described below.

The compounds of the present invention can be produced according to the routes of Production Process I-1 to 4 shown below.

[Production Process I-1]

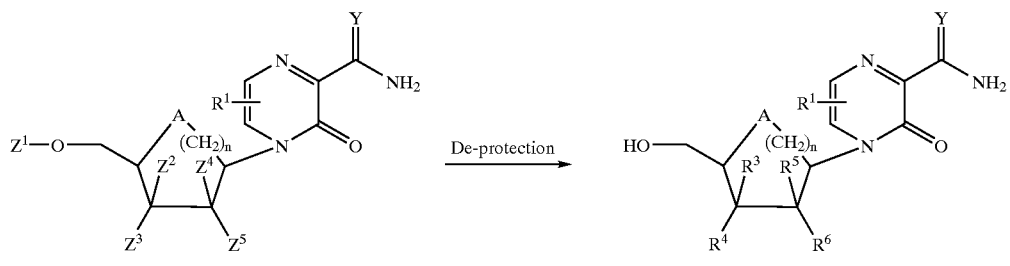

-continued

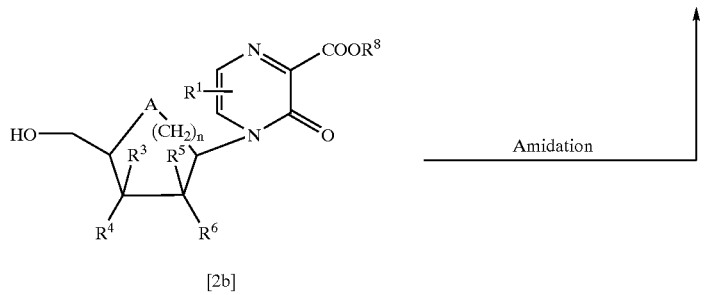

[2b]

Amidation wherein $R^1$, $R^3$, $R^4$, $R^5$, $R^6$, A, Y and n are as defined above; $R^8$ represents a lower alkyl group; $Z^1$ represents a hydrogen atom or a protecting group for hydroxyl group; $Z^2$, $Z^3$, $Z^4$ and $Z^5$ which may be the same or different represent a hydrogen atom, a halogen atom, an azido group, a protected hydroxy group or an amino group; or $Z^3$ and $Z^5$ may be taken conjointly to form a bonding unit.

(a) The compound of general formula [1a] or a salt thereof can be obtained by subjecting a compound of general formula [2a] or salt thereof to a de-protecting reaction.

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylacetamide and the like; alcohols such as methanol, ethanol, propanol and the like; sulfoxides such as dimethyl sulfoxide and the like; water, etc. These solvents may be used alone or as a mixture of two or more.

As the de-protecting agent, agents generally used for de-protection of hydroxyl group, amino group and phosphoric acid group may be used. Preferably, however, bases such as sodium methoxide, hydrogen gas, ammonia gas, aqueous ammonia, butylamine and the like; acids such as formic acid, aqueous acetic acid, aqueous trifluoroacetic acid, hydrochloric acid and the like; palladium catalysts such as tetrakis-triphenylphosphine palladium (O) and the like; and phosphines such as triphenylphosphine and the like are used. These de-protecting agents may be used in combination, or may be produced in the reaction system. The de-protecting agent is used in an amount of at least 0.01 mol per mol of the compound of general formula [2a] or salt thereof. If desired, it is also possible to use the de-protecting agent as a solvent.

The de-protecting reaction is carried out usually at a temperature of –50° C. to 170° C. and preferably at –20° C. to 100° C., for a period of 1 minute to 100 hours and preferably for 5 minutes to 50 hours.

(b) A compound of general formula [1a] in which Y is an oxygen atom, or a salt thereof, can be obtained by subjecting a compound of general formula [2b] or salt thereof to an ammonolysis reaction of carboxylic ester in the presence or absence of a catalyst.

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; alcohols such as methanol, ethanol, propanol and the like; sulfoxides such as dimethyl sulfoxide and the like; water, etc. These solvents may be used alone or as a mixture of two or more. This reaction may be carried out with the agents and under the conditions conventionally used in the ammonolysis of aromatic carboxylic esters. Preferably, however, ammonia gas, liquid ammonia or aqueous ammonia is used. These agents are used in an amount of at least 0.5 mol per mol of the compound of formula [2b] or its salt. It is also possible to use these solvents as a solvent, if desired. As the catalyst which may be used in this reaction according to the need, acid ammonium salts such as ammonium chloride; bases such as sodium methoxide, butyllithium and the like; and alkali metal amides such as sodium amide and the like can be referred to. The catalyst is used in an amount of 0.01 to 100 mol and preferably 0.01 to 20 mol, per mol of the compound of formula [2b] or its salt.

The reaction is carried out usually at a temperature of –100° C. to 250° C. and preferably at –78° C. to 100° C., for a period of 1 minute to 72 hours and preferably 30 minutes to 50 hours.

[Production Process I-2]

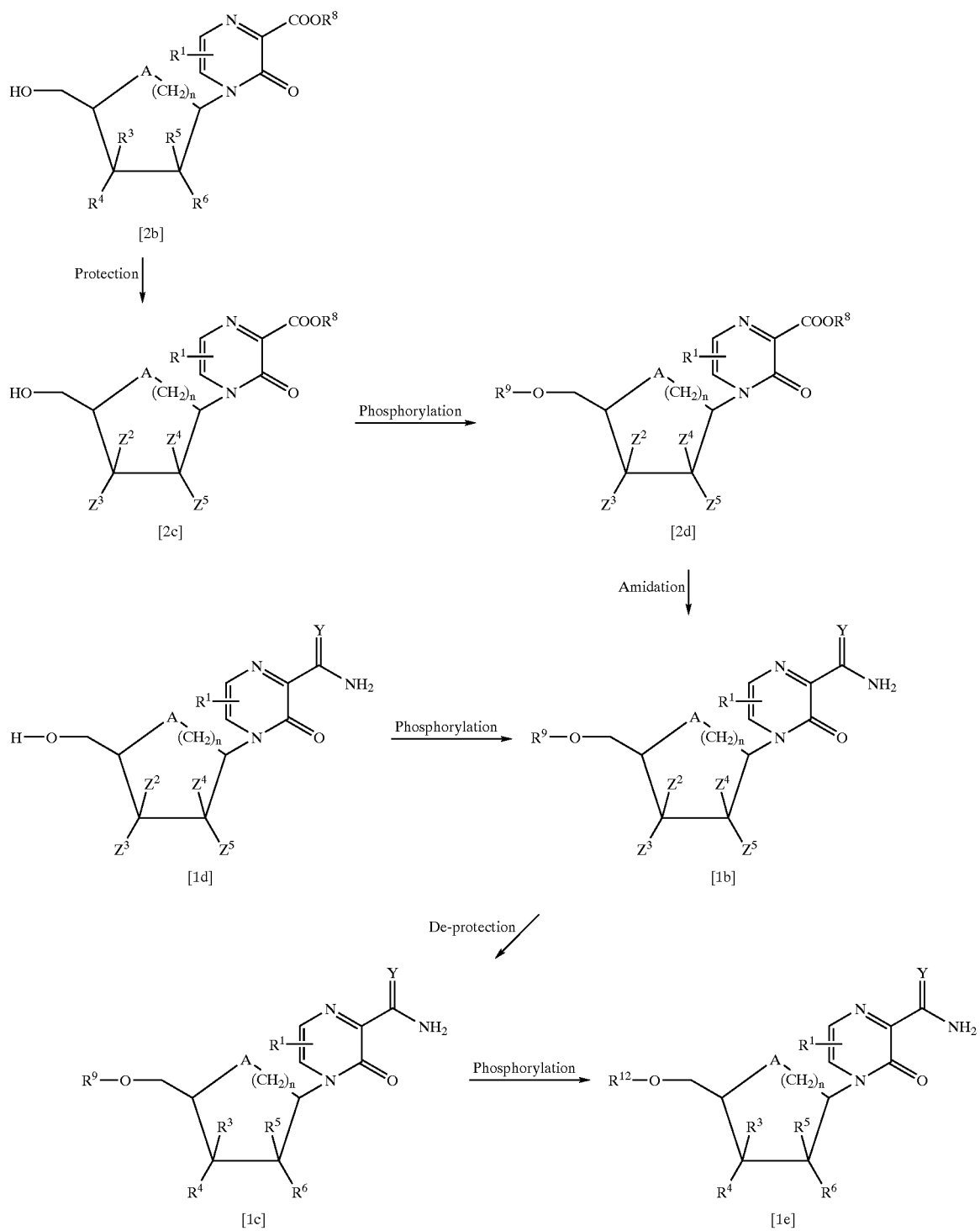

wherein $R^1$, $R^3$, $R^4$, $R^5$, $R^6$, $R^8$, $Z^2$, $Z^3$, $Z^4$, $Z^5$, A, n and Y are as defined above; $R^9$ represents a protected or unprotected mono-phosphoric acid group or a mono-phosphoric acid chloride; and $R^{12}$ represents a protected or unprotected di-phosphoric acid or tri-phosphoric acid group.

(a) The compound of general formula [2c] or salt thereof cab be obtained by protecting a compound of general formula [2b] or salt thereof with an agent in the presence or absence of an acidic catalyst or a base.

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylacetamide and the like; alcohols such as methanol, ethanol, propanol and the like; sulfoxides such as dimethyl sulfoxide and the like; ketones such as acetone and the like; water, etc. These solvents may be used alone or as a mixture of two or more.

As the reagent, those generally used for protection of hydroxyl group and amino group can be used, and preferably 2,2-dimethoxypropane, acetyl chloride and benzoyl chloride are used. If desired, these reagents may be produced in the reaction system. The amount of the reagent is at least an equimolar amount and preferably 1.0–10 mol per mol of the compound of formula [2b] or salt thereof.

As the acidic catalyst or the base used in this reaction, for example, p-toluenesulfonic acid, triethylamine and the like can be referred to. The amount thereof may both be 0.01–10 mol and preferably 0.05–10 mol per mol of the compound of formula [2b] or salt thereof.

This reaction is carried out usually at −50° C. to 170° C. and preferably 0° C. to 150° C., for a period of one minute to 24 hours and preferably 5 minutes to 10 hours.

(b) The compound of general formula [2d] or salt thereof can be obtained by (1) reacting a compound of general formula [2c] or salt thereof with a phosphorylating agent in the presence or absence of an additive according to the method described in Jikken Kagaku Koza, 4th Edition, Vol. 22, Pages 313–438 (edited by the Chemical Society Japan (corporate juricical person), 1992) or (2) reacting it with a phosphitizing agent and then with an oxidant.

In the method (1), the solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; sulfoxides such as dimethyl sulfoxide and the like; pyridine; etc. These solvents may be used alone or as a mixture of two or more.

As the phosphorylating agent, reagents generally used in the phosphorylation of hydroxyl group may be used. Examples of such phosphorylating agent include diesters of phosphoric acid such as dibenzyl phosphate and the like; dithioesters of phosphoric acid such as monocyclohexylammonium S,S'-diphenylphosphoro dithioate and the like; phosphoric acid chlorides such as phosphoryl chloride, diallyl chlorophosphonate and the like; etc. The phosphorylating agent is used at least in an equimolar amount and preferably in an amount of 1.0–5.0 mol per mol of the compound of formula [2c] and salt thereof. As additives, for example, azo compounds such as diethyl azodicarboxylate, diisopropyl azodicarboxylate and the like; phosphines such as triphenylphosphine and the like; allenesulfonic acid chlorides such as 2,4,6-triisopropylbenzenesulfonic acid chloride and the like; bases such as pyridine, tert-butylmagnesium chloride and the like; etc. can be referred to. These additives may be used in combination, if desired. The additive is used at least in an equimolar amount and preferably in an amount of 1.0–5.0 mol per mol of the compound of formula [2c] or salt thereof.

This reaction is carried out usually at a temperature of −50° C. to 170° C. and preferably 0° C. to 100° C., for a period of 1 minute to 72 hours and preferably 5 minutes to 24 hours.

In the method (2), the solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; sulfoxides such as dimethyl sulfoxide and the like; pyridine; etc. These solvents may be used alone or as a mixture of two or more.

As the phosphitizing agents, reagents generally used in the phosphitization of hydroxyl group may be used. Examples include phosphoroamidites such as diallyl diisopropylphosphoroamidite and the like, and phosphorous acid chlorides such as diallyl phosphorochloridite and the like. The phosphitizing agent is used in an amount of at least in an equimolar amount and preferably in an amount of 1.0–3.0 mol per mol of compound of formula [2c] and salt thereof. As the additive, for example, tetrazole compounds such as 1H-tetrazole and the like, and bases such as pyridine, collidine and the like are used, and those additives may be used in combination, if desired. The additive is used at least in an equimolar amount and preferably in an amount of 1.0–5.0 mol per mol of the compound of formula [2c] or salt thereof.

As the oxidants used in this reaction, for example, peroxides such as m-chloroperbenzoic acid, tert-butyl hydroperoxide and the like, and halogen compounds such as iodine and the like can be referred to. The oxidant is used at least in an equimolar amount and preferably in an amount of 1.0–5.0 mol per mol of the compound of formula [2c] or salt thereof.

This reaction is carried out usually at −78° C. to 100° C., and preferably at −50° C. to 50° C., for a period of 1 minute to 24 hours and preferably 5 minutes to 6 hours.

(c) The compound of general formula [1b] or salt thereof can be obtained by carrying out a reaction according to Production Process I-1 (b), by the use of a compound of general formula [2d] or salt thereof.

(d) The compound of general formula [1c] or salt thereof can be obtained by carrying out a reaction according to Production Process I-1 (a), by the use of a compound of general formula [1b] or salt thereof.

(e) The compound of general formula [1b] or salt thereof can be obtained by carrying out a reaction according to Production process I-2 (b), by the use of a compound of general formula [1d] or salt thereof.

(f) The compound of general formula [1e] or salt thereof can be obtained by reacting a compound of general formula [1c] or salt thereof with a phosphorylating agent in the presence or absence of a condensing agent according to the procedure described in, for example, Chem. Rev., Vol. 100, Pages 2047–2059 (2000).

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; sulfoxides such as dimethyl sulfoxide and the like; pyridine; etc. These solvents may be used alone or as a mixture of two or more.

As the phosphorylating agent, reagents generally used in the phosphorylation of mono-phosphoric acid group may be used. Examples of such phosphorylating agent include salts of phosphoric acid such as tri-n-butylammonium phosphate, n-butylammonium pyrophosphate and the like, and these phosphorylating agents may be synthesized in the reaction system, if desired. The phosphorylating agent is used at least in an equimolar amount and preferably in an amount of 1.0–10 mol, per mol of the compound of formula [1c] or salt thereof. As the condensing agent, for example, imidazoles such as N,N-carbonyldiimidazole, N-methylimidazole and the like, and amines such as morpholine, diisopropylamine and the like can be used, and these amines may be used in combination, if desired. The condensing agent is used at least in an equimolar amount and preferably in an amount of 1.0–5.0 mol per mol of the compound of formula [1c] or salt thereof.

This reaction is carried out usually at −50° C. to 100° C., and preferably at 0° C. to 50° C., for a period of 1 minute to 72 hours and preferably for 5 minutes to 24 hours.

as acetonitrile and the like; amides such as N,N-dimethylformamide, N,N-dimethylacetamide and the like; sulfoxides such as dimethyl sulfoxide and the like; and halogenated hydrocarbons such as methylene chloride, chloroform, dichloroethane and the like. These solvents may be used alone or as a mixture of two or more.

The silylating agent used in the reaction (1) may be any silylating agents conventionally used for converting a carbonyl group into a silyl enol ether. Examples thereof include 1,1,1,3,3,3-hexamethyldisilazane, N,O-bis(trimethylsilyl) acetamide, trimethylsilyl chloride, and the like. The silylating agent is used at least in an equimolar amount and preferably in an amount of 1.0–10.0 mol per mol of the compound of formula [3a] or salt thereof.

As the additive which may be used in this reaction according to the need, for example, ammonium sulfate and

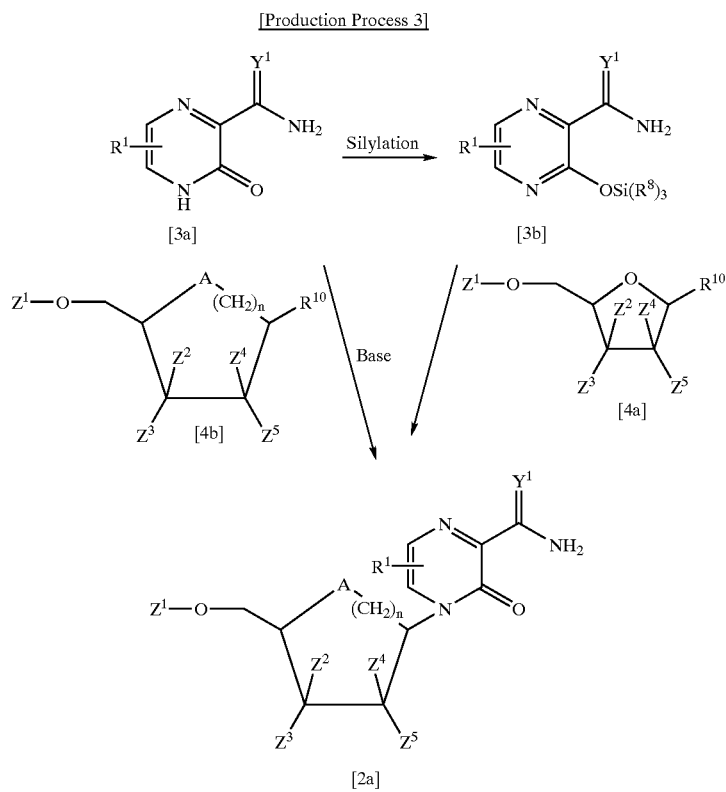

wherein $R^1$, $R^8$, A, n, $Z^1$, $Z^2$, $Z^3$, $Z^4$ and $Z^5$ are as defined above; $Y^1$ represents an oxygen atom or NH group; and $R^{10}$ represents a halogen atom, a carbonyloxy group or a sulfonyloxy group.

(a) The compound of general formula [2a] or salt thereof can be obtained by (1) converting a compound of general formula [3a] or salt thereof into a compound of general formula [3b] or salt thereof according to the usually utilized silylation method in the presence or absence of an additive and thereafter (2) reacting it with a compound of general formula [4a] or salt thereof in the presence or absence of a Lewis acid.

The solvents used in these reactions are not particularly limited, unless exercising an adverse influence on the reactions. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such the like can be referred to. Said additive is used in an amount of 0.01–10.0 mol and preferably 0.05–5.0 mol per mol of the compound of formula [3a] or salt thereof.

This reaction is carried out usually at 0–200° C. and preferably 0–150° C., for a period of 5 minutes to 24 hours and preferably 5 minutes to 12 hours.

In the reaction (2), the compound of formula [4a] or salt thereof is used in an amount of 0.5–10 mol and preferably 0.5–5 mol, per mol of the compound of formula [3a] or salt thereof.

As the Lewis acid which may be used in this reaction according to the need, for example, trimethylsilyltrifluoromethanesulfonic acid, stannic (IV) chloride, titanium (IV) chloride, zinc chloride and the like can be referred to. The Lewis acid is used at least in an amount of 0.5 mol and preferably in an amount of 0.5–10 mol per mol of the compound of formula [3a] or salt thereof.

This reaction is carried out usually at 0–100° C. and preferably at 0–50° C., for a period of 1 minute to 72 hours and preferably 5 minutes to 24 hours.

(b) The compound of general formula [2a] or salt thereof can be obtained by reacting a compound of general formula [3a] or salt thereof with a compound of general formula [4b] or salt thereof in the presence or absence of an additive, by the use of a base as a de-acidifying agent.

The solvent used in this reaction is not limited, unless exercising an adverse influence on the reaction. Examples thereof include aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; nitrites such as acetonitrile and the like; amides such as N,N-dimethylformamide, N,N-dimethylacetamide and the like; sulfoxides such as dimethyl sulfoxide and the like; etc. These solvents may be used alone or as a mixture of two or more.

As the bases used in this reaction, for example, inorganic and organic bases such as triethylamine, potassium tert-butoxide, potassium carbonate, sodium carbonate, cesium carbonate, sodium hydride and the like can be referred to. In this reaction, the compound of general formula [4b] or salt thereof is used in an amount of 0.1–5 mol and preferably 0.2–2 mol per mol of the compound of general formula [3a] or salt thereof. In this reaction, the base is used in an amount of 0.1–10 mol and preferably 0.2–10 mol per mol of the compound of general formula [3a] or salt thereof.

As the additive which may be used in this reaction according to the need, for example, palladium catalysts such as tetrakis-triphenylphosphine palladium and the like; phosphines such as triphenylphosphine and the like; and polyethers such as 18-crown-6-ether and the like can be referred to. The additive is used in an amount of 0.01–10 mol and preferably 0.03–5.0 mol, per mol of the compound of formula [3a] or salt thereof.

This reaction is carried out usually at −50° C. to 170° C. and preferably at 0° C. to 120° C., for a period of one minute to 72 hours and preferably 5 minutes to 24 hours.

[Production Process I-4]

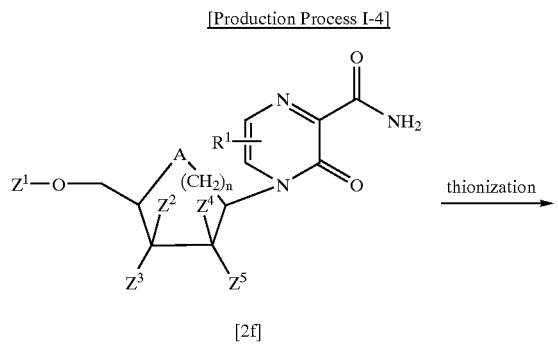

[2f]

thionization

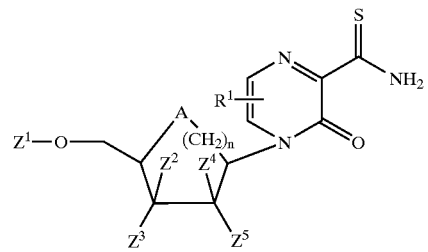

[2g]

wherein $R^1$, A, n, $Z^1$, $Z^2$, $Z^3$, $Z^4$ and $Z^5$ are as defined above.

The compound of general formula [2g] or salt thereof can be obtained by reacting a compound of general formula [2f] or salt thereof with a thionizing agent in the presence or absence of a base according to the description of, for example, Shin Jikken Kagaku Koza, Vol. 14, Pages 1819–1831 (edited by the Chemical Society Japan (corporate juricical person), 1978).

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; amides such as N,N-dimethylformamide, N,N-dimethylacetamide and the like; sulfoxides such as dimethyl sulfoxide and the like; etc. These solvents may be used alone or as a mixture of two or more.

As the thionizing agent, reagents which are conventionally used for thionization of acid amides may be used. Examples thereof include gaseous hydrogen sulfide, diphosphorus pentasulfide, Lawson reagent, etc. The thionizing agent is used in this reaction in an amount of 0.1–10 mol and preferably 0.2–5.0 mol, per mol of the compound of general formula [2f] or salt thereof.

As the base used in this reaction, for example, bases such as ammonia, triethylamine, morpholine, pyridine, 4-dimethylaminopyridine and the like can be referred to. In this reaction, the base is used at least in an amount of 0.01 mol per mol of the compound of formula [2f] or salt thereof. If desired, the base may be used as a solvent.

This reaction is carried out usually at −50° C. to 170° C. and preferably 0° C. to 120° C., for a period of 1 minute to 24 hours and preferably for 5 minutes to 6 hours.

Next, the process for producing the compounds of general formulas [2a], [2b], [3a'] and [3j] and salts thereof which are starting materials for the production of the compound of the present invention will be described.

The compounds of general formulas [2a], [2b], [3a'] and [3j] can be produced according to the methods well known in themselves or appropriate combination of the methods. For example, these compounds can be produced according to the following Production Process I-A.

[Production Process I-A]

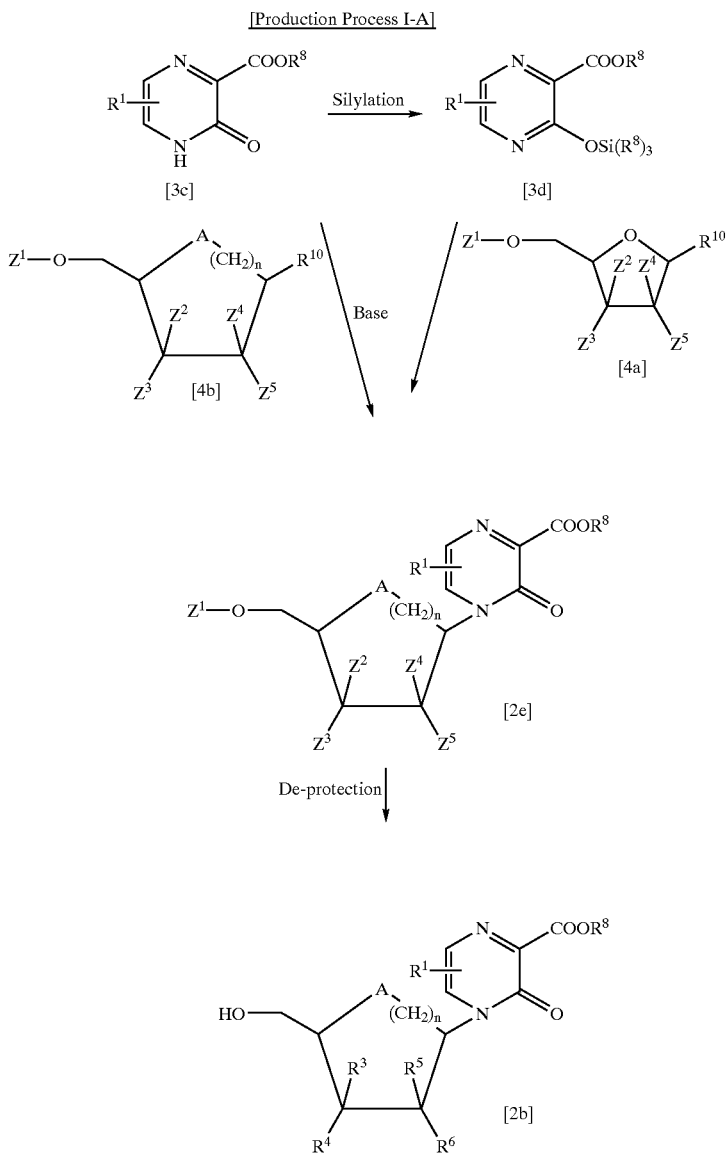

wherein $R^1$, $R^3$, $R^4$, $R^5$, $R^6$, $R^8$, A, n, $Z^1$, $Z^2$, $Z^3$, $Z^4$, $Z^5$ and $R^{10}$ are as defined above.

(a) The compound of general formula [2e] or salt thereof can be obtained by reacting a compound of general formula [3c] or salt thereof with a compound of general formula [4a] or salt thereof according to the method of Production Process I-3(a).

(b) The compound of general formula [2e] or salt thereof can be obtained by reacting a compound of general formula [3c] or salt thereof with a compound of general formula [4b] or salt thereof according to the method of Production Process I-3(b).

(c) The compound of general formula [2b] or salt thereof can be obtained by reacting a compound of general formula [2e] or salt thereof according to the method of Production Process I-1(a).

Among the starting materials of the above-mentioned reactions, the compound of general formula [3c] or salt thereof can be produced according to, for example, J. Heterocyclic Chem., Vol. 34, No. 1, Pages 27–32 (1997) or J. Med. Chem., Vol. 12, No. 2, Pages 285–287 (1969); the compound of general formula [4a] or salt thereof can be produced according to, for example, J. Med. Chem., Vol. 28, No. 7, Pages 904–910 (1985); and the compound of general formula [4b] or salt thereof can be produced according to J. Chem. Soc. PERKIN TRANS.1, Pages 2419–2425 (1992), J. Med. Chem., Vol. 36, No. 14, Pages 2033–2040 (1993) or Bio. Med. Chem. Lett., Vol. 6, No. 13, Pages 1457–1460 (1996).

[Production Process I-B]

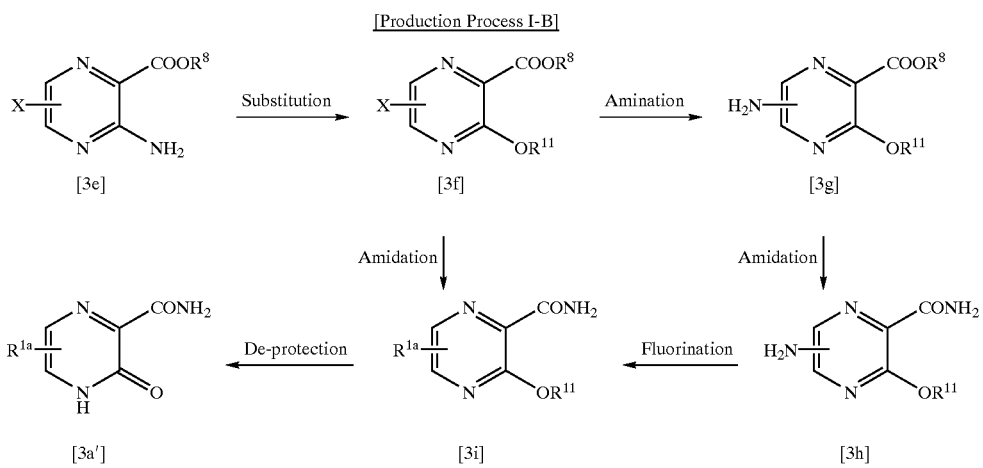

wherein $R^8$ is as defined above; $R^{1a}$ represents a halogen atom; $R^{11}$ represents a protecting group for hydroxyl group; and X represents a halogen atom other than fluorine atom.
(a) The compound of general formula [3f] or salt thereof can be obtained by reacting a compound of general formula [3e] or salt thereof by the use of a diazotizing agent and an alcohol.

The solvents used in this reaction may be any solvents unless exercising an adverse influence on the reaction. Examples of the solvent include inorganic acids such as sulfuric acid, hydrochloric acid, nitric acid and the like; ethers such as dioxane, tetrahydrofuran, anisole, diethylene glycol diethyl ether, dimethyl cellosolve and the like; halogenated hydrocarbons such as dichloromethane, chloroform, dichloroethane and the like; nitrites such as acetonitrile and the like; amides such as N,N-dimetbylformamide, N-methyl-2-pyrrolidone and the like; sulfoxides such as dimethyl sulfoxide and the like; amines and amine oxides such as triethylamine, N,N-dimethylaniline, pyridine-N-oxide and the like; ketones such as acetone and the like; alcohols such as methanol, ethanol and the like; water,; etc. If desired, these solvents may be used as a mixture. The diazotizing agents used in this invention are not particularly limited, so far as they are conventionally used for diazotization of aromatic amino compounds. Preferably, however, nitrites of alkali metals such as sodium nitrite and the like are used. The diazotizing agent is used at least in an equimolar amount and preferably in an amount of 1.0–5.0 mol, per mol of the compound of formula [3e] or salt thereof.

As the alcohol used in this reaction, for example, methanol and the like can be referred to. The alcohol is used at least in an equimolar amount to the compound of formula [3e] or salt thereof. It is also possible to use the alcohol as a solvent, if desired.

This reaction is carried out usually at −70° C. to 200° C. and preferably at −50° C. to 100° C., for a period of 1 minute to 24 hours and preferably 30 minutes to 10 hours.
(b) The compound of general formula [3g] or salt thereof can be obtained by (1) reacting a compound of general formula [3f] or salt thereof with an imine in the presence of a catalyst and a base as a de-acidifying agent according to the method disclosed in literature [Tetrahedron Letters, Vol. 38, No. 36, Pages 6367–6370 (1997)], and thereafter (2) hydrolyzing it in the presence of an additive.

In the reaction (1), the solvents usable are not particularly limited unless exercising an adverse influence on the reaction. Examples thereof include aromatic hydrocarbons such as benzene, toluene, xylene and the like; ethers such as dioxane, tetrahydrofuran, anisole, diethylene glycol diethyl ether, dimethyl cellosolve and the like; etc. These solvents may be used alone or as a mixture of two or more.

In this reaction, the catalyst may be selected from combinations of a palladium catalyst such as palladium (II) acetate, tris(dibenzylidene-acetone) dipalladium and the like, a nickel catalyst such as bis(1,5-cyclooctadiene)-nickel (0) and the like and a phosphine ligand such as 1,1'-bis(diphenylphosphino)-ferrocene, (s)-(−)-2,2'-bis(diphenylphosphino)-1,1'-binaphthyl and the like. The catalyst is used in an amount of 0.001–1.0 mol and preferably 0.002–0.5 mol per mol of the compound of formula [3f] or salt thereof.

As the base used in this reaction, alkali metal salts such as sodium tert-butoxide, cesium carbonate and the like can be referred to. The base is used at least in an equimolar amount and preferably in an amount of 1.0–3.0 mol per mol of the compound of formula [3f] or salt thereof.

As the imine used in this reaction, for example, benzophenoneimine and the like can be referred to. The imine is used at least in an equimolar amount and preferably in an amount of 1.0–3.0 mol per mol of the compound of formula [3f] or salt thereof.

This reaction is carried out usually at 0–120° C. and preferably at 5–100° C., for a period of 1 minute to 48 hours and preferably 5 minutes to 24 hours.
(2) In the reaction (2), the solvents usable are not particularly limited, unless exercising an adverse influence on the reaction. The solvents usable include, for example, ethers such as dioxane, tetrahydrofuran, anisole, diethylene glycol diethyl ether, dimethyl cellosolve and the like; alcohols such as methanol, ethanol and the like; water; etc. These solvents are used alone or as a mixture of two or more.

As the additive used in this reaction, for example, salts of organic and inorganic acids such as sodium acetate, hydroxylamine hydrochloride, ammonium formate and the like; inorganic acids such as hydrochloric acid and the like; and palladium catalysts such as palladium-carbon and the like can be referred to. It is possible to use these additives in combination, if desired. The additive is used in an amount of 0.01–50 mol and preferably 0.1–20 mol, per mol of the compound of general formula [3f] or salt thereof.

This reaction is carried out usually at 0–120° C. and preferably 5–100° C., for a period of 1 minute to 48 hours and preferably 3 minutes to 24 hours.

(c) The compound of the general formula [3h] or salt thereof can be obtained by reacting a compound of general formula [3g] or salt thereof according to the method of Production Process I-1(b).

(d) The compound of general formula [3i] or salt thereof can be obtained by subjecting a compound of general formula [3h] or salt thereof to de-amination of amino group by the use of a diazotizing agent in the presence of an acid, in the presence or absence of an additive according to the method described in, for example, Fusso Kagaku Nyumon, Pages 219–230 (edited by Nippon Gakujutsu Shinkokai, 155 Fluorine Chemistry Committee, 1997), and thereafter subjecting it to a fluorination reaction.

The solvent used in this reaction is not particularly limited, unless exercising an adverse influence on the reaction. Examples of the solvent usable include ethers such as dioxane, tetrahydrofuran, anisole, diethylene glycol diethyl ether, dimethyl cellosolve and the like; halogenated hydrocarbons such as dichloromethane, chloroform, dichloroethane and the like; nitrites such as acetonitrile and the like; amides such as N,N-dimethylformamide, N-methyl-2-pyrrolidone and the like; sulfoxides such as dimethyl sulfoxide and the like; amines and amine oxides such as triethylamine, N,N-dimethylaniline, pyridine, pyridine-N-oxide and the like; ketones such as acetone and the like; water; etc. These solvents may be used as a mixture, if desired.

The diazotizing agents used in this reaction may be any reagents so far as they are conventionally used for diazotization of aromatic amino compounds. Preferable diazotizing agents are, for example, alkali metal salts of nitrous acid such as sodium nitrite and the like. The diazotizing agent is used at in an equimolar amount, preferably in an amount of 1.0–5.0 mol and further preferably 1.0–1.5 mol, per mol of the compound of formula [3h] or salt thereof.

The acid used in this reaction is not particularly limited, unless exercising an adverse influence on the reaction. Examples thereof include acids such as hydrochloric acid, hydrofluoroboric acid, hydrogen fluoride and the like; solutions of hydrogen fluoride in bases such as a solution of hydrogen fluoride in pyridine, etc. These acids may be used as a mixture, if desired.

In this reaction, the acid is used at least in an amount of 1 mL and preferably 1–50 mL per g of the compound of general formula [3h] or salt thereof, as expressed in terms of volume/weight ratio.

As the additive used in this reaction, hydrofluoroboric acid, sodium tetrafluoride, ammonium fluoroborate and the like can be referred to. The acid is used at least in an equimolar amount and preferably 1.0–20.0 mol, per mol of the compound of formula [3h] or salt thereof.

This reaction is carried out usually at −70° C. to 100° C. and preferably at −60° C. to 30° C., for a period of 50 minutes to 24 hours and preferably one hour to 10 hours.

(e) The compound of general formula [3i] or salt thereof can be obtained by reacting a compound of general formula [3f] or salt thereof according to Production Process I-1 (b).

(f) The compound of general formula [3a'] or salt thereof can be obtained by reacting a compound of general formula [3i] or salt thereof with a de-protecting agent.

The solvent used in this reaction is not particularly limited, unless exercising an adverse influence on the reaction. Examples thereof include water; alcohols such as methanol, ethanol, propanol and the like; thioalcohols such as ethanethiol, thiophenol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; thio ethers such as dimethyl sulfide and the like; ketones such as acetone, methyl ethyl ketone and the like; nitrites such as acetonitrile and the like; amides such as N,N-dimethylformamide, N,N-dimethylacetamide and the like; sulfoxides such as dimethyl sulfoxide and the like; inorganic acids such as sulfuric acid, hydrochloric acid and the like; carboxylic acids such as acetic acid, trifluoroacetic acid and the like; sulfonic acids such as trifluoromethanesulfonic acid and the like; organic bases such as pyridine, triethylamine and the like; water; etc. These solvents may be used alone or as a mixture of two or more.

As the de-protecting agent, those agents which are conventionally used for de-protecting the protected aromatic alcohol may be used. Preferably, trimethylsilyl iodide and the like can be referred to. It is also allowable to generate the de-protecting agent in the reaction system. The de-protecting agent is used in an amount of 0.01–50 mol and preferably 0.1–30 mol, per mol of the compound of formula [3i] or salt thereof.

This reaction is carried out usually at −80° C. to 200° C. and preferably 0° C. to 160° C., for a period of one minute to 48 hours and preferably 5 minutes to 20 hours.

The compound of general formula [3e] or salt thereof which is a starting material of the above-mentioned reaction can be produced according to, for example, the method described in J. Am. Chem. Soc., Vol. 71, Pages 2798–2800 (1949).

[Production Process I-C]

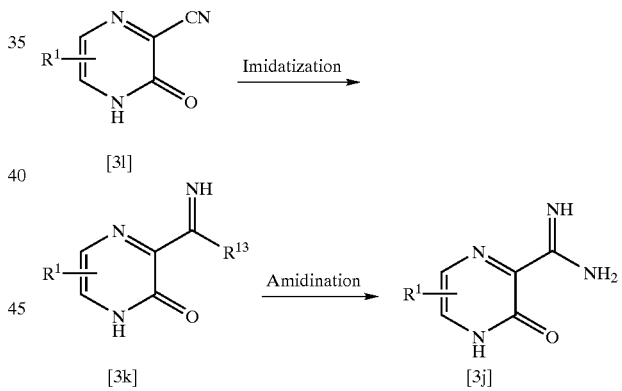

wherein $R^1$ is as defined above, and $R^{13}$ represents a lower alkoxy group or an aryloxy group.

(a) The compound of general formula [3k] or salt thereof can be obtained by reacting a compound of general formula [3l] or salt thereof with an alcohol in the presence or absence of an acidic catalyst or a base according to the procedure described in, for example, Shin Jikken Kagaku Koza, Vol. 14, Pages 1599–1602 (edited by the Chemical Society Japan (corporate juricical person), 1978).

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; amides such as N,N-dimethylformamide, N,N-dimethylacetamide and the like;

sulfoxides such as dimethyl sulfoxide and the like; etc. These solvents may be used alone or as a mixture of two or more.

As the alcohol used in this reaction, for example, methanol, ethanol, phenol and the like can be referred to. The alcohol is used at least in an equimolar amount based on the compound of formula [3l] or salt thereof. It is also allowable to use the alcohol as a solvent, if desired.

As the acidic catalyst used in this reaction, those reagents which are conventionally used for imidation of nitriles may be used. For example, hydrogen chloride and the like can be used for this purpose. The acidic catalyst is used in an amount of at least 0.1 mol per mol of the compound of formula [3l] or salt thereof.

As the base used in this reaction, for example, metal alkoxides such as sodium methoxide, sodium ethoxide, sodium phenoxide and the like can be referred to. It is also allowable to produce these bases in the reaction system, if desired. In this reaction, the base is used in an amount of at least 0.01 mol and preferably 1.0–5.0 mol, per mol of the compound of formula [3l] or salt thereof.

This reaction is carried out usually at −78° C. to 170° C. and preferably at −40° C. to 120° C., for a period of one minute to 72 hours and preferably 5 minutes to 24 hours.

(b) The compound of general formula [3j] or salt thereof can be obtained by reacting a compound of general formula [3k] or salt thereof with an reagent according to the procedure described in, for example, Shin Jikken Kagaku Koza, Vol. 14, Pages 1614–1617 (edited by the Chemical Society Japan (corporate juricical person), 1978).

The solvent used in this reaction is not particularly limited, unless exercising an adverse influence on the reaction. Examples thereof include aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; amides such as N,N-dimethylformamide, N,N-dimethylacetamide and the like; sulfoxides such as dimethyl sulfoxide and the like; etc. These solvents may be used alone or as a mixture of two or more.

As said reagent used in this reaction, those reagents which are conventionally used for amidination of imidates may be used. Examples of said reagent include gaseous ammonia, alcoholic solution of ammonia, aqueous solution of ammonia, and ammonium salts of acids such as ammonium chloride and the like. The reagent is used at least in an equimolar amount based on the compound of formula [3k] or salt thereof. It is also allowable to use the reagent as a solvent, if desired.

This reaction is carried out usually at −78° C. to 170° C. and preferably at 0° C. to 120° C., for a period of one minute to 72 hours and preferably 5 minutes to 24 hours,

[Production Process I-D]

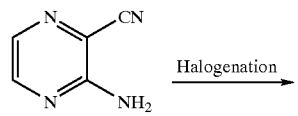

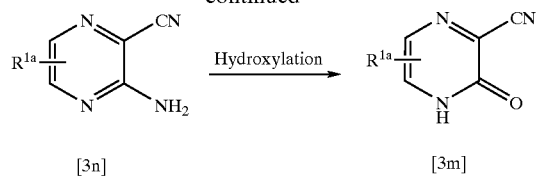

wherein $R^{1a}$ is as defined above.

(a) The compound of general formula [3m] or salt thereof can be produced by reacting a compound of general formula [3n] or salt thereof with a diazotizing agent and a hydroxylating agent in the presence or absence of an additive, according to the procedure described in, for example, Shin Jikken Kagaku Koza, Vol. 14, Pages 537–538 (edited by the Chemical Society Japan (corporate juricical person), 1977).

The solvent used in this reaction is not particularly limited, unless exercising an adverse influence on the reaction. Examples of the solvent include in organic acids such as sulfuric acid, hydrochloric acid, nitric acid and the like; ethers such as dioxane, tetrahydrofuran, anisole, diethylene glycol diethyl ether, dimethyl cellosolve and the like; halogenated hydrocarbons such as dichloromethane, chloroform, dichloroethane and the like; nitrites such as acetonitrile and the like; amides such as N,N-dimethylformamide, N-methyl-2-pyrrolidone and the like; sulfoxides such as dimethyl sulfoxide and the like; amines and amine oxides such as triethylamine, N,N-dimethylaniline, pyridine-N-oxide and the like; ketones such as acetone and the like; water; etc. These solvents may be used alone or as a mixture.

The diazotizing agents used in this reaction are not particularly limited, so far as they are conventionally used for the deaminohydroxylation of aromatic amino compounds. Preferably, alkali metal nitrites such as sodium nitrite and the like are used. The diazotizing agent is used at least in an equimolar amount, preferably in an amount of 1.0–5.0 mol, and further preferably 1.0–2.0 mol, per mol of the compound of general formula [3n].

As the hydroxylating agent used in this reaction, for example, water and the like can be referred to. The hydroxylating agent is used at least in an equimolar amount to the compound of formula [3n], though it is also possible to use the hydroxylating agent as a solvent, if desired.

As the additive used in this reaction, for example, copper salts such as copper sulfate and the like; and inorganic bases such as sodium hydroxide, sodium carbonate and the like can be referred to. The additive is used in an amount of 0.01–100 mol and preferably 0.1–50 mol, per mol of the compound of formula [3n].

This reaction is carried out usually at −70° C. to 200° C. and preferably at −50° C. to 100° C., for a period of one minute to 24 hours and preferably 30 minutes to 10 hours.

(b) The compound of general formula [3n] or salt thereof can be obtained by (1) reacting a compound of general formula [3o] or salt thereof with an electrophilic fluorinating agent in the presence or absence of an additive, and concretely saying, according to the procedure described in Fusso no Kagaku, Pages 28–37 (edited by Kodansha Scientific, 1993) or (2) reacting a compound of formula [3o] or salt thereof with a halogenating agent in the presence or absence of an additive according to the procedure described in, for example, Shin Jikken Kagaku Koza, Vol. 14, Pages 354–360 (edited by the Chemical Society Japan (corporate juricical person), 1977).

In the method (1), the solvents used are not particularly limited, unless exercising an adverse influence on the reaction. Examples of the solvent include halogenated hydrocarbons such as methylene chloride, chloroform, fluorotrichloromethane, 1,1,2-trichlorotrifluorethane and the like; ethers such as diethyl ether, tetrahydrofuran, diethylene glycol diethyl ether, dimethyl cellosolve and the like; alcohols such as methanol and the like; nitrites such as acetonitrile and the like; organic acids such as acetic acid, formic acid, trifluoroacetic acid and the like; inorganic acids such as hydrofluoric acid, sulfuric acid and the like; water; etc. These solvents may be used alone or as a mixture of two or more.

The electrophilic fluorinating agents used in this reaction are not particularly limited, so far as they are conventionally used for the addition reaction of fluorine atoms to carbon-carbon multiple bonds. Preferable examples thereof include fluorine gas, trifluoromethyl hypofluorite, acetyl hypofluorite, difluoroxenon, perchloryl fluoride, cesium sulfate fluorite, N-fluoropyridinium triflate, N-fluoro-N-alkylallenesulfonamide, N-fluorosaccharin sultam, N-fluorobis(trifluoromethanesulfone)-imide, N-fluorobis-(benzenesulfone)-imide and N-fluoro-O-benzenedisulfonimide. Of these electrophilic fluorinating agents, further preferable is fluorine gas. The electrophilic fluorinating agent is used in an amount of 0.05–50 mol and preferably 0.1–20 mol, per mol of the compound of formula [3o] or salt thereof.

The additive which may be used in this reaction according to the need is not particularly limited, so far as it is conventionally used in the electrophilic fluorinating reactions. Preferable examples thereof include acidic catalysts such as boron trifluoride, hydrofluoric acid and the like; organic and inorganic bases such as triethylamine, sodium fluoride and the like; and halogens such as chlorine, bromine, iodine and the like. These additives may be used alone or as a mixture of two or more. In this reaction, the additive is used in an amount of 0.01–10 mol and preferably 0.1–10 mol, per mol of the compound of formula [3o] or salt thereof.

This reaction is carried out usually at −80° C. to 170° C. and preferably at −80° C. to 100° C., for a period of one minute to 72 hours and preferably 5 minutes to 48 hours.

(2) In the method (2), the solvents used in the reaction are not particularly limited, unless exercising an adverse influence on the reaction. Examples of the solvent include halogenated hydrocarbons such as methylene chloride, chloroform, fluorotrichloromethane, 1,1,2-trichlorotrifluoroethane and the like; ethers such as diethyl ether, tetrahydrofuran, diethylene glycol diethyl ether, dimethyl cellosolve and the like; alcohols such as methanol and the like; nitrites such as acetonitrile and the like; organic acids such as acetic acid, formic acid, trifluoroacetic acid and the like; inorganic acids such as sulfuric acid and the like; water; etc. These solvents may be used alone or as a mixture of two or more.

The halogenating agents used in this reaction are not particularly limited, so far as they are conventionally used in the halogenation of aromatic compounds. Preferable examples thereof include bromine, chlorine, sulfuryl chloride, N-bromosuccinimide, N-chlorosuccinimide and the like. The halogenating agent is used in an amount of 0.05–50 mol and preferably 0.1–20 mol, per mol of the compound of formula [3o] or salt thereof.

The additives used in this reaction according to the need are not particularly limited, so far as they are conventionally used in the halogenation of aromatic compounds. Preferable examples thereof include sodium bromide, lead tetraacetate, titanium (IV) chloride, aluminum chloride, silver sulfate and the like. These additives may be used alone or as a mixture of two or more. In this reaction, the additive is used in an amount of 0.01–10 mol and preferably 0.1–10 mol, per mol of the compound of formula [3o] or salt thereof.

This reaction is carried out usually at −80° C. to 170° C. and preferably −80° C. to 100° C., for a period of one minute to 72 hours and preferably 5 minutes to 48 hours.

In the production processes mentioned above, all the compounds may be used in the form of salt thereof. As said salt, the same ones as described in the paragraph of salt of compound of general formula [1] can be used. If desired, these reactions may be carried out in an atmosphere of inert gas such as nitrogen gas. The compound of general formula [1] or salt thereof which has been obtained in the above-mentioned manner can be converted to other compounds of general formula [1] or salt thereof, by subjecting them to reactions known in themselves such as oxidation, reduction, rearrangement, substitution, halogenation, dehydration, hydrolysis and the like or appropriate combination of these reactions.

Some of the compounds referred to in the above-mentioned production processes may have isomers such as optical isomers, geometrical isomers, tautomers, etc. In such cases, these isomers are also usable in the present invention, and solvated products, hydrates and various crystal forms are also usable. After completion of the reaction, the objective compound may be sent to the next step of reaction without being isolated, if desired.

Some of the compounds referred to in the above-mentioned production processes may have an amino group, a hydroxyl group or a carboxyl group. It is also possible, if desired, to protect these groups with usual protecting group previously, and after the reaction, to eliminate the protecting group by a method well known in itself.

The compound of general formula [1] or salt thereof can be isolated, purified or recrystallized by the conventional methods such as extraction, crystallization and/or column chromatography, etc.

The compound of the present invention is formulated together with various pharmaceutical additives such as excipient, binder, disintegrator, disintegration-preventor, antiblocking and antisticking agent, lubricant, absorption-adsorption carrier, solvent, extender, isotonicity agent, dissolution assistant, emulsifying agent, suspending agent, thickening agent, coating agent, absorption promoter, gelation-coagulation promoter, light stabilizer, preservative, moisture-proofing agent, emulsion-suspension-dispersion stabilizer, color protector, deoxygenation-oxidation-preventor, sweeting-flavoring agent, coloring agent, foaming agent, antifoaming agent, pain-killer, antistatic agent, buffering agent, pH regulator, etc., and formed into a pharmaceutical composition such as oral agent (tablet, capsule, powder, granule, fine granule, pill, suspension, emulsion, solution, syrup, etc.), injection, suppository, external agent (ointment, plaster, etc.), aerosol, etc.

The above-mentioned formulations are made into pharmaceutical preparations according to the usual methods.

Solid preparations for oral use such as tablet, powder, granule and the like are prepared, according to the usual method, together with pharmaceutical additives for solid preparations including excipients such as lactose, sucrose, sodium chloride, glucose, starch, calcium carbonate, kaolin, crystalline cellulose, anhydrous calcium secondary phosphate, partly pregelatinized starch, corn starch, alginic acid and the like; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, sodium alginate, gum arabic, hydroxypropylmethylcellulose, hydroxypropylcellulose, water, ethanol and the like; disintegrators such as dry starch, alginic acid, agar powder, starch, crosslinked polyvinyl pyrrolidone, crosslinked sodium carboxymethylcellulose, calcium carboxymethylcellulose, sodium starch glycolate, and the like; disintegration-preventors such as stearyl alcohol, stearic acid, cacao butter, hydrogenated oil and the like; antiblocking and antisticking agents such as aluminum silicate, calcium hydrogen phosphate, magnesium oxide, talc, silicic acid anhydride and the like; lubricants such as carnauba wax, light silicic acid anhydride, aluminum silicate, magnesium silicate, hardened oil, hardened vegetable oil derivatives, sesame oil, bleached bees wax, titanium oxide, dry aluminum hydroxide gel, stearic acid, calcium stearate, magnesium stearate, talc, calcium hydrogen phosphate, sodium lauryl sulfate, polyethylene glycol and the like; absorption promoters such as quaternary ammonium salts, sodium lauryl sulfate, urea, enzymes, and the like; absorption-adsorption carriers such as starch, lactose, kaolin, bentonite, silicic acid anhydride, hydrated silicon dioxide, magnesium metasilicate-aluminate, colloidal silicic acid and the like; etc.

Further, if desired, a tablet may be made into usual skin-covered tablets such as sugar-skin tablet, gelatin-coated tablet, stomach-soluble coated tablet, intestine-soluble coated tablet, or water-soluble film coated tablet.

A capsule is prepared by mixing together the above-mentioned pharmaceutical ingredients and filling the mixture thus obtained into a hard gelatin capsule, soft capsule, etc.

Further, an aqueous or oily suspension, a solution, a syrup and an elixir can be prepared by forming the pharmaceutical composition together with the above-mentioned additives for liquid preparation such as solvent, extender, isotonizing agent, emulsifier, suspension stabilizer, thickener, etc. into a liquid preparation according to the usual method.

A suppository can be prepared by adding an appropriate absorption promoter to polyethylene glycol, cacao butter, lanolin, higher alcohol, higher alcohol ester, gelatin, semi-synthetic glyceride, Witepsol or the like and forming the mixture together with the pharmaceutical composition into a suppository.

An injection is prepared by mixing the pharmaceutical composition together with pharmaceutical additives for liquid preparation including diluents such as water, ethyl alcohol, Macrogol, propylene glycol, citric acid, acetic acid, phosphoric acid, lactic acid, sodium lactate, sulfuric acid, sodium hydroxide and the like; pH regulators and buffering agents such as sodium citrate, sodium acetate, sodium phosphate and the like; stabilizers such as sodium pyrosulfite, ethylenediamine-tetraacetic acid, thioglycolic acid, thiolactic acid and the like; isotonizing agents such as sodium chloride, glucose, mannitol, glycerin and the like; dissolution assistants such as sodium carboxymethyl cellulose, propylene glycol, sodium benzoate, benzyl benzoate, urethane, ethanolamine, glycerin and the like; pain-killer such as calcium gluconate, chlorobutanol, glucose, benzyl alcohol and the like; local anesthetics; etc., and forming the mixture into an injection according to the usual method.

An ointment having a form of paste, cream or gel can be prepared by forming the pharmaceutical composition together with a base such as white vaseline, polyethylene, paraffin, glycerin, cellulose derivatives, polyethylene glycol, silicone, bentonite and the like; preservatives such as methyl paraoxybenzoate, ethyl paraoxybenzoate, propyl paraoxybenzoate and the like; stabilizers; wetting agents; etc. and making the mixture into an ointment according to the usual method.

A plaster can be prepared by applying the above-mentioned ointment, cream, gel or paste onto a usual support according to usual method. As the support, woven and unwoven fabrics made of cotton, staple fiber, or chemical fibers; and films or foamed sheets made of soft vinyl chloride, polyethylene, polyurethane and the like can be used.

The method for administering the above-mentioned pharmaceutical composition is not particularly specified, but the method may be properly decided according to the form of preparation, the age, sexuality and other conditions of patient, and the extent of symptom of patient.

The dosage of the active ingredient of the pharmaceutical composition of the present invention is properly decided according to the method of using the composition, the age and sexuality of patient, the form of disease, and other conditions. Usually, however, the composition in the terms of active ingredient may be administered at a dosage of 0.1–100 mg/kg/day to adult, either at once or in several portions.

Next, the method for producing the fluoropyrazine derivatives or salts thereof which are intermediates of the present invention will be explained below.

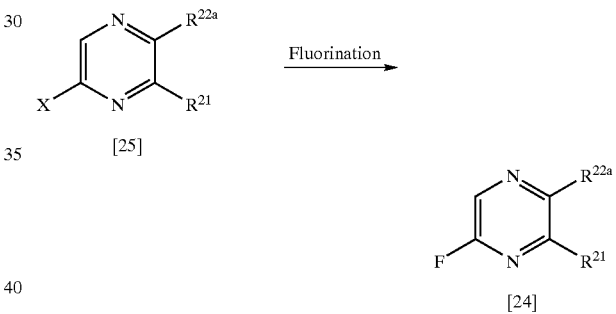

wherein $R^{21}$ is as defined above; $R^{22a}$ represents a hydrogen atom, a halogen atom, a nitro group, a protected amino group, a protected hydroxyl group or a substituted or unsubstituted phenylsulfanyl, phenylsulfinyl or phenylsulfonyl group; and X represents a halogen atom other than fluorine atom; provided that a case where $R^{21}$ is a hydrogen atom and $R^{22a}$ is a hydrogen atom is excepted.

The compound of general formula [24] or salt thereof can be obtained by reacting a compound of general formula [25] or salt thereof with a fluorinating agent in the presence or absence of an additive, according to the method described in, for example, Shin Jikken Kagaku Koza, Vol. 14, Pages 321–322 (edited by the Chemical Society Japan (corporate juridical person), 1977).

The solvent used in this reaction is not particularly limited, unless exercising an adverse influence on the reaction. Examples thereof include aromatic hydrocarbons such as benzene, toluene, xylene and the like; ethers such as tetrahydrofuran, 1,2-dimethoxyethane, diethylene glycol dimethyl ether and the like; nitrites such as acetonitrile, benzonitrile and the like; amides such as N,N-dimethylformamide, N,N-dimethylacetamide, N-methyl-2-pyrrolidone, 1,3-dimethyl-2-imidazolidinone and the like; sulfoxides such as dimethyl sulfoxide and the like; sulfones such as sulfolane, dimethyl sulfone and the like, nitrogen-containing heterocyclic compounds such as chollidine and the like; etc. These solvents may be used as a mixture, if desired.

As the fluorinating agent used in this reaction, alkali metal fluorides such as cesium fluoride, rubidium fluoride, potassium fluoride, sodium fluoride, lithium fluoride and the like; alkaline earth metal fluorides such as calcium fluoride and the like; other metal fluorides such as zinc fluoride, silver fluoride and the like; hydrogen fluoride; ammonium salts such as fluorinated tetrabutylammonium fluoride and the like; phosphonium salts; and hydrogen fluoride complexes thereof. These reagents may be used as a mixture, if desired. Although the amount of the fluorinating agent used in this reaction varies depending on the kind of the fluorinating agent, the amount of the fluorinating agent may be at least an equimolar amount based on the compound of general formula [25] or salt thereof, and preferably 1.0–20 mol and further preferably 1.0–10 mol per mol of the compound of formula [25] or salt thereof.

As the additive which may be used in this reaction according to the need, for example, quaternary ammonium salts such as tetra-n-butylammonium bromide, tetramethylammonium chloride, tetramethylammonium fluoride and the like; quaternary phosphonium salts such as tetraphenylphosphonium bromide and the like; polyethers such as 18-crown-6-ether, polyethylene glycol and the like; etc. can be referred to. These additives may be used as a mixture, if desired. Although the amount of the additive varies depending on the kind of the additive, the amount of the additive is 0.01–2.0 mol and preferably 0.1–1.0 mol, per mol of the compound of formula [25] or salt thereof.

This reaction may be carried out in an atmosphere of nitrogen, if desired. This reaction is carried out usually at 0–300° C. and preferably at 20–200° C., for a period of 10 minutes to 24 hours.

The compound of general formula [25] or salt thereof used as a starting compound of the above-mentioned reaction can be produced according to a method well known in itself, namely according to the description of literature [J. Med. Chem., Vol. 27, Pages 1634–1639 (1984); or Acta Poloniae Pharmaceutica, Vol. 33, Pages 153–161 (1976)].

[Production Process II-2[

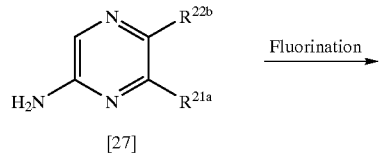

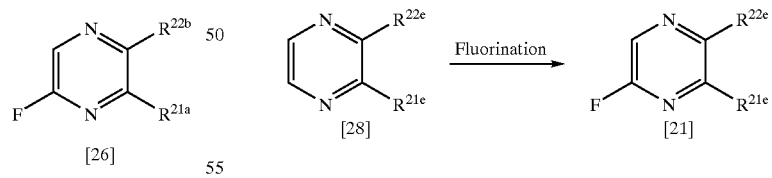

wherein $R^{21a}$ represents a hydrogen atom, a methyl group, a protected or unprotected hydroxymethyl, aminomethyl, carbamoyl or carboxyl group, a methyl group substituted with a protected or unprotected mercapto group, a halogenomethyl group, a formyl group or a nitrile group; and $R^{22b}$ represents a protected hydroxy or amino group or a halogen atom.

The compound of general formula [26] or salt thereof can be obtained by de-aminating the amino group of a compound of general formula [27] or salt thereof with a diazotizing agent in the presence of an acid, in the presence or absence of an additive and thereafter fluorinating the product, according to the method described in Fusso no Kagaku Nyumon, Pages 219–230 (edited by Nippon Gakujutsu Shinkokai, Fluorine Chemistry No.155 Committee, 1997).

The solvent used in this reaction is not particularly limited, unless exercising an adverse influence on the reaction. Examples thereof include ethers such as dioxane, tetrahydrofuran, anisole, diethylene glycol diethyl ether, dimethyl cellosolve and the like; halogenated hydrocarbons such as dichloromethane, chloroform, dichloroethene and the like; nitriles such as acetonitrile and the like; amides such as N,N-dimethylformamide, N-methyl-2-pyrrolidone and the like; sulfoxides such as dimethyl sulfoxide and the like; amines and amine oxides such as triethylamine, N,N-dimethylaniline, pyridine, pyridine-N-oxide and the like; ketones such as acetone and the like; water; etc. These solvents may be used as a mixture, if desired.

The diazotizing agent used in this reaction may be any diazotizing agent conventionally used for diazotization of aromatic amino compounds. Preferable examples thereof include alkali metal nitrites such as sodium nitrite and the like. The diazotizing agent is used at least in an equimolar amount, preferably 1.0–5.0 mol, and further preferably 1.0–1.5 mol, per mol of the compound of general formula [27] or salt thereof.

The acid used in this reaction is not particularly limited, unless exercising an adverse influence on the reaction. Examples thereof include acids such as hydrochloric acid, hydrofluoroboric acid, hydrogen fluoride and the like; and mixed solution of hydrogen fluoride in a basic substance such as a solution of hydrogen fluoride in pyridine; etc. These acids and solutions may be used as a mixture, if desired. The acids may be used as a solvent, as they are.

As expressed in terms of volume/weight ratio (mL/g), the amount of the acid used in this reaction is at least 1 mL and preferably 1–50 mL, per gram of the compound of general formula [27] or salt thereof.

As the additive used in this reaction, hydrofluoroboric acid, sodium tetrafluoride, ammonium borofluoride and the like can be referred to. The amount of the additive is at least an equimolar amount and preferably 1.0–20.0 mol, per mol of the compound of formula [27] or salt thereof.

This reaction is carried out usually at −70° C. to 100° C. and preferably at −60° C. to 30° C., for a period of 30 minutes to 24 hours and preferably 1 to 10 hours.

[Production Process II-3]

wherein $R^{21e}$ represents a hydrogen atom, a methyl group, a protected or unprotected hydroxymethyl, aminomethyl, carbamoyl or carboxyl group, a methyl group substituted with a protected or unprotected mercapto group, a halogenomethyl group, a formyl group, a nitrile group or a halogenated carbonyl group; and $R^{22e}$ represents a protected or unprotected hydroxyl or amino group, a halogen atom, a nitro group or an azido group.

The compound of general formula [21] or salt thereof can be obtained by reacting a compound of general formula [28] or salt thereof with an electrophilic fluorinating agent in the presence or absence of an additive, and concretely saying, according to the description of, for example, Fusso no Kagaku, Pages 28–37 (edited by Kodansha Scientific, 1993).

The solvent used in this reaction is not particularly limited, unless exercising an adverse influence on the reaction. Examples thereof include halogenated hydrocarbons such as methylene chloride, chloroform, fluorotrichloromethane, 1,1,2-trichlorotrifluoroethane and the like; ethers such as diethyl ether, tetrahydrofuran, diethylene glycol diethyl ether, dimethyl cellosolve and the like; alcohols such as methanol and the like; nitrites such as acetonitrile and the like; organic acids such as acetic acid, formic acid, trifluoroacetic acid and the like; inorganic acids such as hydrogen fluoride, sulfuric acid and the like; water; etc. These solvents may be used alone or as a mixture of two or more.

The electrophilic fluorinating agent used in this reaction is not particularly limited, so far as it is conventionally used for addition of fluorine atoms to carbon-carbon multiple bonds. Preferable examples thereof include fluorine gas, trifluoromethyl hypofluorite, acetyl hypofluorite, difluoroxenon, fluorinated perchloryl, cesium sulfate fluorite, N-fluoropyridinium triflate, N-fluoro-N-alkylallenesulfonamide, N-fluorosaccharine sultam, N-fluorobis(trifluoromethane-sulfone)-imide, N-fluorobis (benzenesulfone)-imide, and N-fluoro-O-benzenedisulfone-imide, and a further preferable example is fluorine gas. The electrophilic fluorinating agent is used in an amount of 0.05–50 mol and preferably 0.1–20 mol, per mol of the compound of general formula [28] or salt thereof.

The additive which may be used in this invention according to the need is not particularly limited, so far as it is a reagent conventionally used inn the electrophilic fluorination reactions. Preferable examples thereof include acidic catalysts such as boron trifluoride, hydrogen fluoride and the like; organic and inorganic bases such as triethylamine, sodium fluoride and the like; and halogens such as chlorine, bromine, iodine and the like. These additives may be used alone or as a mixture of two or more. In this reaction, the additive is used in an amount of 0.01–10 mol and preferably 0.1–10 mol, per mol of the compound of general formula [28] or salt thereof.

This reaction is carried out usually at −80° C. to 170° C. and preferably at −80° C. to 100° C., for a period of one minute to 72 hours and preferably 5 minutes to 48 hours.

The compound of general formula [28] or salt thereof used as a starting material of

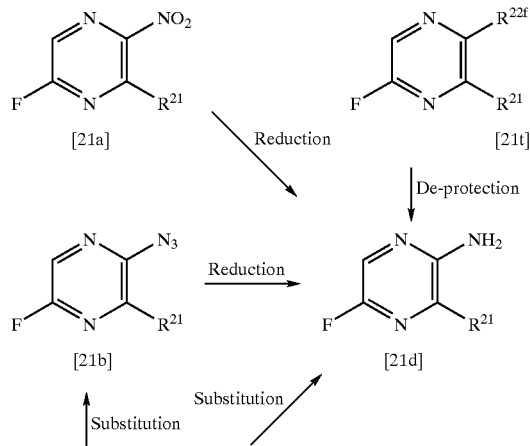

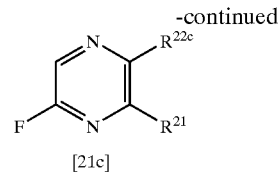

[21c]

wherein $R^{21}$ is as defined above, $R^{22c}$ represents a halogen atom, and $R^{22f}$ represents a protected amino group.

(4-1)

The compound of general formula [21d] or salt thereof can be obtained by reacting a compound of general formula [21a] or salt thereof with a reducing agent in the presence or absence of a catalyst, according to the description of, for example, Shin Jikken Kagaku Koza, Vol. 14, Pages 1333–1335 (edited by Chemical Society Japan (corporate juridical person), 1978).

The solvent used in this reaction is not particularly limited, unless exercising an adverse influence on the reaction. Examples thereof include aromatic hydrocarbons such as benzene, toluene, xylene and the like; ethers such as dioxane, tetrahydrofuran, anisole, diethylene glycol diethyl ether, dimethyl cellosolve and the like; ketones such as acetone and the like; amides such as N,N-dimethylformamide, N,N-dimethylacetamide and the like; alcohols such as methanol, ethanol, propanol and the like; organic acids such as acetic acid and the like; amines such as hydrazine and the like; water; etc. These solvents may be used alone or as a mixture of two or more.

The reducing agent used in this invention is not particularly limited, so far as it is an agent conventionally used for reduction of nitro group in aromatic nitro compounds. Preferable examples thereof include sodium amide, lithium amide, zinc, aluminum-nickel, tin, stannous (II) chloride, iron, sodium borohydride, cyclohexene, hydrogen gas, etc. The reducing agent is used in an amount of 0.01–100 mol and preferably 0.01–30 mol, per mol of the compound of formula [21a] or salt thereof.

As the catalyst which may be used in this reaction according to the need, for example, inorganic acids such as hydrochloric acid, sulfuric acid and the like; Lewis acids such as nickel (II) chloride, stannous (II) chloride and the like; metallic salts such as bis-(acetylacetonate) copper (II) and the like; palladium catalysts such as palladium-carbon, lead-poisoned palladium-calcium carbonate and the like; rhodium; Raney nickel; platinum (IV) oxide; etc. The palladium catalysts and Raney nickel are used in an amount of 0.01–100 parts by weight and preferably 0.1–10 parts by per part by weight of the compound of formula [21a] or salt thereof. The catalysts other than palladium catalyst and Raney nickel are used in an amount of 0.01–10 mol and preferably 0.01–5.0 mol, per mol of the compound of formula [21a] or salt thereof.

This reaction is carried out usually at −78° C. to 250° C. and preferably at −50° C. to 150° C., for a period of one minute to 72 hours and preferably 30 minutes to 24 hours.

(4-2)

The compound of general formula [21d] or salt thereof can be obtained by reacting a compound of general formula [21b] or salt thereof with a reducing agent in the presence or absence of a catalyst, according to the method described in Shin Jikken Kagaku Koza, Vol. 14, Page 1336 (edited by the Chemical Society Japan (corporate juridical person), 1978).

The solvent used in this reaction is not particularly limited, unless exercising an adverse influence on the reaction. Examples thereof include aromatic hydrocarbons such as benzene, toluene and the like; ethers such as dioxane, tetrahydrofuran, anisole, diethylene glycol diethyl ether, dimethyl cellosolve and the like; ketones such as acetone and the like; amides such as N,N-dimethylformamide, N,N-dimethylacetamide and the like; alcohols such as methanol, ethanol, propanol and the like; organic acids such as acetic acid and the like; amines such as hydrazine and the like; water; etc. These solvents may be used alone or as a mixture of two or more.

The reducing agent used in this reaction is not particularly limited, so far as it is an agent conventionally used in the reduction of azido group of aromatic azide compounds. Preferable examples thereof include zinc, chromium (II) chloride, tributyltin hydride, lithium aluminum hydride, hydrogen gas, and the like. The reducing agent is used in an amount of 0.01–100 mol and preferably 0.01–30 mol, per mol of the compound of general formula [21b] or salt thereof.

As the catalyst used in this reaction, for example, inorganic acids such as hydrochloric acid, sulfuric acid and the like; palladium-carbon, lead-poisoned palladium-calcium carbonate, platinum (IV) oxide and the like can be referred to. The catalyst is used in an amount of 0.01–10 mol and preferably 0.01–5.0 mol, per mol of the compound of formula [21b] or salt thereof. For example, when a palladium catalyst and Raney nickel are used, the amount of the catalyst may be 0.01–10 parts by weight and preferably 0.1–5.0 arts by weight per part by weight of the compound of formula [21b] or salt thereof.

This reaction is carried out usually at −78° C. to 250° C. and preferably at −50° C. to 150° C., for a period of one minutes to 72 hours and preferably 30 minutes to 24 hours.

(4-3)

The compound of general formula [21d] or salt thereof can be obtained by reacting a compound of general formula [21c] or salt thereof with an aminating agent in the presence or absence of a copper catalyst according to the method described in Shin Jikken Kagaku Koza, Vol. 14, Pages 1342–1351 (edited by Chemical Society Japan (corporate juridical person), 1978).

The solvent used in this reaction is not particularly limited, unless exercising an adverse influence on the reaction. Examples thereof include aromatic hydrocarbons such as benzene, toluene, xylene and the like; ethers such as dioxane, tetrahydrofuran, anisole, diethylene glycol diethyl ether, dimethyl cellosolve and the like; nitrites such as acetonitrile and the like; esters such as ethyl acetate and the like; amides such as N,N-dimethylformamide, N,N-dimethylacetamide and the like; alcohols such as methanol, ethanol, propanol and the like; sulfoxides such as dimethyl sulfoxide and the like; water; etc. These solvents may be used alone or as a mixture of two or more.

The aminating agent used in this reaction is not particularly limited, so far as it is an agent conventionally used in the amination by the nucleophilic substitution of aromatic halogen compounds. Preferable examples thereof include gaseous ammonia; aqueous ammonia; alkali metal amides such as sodium amide and the like; and ammonium salts such as ammonium carbonate and the like. The aminating agent is used at least in an equimolar amount and preferably in an amount of 2.0–30 mol per mol of the compound of formula [21c] or salt thereof.

As the copper catalyst used in this reaction, for example, copper powder, cuprous chloride and the like can be referred to. The copper catalyst is used in an amount of 0.01–30 mol and preferably 0.05–2 mol, per mol of the compound of formula [21c] or salt thereof.

This reaction is carried out usually at 0–250° C. and preferably at 0–40° C., for a period of one minute to 96 hours and preferably 30 minutes to 7 hours.

(4-4)

The compound of general formula [21b] or salt thereof can be obtained by reacting a compound of general formula [21c] or salt thereof with an azide-forming agent according to the method described in Shin Jikken Kagaku Koza, Vol. 14, Pages 1659–1666 (edited by Chemical Society Japan (corporate juridical person), 1978).

The solvent used in this reaction is not particularly limited, unless exercising an adverse influence on the reaction. Examples thereof include aromatic hydrocarbons such as benzene, toluene, xylene and the like; ethers such as dioxane, tetrahydrofuran, anisole, diethylene glycol diethyl ether, dimethyl cellosolve and the like; nitrites such as acetontrile and the like; esters such as ethyl acetate and the like; amides such as N,N-dimethylformamide, N,N-dimethylacetamide and the like; alcohols such as methanol, ethanol, propanol and the like; sulfoxides such as dimethyl sulfoxide and the like; water; etc. These solvents may be used alone or as a mixture of two or more.

The azide-forming agent used in this reaction is not particularly limited, so far as it is an agent used in the conventional azide-formation by nucleophilic substitution of aromatic halogen compounds. Preferable examples thereof include sodium azide and the like. The azide-forming agent is used at least in an equimolar amount, and preferably in an amount of 1.0–30 mol and further preferably 1.0–1.5 mol, per mol of the compound of formula [21c] or salt thereof.

This reaction is carried out usually at 0–250° C. and preferably at 0–40° C., for a period of one minute to 96 hours and preferably 5 minutes to 6 hours.

(4-5)

The compound of general formula [21d] or salt thereof can be obtained by reacting a compound of general formula [21t] or salt thereof with a de-protecting agent in the presence or absence of a catalyst, according to the usual method, namely according to the method described in Theodora W. Greene: PROTECTIVE GROUPS IN ORGANIC SYNTHESES, Third Edition, Pages 494–653 (edited by John Wiley & Sons, Inc., 1999).

The solvent used in this reaction is not particularly limited, unless exercising an adverse influence on the reaction. Examples of the solvent include water; alcohols such as methanol, ethanol, propanol and the like; thioalcohols such as ethanethiol, thiophenol and the like; aromatic hydrocarbons such as benzene, toluene, xylene and the like; halogenated hydrocarbons such as methylene chloride, chloroform, 1,2-dichlorethane and the like; ethers such as dioxane, tetrahydro furan, anisole, diethylene glycol diethyl ether, dimethyl cellosolve and the like; thioethers such as dimethyl sulfide and the like; ketones such as acetone and the like; nitriles such as acetonitrile and the like; amides such as N,N-dimethylformamide, N,N-dimethylacetamide and the like; sulfoxides such as dimethyl sulfoxide and the like; inorganic acids such as sulfuric acid, hydrochloric acid and the like; carboxylic acids such as acetic acid, trifluoroacetic acid and the like; sulfonic acids such as trifluoromethanesulfonic acid and the like; nitroalkanes such as nitromethane and the like; organic bases such as pyridine, triethylamine and the like; etc. These solvents may be used alone or as a mixture of two or more.

The de-protecting agent used in this reaction is not particularly limited, so far as it is conventionally used for de-protection of protected amino groups. Preferable examples thereof include hydrogen gas; ammonium formate; zinc; sodium; acid chlorides such as vinyl chloroformate, acetyl chloride and the like; organosilanes such as triethylsilane, trimethylsilyl iodide and the like; tributyltin hydride; alkali metal alkoxides such as potassium tert-butoxide and the like; alkali metal thioalkoxides such as sodium thiomethoxide and the like; 2,3-dichloro-5,6-dicyano-1,4-benzoquinone; sodium borohydride; alkali metal salts such as potassium fluoride, sodium iodide and the like; Lewis acids such as boron trifluoride, aluminum chloride, ruthenium chloride, zinc chloride and the like; inorganic acids such as hydrochloric acid, hydrobromic acid, sulfuric acid and the like; organic acids such as trifluoroacetic acid, methanesulfonic acid, p-toluenesulfonic acid and the like; inorganic bases such as potassium carbonate, sodium hydrogen carbonate, sodium hydroxide and the like; organic bases such as piperidine and the like; amines such as ammonia, hydrazine and the like; organolithium compounds such as methyllithium and the like; diammonium cerium nitrate; peroxides such as hydrogen peroxide, ozone, permanganic acid and the like; etc. The de-protecting agent is used in an amount of 0.01–1,000 mol and preferably 0.1–100 mol, per mol of the compound of formula [21t] or salt thereof.

The catalyst used in this reaction according to the need is not particularly limited, so far as it is conventionally used for de-protection of protected amino groups. Preferable examples thereof include palladium catalysts such as palladium-carbon and the like; rhodium, Raney nickel, platinum (IV) oxide and the like. For example, the palladium-carbon and the Raney nickel are used in an amount of 0.01–10 parts by weight and preferably 0.01–5 parts by weight per part by weight of the compound of formula [21t] or salt thereof. The catalysts other than the palladium-carbon and Raney nickel are used in an amount of 0.01–10 mol and preferably 0.01–5 mol per mol of the compound of formula [21t] or salt thereof.

This reaction is carried out usually at −80° C. to 200° C. and preferably at 0° C. to 160° C., for a period of one minute to 48 hours and preferably 5 minutes to 12 hours.

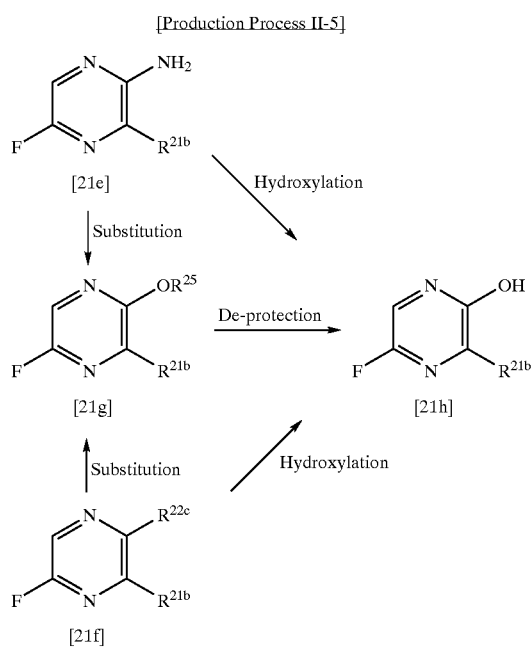

[Production Process II-5]

wherein $R^{22c}$ is as defined above; $R^{21b}$ represents a hydrogen atom, a methyl group, a protected or unprotected hydroxymethyl, aminomethyl or carboxyl group, a methyl group substituted with a protected or unprotected mercapto group, a halogenated methyl group, a formyl group, a protected carbamoyl group, a nitrile group or a halogenated carbonyl group; and $R^{25}$ represents a protecting group for hydroxyl group; provided that a case that $R^{21b}$ is a carbamoyl group protected with an acyl group is excepted.

(5-1)

The compound of general formula [21h] or salt thereof can be obtained by reacting a compound of general formula [21e] or salt thereof with a diazotizing agent and a hydroxylating agent in the presence or absence of an additive, according to the method described in, for example, Shin Jikken Kagaku Koza, Vol. 14, Pages 537–538 (edited by Chemical Society Japan (corporate juridical person), 1977).

The solvent used in this reaction is not limited, unless exercising an adverse influence on the reaction. Examples thereof include inorganic acids such as sulfuric acid, hydrochloric acid, nitric acid and the like; ethers such as dioxane, tetrahydrofuran, anisole, diethylene glycol diethyl ether, dimethyl cellosolve and the like, halogenated hydrocarbons such as dichloromethane, chloroform, dichloroethane and the like; nitriles such as acetonitrile and the like; amides such as N,N-dimethylformamide, N-methyl-2-pyrrolidone and the like; sulfoxides such as dimethyl sulfoxide and the like; amines and amine oxides such as triethylamine, N,N-dimethylaniline, pyridine-N-oxide and the like; ketones such as acetone and the like; water; etc. These solvents may be used as a mixture, if desired.

The diazotizing agent used in this reaction is not particularly limited, so far as it is conventionally used for the deaminating hydroxylation of aromatic amino compounds. Preferable examples thereof include alkali metal nitrites such as sodium nitrite and the like. The diazotizing agent is used at least in an equimolar amount, preferably in an amount of 1.0–5.0 mol and further preferably 1.0–2.0 mol, per mol of the compound of formula [21e] or salt thereof.

As the hydroxylating agent used in this reaction, water and the like can be referred to, for example. The hydroxylating agent is used at least in an equimolar amount to the compound of formula [21e] or salt thereof. It is also possible to use the hydroxylating agent as a solvent.

As the additive used in this reaction, for example, copper salts such as copper sulfate and the like; and inorganic bases such as sodium hydroxide, sodium carbonate and the like can be referred to. The additive is used in an amount of 0.01–100 mol and preferably 0.1–50 mol per mol of the compound of formula [21e] or salt thereof.

This reaction is carried out usually at −70° C. to 200° C. and preferably at −50° C. to 100° C., for a period of one minute to 24 hours and preferably 30 minutes to 10 hours.

(5-2)

The compound of general formula [21h] or salt thereof can be obtained by hydroxylating a compound of general formula [21f] or salt thereof according to the method described in, for example, Shin Jikken Kagaku Koza, Vol. 14, Pages 535–536 (edited by Chemical Society Japan (corporate juridical person), 1977).

The solvent used in this reaction is not particularly limited, unless exercising an adverse influence on the reaction. Examples thereof include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; ketones such as acetone and the like; amides such as N,N-dimethylformamide, N,N-dimethylacetamide and the like; alcohols such as methanol, ethanol, propanol and the like; sulfoxides such as dimethyl sulfoxide and the like; water; etc. These solvents may be used alone or as a mixture of two or more.

The hydroxylating agent used in this reaction is not particularly limited, so far as it is an agent conventionally used for hydroxylation by the nucleophilic substitution of aromatic halogen compounds. Preferable examples thereof include inorganic and organic bases such as sodium hydroxide, lithium hydroxide, sodium hydrogen carbonate, potassium carbonate, potassium hydrogen carbonate, sodium acetate and the like; and inorganic and organic acids such as hydrochloric acid, phosphoric acid, aqueous formic acid, and the like. The hydroxylating agent is used in an amount of at least 0.01 mol and preferably 0.05–20 mol, per mol of the compound of formula [21f] or salt thereof.

This reaction is carried out usually at −78° C. to 180° C. and preferably at −20° C. to 100° C., for a period of one minute to 96 hours and preferably 10 minutes to 72 hours.

(5-3)

The compound of general formula [21g] or salt thereof can be obtained (1) by reacting a compound of general formula [21f] or salt thereof with a nucleophilic substituting agent in the presence or absence of a copper catalyst according to the method described in Shin Jikken Kagaku Koza, Vol. 14, Pages 570–571 (edited by Chemical Society Japan (corporate juridical person), 1977) or (2) by reacting a compound of general formula [21f] or salt thereof with a nucleophilic substituting agent in the presence of a base.

In the method (1), the solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; amides such as N,N-dimethylformamide, N,N-dimethylacetamide and the like; alcohols such as methanol, ethanol, propanol and the like; sulfoxides such as dimethyl sulfoxide and the like; etc. These solvents may be used alone or as a mixture of two or more.

The nucleophilic substituting agent used in this reaction is not particularly limited, so far as it is conventionally used for nucleophilic substitution of aromatic halogen compounds. Preferable examples include alkali metal-$C_{1-6}$ lower alkoxides such as sodium methoxide and the like; alkali metal-ar-$C_{1-6}$ lower alkoxides such as potassium benzyl oxide and the like; and alkali metal salts of organic carboxylic acids such as sodium acetate and the like. If desired, these nucleophilic substituting agents may be synthesized in the reaction system. The nucleophilic substituting agent is used at least in an equimolar amount and preferably in an amount of 1.0–5.0 mol per mol of the compound of [21f] or salt thereof. The copper catalyst which may be used according to the need is not particularly limited, so far as it is a reagent conventionally used for nucleophilic substitution of aromatic halogen compounds. Preferable examples thereof include copper catalysts such as powdered copper, cuprous iodide and the like. The copper catalyst is used in an amount of 0.01–30 mol and preferably 0.05–2 mol, per mol of the compound of formula [21f] or salt thereof.

This reaction is carried out usually at −70° C. to 200° C. and preferably at −20° C. to 50° C., for a period of one minutes to 24 hours and preferably 5 minutes to 6 hours.

In the method (2), the solvents used in the reaction are not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; amides such as N,N-dimethylformamide, N,N-dimethylacetamide and the like; sulfoxides such as dimethyl sulfoxide and the like; etc. These solvents may be used alone or as a mixture of two or more.

The nucleophilic substituting agent used in this reaction is not particularly limited, so far as it is conventionally used for nucleophilic substitution of aromatic halogen compounds. Preferable examples include $C_{1-6}$ lower alcohols such as methanol, ethanol, isopropyl alcohol, allyl alcohol and the like; ar-$C_{1-6}$ lower alcohols such as benzyl alcohol and the like; substituted phenols such as hydroquinone, p-methoxyphenol and the like; alpha-diketones such as 3-methyl-1,2-cyclopentandione and the like; beta-diketones such as 2-methyl-1,3-cyclopentandione and the like; etc. The nucleophilic substituting agent is used at least in an equimolar amount and preferably in an amount of 1.0–5.0 mol per mol of the compound of formula [21f] or salt thereof. The base used in this reaction is not particularly limited, so far as it is conventionally used for nucleophilic substitution of aromatic halogen compounds. Preferable examples thereof include organic bases such as triethylamine, pyridine and the like; and inorganic bases such as sodium carbonate, potassium carbonate and the like. The base is used in an amount of 0.01–30 mol and preferably 0.5–2 mol, per mol of the compound of general formula [21f] or salt thereof.

This reaction is carried out usually at −70° C. to 200° C. and preferably at −20° C. to 100° C., for a period of one minute to 24 hours and preferably 5 minutes to 6 hours.

(5-4)

The compound of general formula [21h] or salt thereof can be obtained by reacting a compound of general formula [21g] or salt thereof with a de-protecting agent in the presence or absence of a catalyst, according to the method described in, for example, Theodora W. Greene: PROTECTIVE GROUPS IN ORGANIC SYNTHESIS, Third Edition, Pages 75 and 249–287 (edited by John Wiley & Sons, Inc., 1999).

The solvent used in this reaction is not particularly limited, unless exercising an adverse influence on the reaction. Examples of the solvent include water; alcohols such as methanol, ethanol, propanol and the like; thio alcohols such as ethanethiol, thio phenol and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; thio ethers such as dimethyl sulfide and the like; ketones such as acetone, methyl ethyl ketone and the like; nitrites such as acetonitrile and the like; amides such as N,N-dimethylformamide, N,N-dimethylacetamide and the like; sulfoxides such as dimethyl sulfoxide and the like; inorganic acids such as sulfuric acid, hydrochloric acid and the like; carboxylic acids such as acetic acid, trifluoroacetic acid and the like; sulfonic acids such as trifluoromethanesulfonic acid and the like; organic bases such as pyridine, triethylamine and the like; water; etc. These solvents may be used alone or as a mixture of two or more.

The de-protecting agent used in this reaction is not particularly limited, so far as it is conventionally used for de-protection of protected aromatic alcohols. Preferable examples thereof include hydrogen gas; Lewis acids such as aluminum, trichloride, boron tribromide, iodine-magnesium complex and the like; inorganic acids such as hydrobromic acid and the like; acidic salts such as pyridine hydrochloride and the like; inorganic bases such as potassium carbonate, sodium hydrogen carbonate, sodium hydroxide and the like; and oxidants such as cerium diammonium nitrate, iron (III) chloride, 2,3-dichloro-5,6-dicyano-1,4-benzoquinone; etc. The de-protecting agent is used in an amount of 0.01–50 mol and preferably 0.1–30 mol per mol of the compound of formula [21g] or salt thereof.

The catalyst which may be used in this reaction according to the need is not particularly limited, so far as it is conventionally used for de-protection of protected aromatic alcohols. Preferable examples thereof include palladium catalysts such as palladium-carbon and the like; rhodium; Raney nickel; platinum (IV) oxide and the like. The palladium-carbon and Raney nickel are used in an amount of 0.001–10 parts by weight and preferably 0.01–5 parts by weight per part by weight of the compound of formula [21g] or salt thereof. The catalysts other than palladium-carbon and Raney nickel are used in an amount of 0.001–10 mol and preferably 0.01–5 mol per mol of the compound of formula [21g] or salt thereof.

This reaction is carried out usually at −80° C. to 200° C. and preferably at 0° C. to 160° C., for a period of one minute to 48 hours and preferably 5 minutes to 12 hours.

(5-5)

The compound of general formula [21g] or salt thereof can be obtained by reacting a compound of general formula [21e] or salt thereof with a diazotizing agent and an alcohol or a sulfonic acid.

The solvent used in this reaction is not particularly limited, unless exercising an adverse influence on the reaction. Examples thereof include inorganic acids such as sulfuric acid, hydrochloric acid, nitric acid and the like; ethers such as dioxane, tetrahydrofuran, anisole, diethylene glycol diethyl ether, dimethyl cellosolve and the like; halogenated hydrocarbons such as dichloromethane, chloroform, dichloroethane and the like; nitriles such as acetonitrile and the like; amides such as N,N-dimethylformamide, N-methyl-2-pyrrolidone and the like; sulfoxides such as dimethyl sulfoxide and the like; amines and amine oxides such as triethylamine, N,N-dimethylaniline, pyridine-N-oxide and the like; ketones such as acetone and the like; alcohols such as methanol, ethanol and the like; water; etc. These solvents may be used as a mixture, if desired.

The diazotizing agent used in this reaction is not particularly limited, so far as it is conventionally used for diazotization of aromatic amino compounds. Preferable examples thereof include alkali metal nitrites such as sodium nitrite and the like. The diazotizing agent is used at least in an equimolar amount and preferably in an amount of 1.0–5.0 mol per mol of the compound of formula [21e] or salt thereof.

As the alcohol used in this reaction, methanol and the like can be referred to, for example. The alcohol is used at least in an equimolar amount to the compound of formula [21e] or salt thereof. The alcohol may be used as a solvent, if desired.

The sulfonic acids used in this reaction include methanesulfonic acid, p-toluenesulfonic acid and the like. The sulfonic acid is used at least in an equimolar amount and preferably in an amount of 1.0–5.0 mol per mol of the compound of formula [21e] or salt thereof. It is also possible to use the sulfonic acid as a solvent, if desired.

This reaction is carried out usually at −70° C. to 200° C. and preferably at −50° C. to 100° C., for a period of one minute to 24 hours and preferably 30 minutes to 10 hours.

[Production Process II-6]

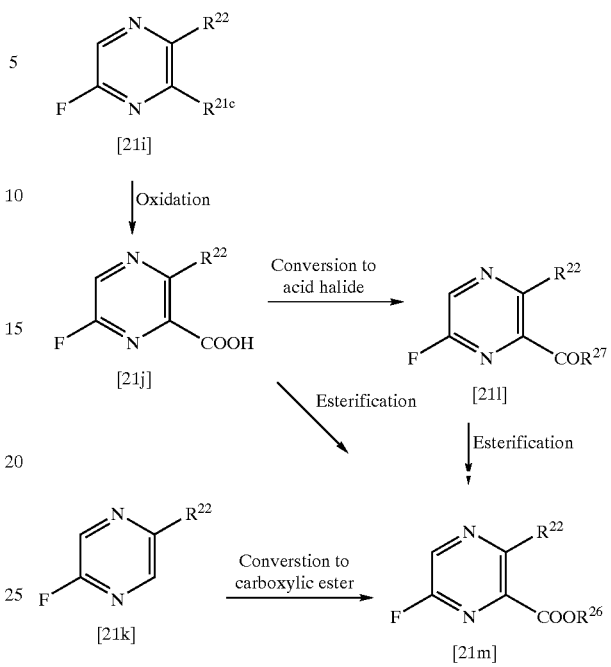

wherein $R^{22}$ is as defined above; $R^{21c}$ represents a methyl group, a protected or unprotected hydroxymethyl or aminomethyl group, a methyl group substituted with a protected or unprotected mercapto group, a halogenated methyl group or a formyl group; $R^{26}$ represents a protecting group for carboxyl group; and $R^{27}$ represents a halogen atom.

(6-1)

The compound of general formula [21j] or salt thereof can be obtained by reacting a compound of [21i] or salt thereof with an oxidant according to the method described in Shin Jikken Kagaku Koza, Vol. 15, Pages 922–926 (edited by Chemical Society Japan (corporate juridical person), 1977) or ibid. Vol. 14, Pages 1051–1053 (edited by Chemical Society Japan (corporate juridical person), 1977).

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; alcohols such as methanol, ethanol, propanol and the like; ketones such as acetone and the like; organic bases such as pyridine and the like; organic acids such as acetic acid and the like; inorganic acids such as nitric acid, sulfuric acid and the like; water; etc. These solvents may be used alone or as a mixture of two or more.

The oxidant used in this reaction is not particularly limited, so far as it is conventionally used as an oxidant for aromatic carboxylic acids. Preferable examples include potassium permanganate, chromium (VI) oxide, sodium dichromate, selenium dioxide, silver oxide, molybdenum (VI) oxide and the like. The oxidant is used in an amount of 0.1–20 mol and preferably 0.5–10 mol per mol of the compound of [21i] or salt thereof.

This reaction is carried out usually at −50° C. to 170° C. and preferably at 0–150° C., for a period of 5 minutes to 72 hours and preferably 30 minutes to 24 hours.

(6-2)

The compound of general formula [21m] or salt thereof can be obtained by esterifying a compound of general formula [21j] or salt thereof according to the method described in Shin Jikken Kagaku Koza, Vol. 14, Pages 1,002–1,016 and 1,106–1,119 (edited by Chemical Society Japan (corporate juridical person), 1977).

Concretely saying, the methods adoptable are (1) dehydrating condensation with an alcohol in the presence or absence of a catalyst or a dehydrating agent, (2) treatment with an alkylating agent, (3) a method of reacting an alkali metal salt or ammonium salt of a compound of general formula [21j] with dialkyl sulfate or alkyl halide, (4) a method of reacting a compound of general formula [21j] or salt thereof with a halogenating agent or the like in the presence or absence of a catalyst to form an active intermediate such as acid halide [21l] or the like, followed by a reaction with an alcohol in the presence or absence of a base, etc.

In the method (1), the solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; alcohols such as methanol, ethanol, propanol and the like; etc. These solvents may be used alone or as a mixture of two or more.

As the catalyst which may be used in this reaction according to the need, for example, inorganic acids such as hydrochloric acid, sulfuric acid and the like; organic acids such as aromatic sulfonic acids and the like; and Lewis acids such as boron trifluoride etherate and the like can be referred to. The catalyst is used in an amount of 0.01–20 mol and preferably 0.01–10 mol per mol of the compound of formula [21j] or salt thereof.

As the dehydrating agent which may be used in this reaction according to the need, for example, carbodiimides such as dicyclohexyl carbodiimide, diisopropyl carbodiimide and the like can be referred to. The dehydrating agent is used at least in an equimolar amount and preferably in an amount of 1–20 mol, per mol of the compound of formula [21j] or salt thereof.

This reaction is carried out usually at −20° C. to 200° C. and preferably at 0–180° C., for a period of 5 minutes to 10 days and preferably 30 minutes to 6 days.

In the method (2), the solvent used in this reaction is not particularly limited, unless exercising an adverse influence on the reaction. Examples of the solvent include ethers such as diethyl ether, dioxane, tetrahydrofuran and the like; aromatic hydrocarbons such as benzene, toluene and the like; ortho esters such as triethyl orthoformate and the like; etc. These solvents may be used alone or as a mixture of two or more.

As the alkylating agent used in this reaction, for example, diazo compounds such as diazomethane and the like, ortho esters such as triethyl orthoformate and the like, etc. can be referred to. The alkylating agent is used at least in an equimolar amount and preferably in an amount of 1–20 mol per mol of the compound of formula [21j] or salt thereof.

This reaction is carried out usually at −20° C. to 200° C. and preferably at 0–180° C., for a period of 5 minutes to 72 hours and preferably 30 minutes to 48 hours.

In the method (3), the solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; ethers such as dioxane, tetrahydrofuran, anisole, diethylene glycol diethyl ether, dimethyl cellosolve and the like; alcohols such as methanol, ethanol, propanol and the like; ketones such as acetone and the like; amides such as N,N-dimethylformamide and the like; etc. These solvents may be used alone or as a mixture of two or more.

As the alkali metal salts used in this reaction, for example, sodium salts and potassium salts can be referred to. As ammonium salt, for example, organic base salts such as tetramethylammonium salts and the like can be referred to. These salts may be generated in the reaction system, if desired.

As the dialkyl sulfate used in this reaction, for example, dialkyl sulfates such as dimethyl sulfate, diethyl sulfate and the like can be referred to. As the alkyl halide used in this reaction, for example, alkyl halides such as methyl iodide, ethyl iodide and the like can be referred to. The dialkyl sulfate and alkyl halide are used at least in an equimolar amount and preferably in an amount of 1–20 mol per mol of the compound of general formula [21j] or salt thereof.

This reaction is carried out usually at −20° C. to 250° C. and preferably 0–180° C., for a period of 5 minutes to 72 hours and preferably 30 minutes to 48 hours.

In the method (4) the solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; ethers such as dioxane, tetrahydrofuran, anisole, diethylene glycol diethyl ether, dimethyl cellosolve and the like; ketones such as acetone and the like; etc. These solvents may be used alone or as a mixture of two or more.

As the halogenating agent used in this reaction, inorganic halogen compounds such as thionyl chloride, phosphorus pentachloride, phosphorus trichloride, phosphoryl chloride and the like; oxalic acid halides such as oxalyl chloride, oxalyl bromide and the like; etc. can be referred to. The halogenating agent is used in this reaction at least in an equimolar amount and preferably in an amount of 1–10 mol per mol of the compound of formula [21j] or salt thereof.

As the catalyst which may be used in this reaction according to the need, organic bases such as triethylamine, pyridine and the like; Lewis acids such as zinc chloride and the like; iodine; N,N-dimethylformamide; etc. can be referred to. The catalyst is used in an amount of 0.001–10 mol and preferably 0.001–0.5 mol per mol of the compound of formula [21j] or salt thereof.

As the base used in this reaction, organic and inorganic bases such as pyridine, dimethylaniline, metallic magnesium and the like can be referred to. The base is used at least in an equimolar amount and preferably in an amount of 1–10 mol per mol of the compound of formula [21j] or salt thereof.

This reaction is carried out usually at −20° C. to 200° C. and preferably at −10° C. to 120° C., for a period of one minute to 72 hours and preferably 10 minutes to 24 hours.

(6-3)

The compound of general formula [21m] or salt thereof can be obtained by reacting a compound of general formula [21k] or salt thereof with an ester in the presence or absence of a catalyst according to the method described in, for example, Collect. Czech. Chem. Commun., Vol. 54, No. 5, Pages 1,306–1,310 (1989).

The solvent used in this reaction is not particularly limited, unless exercising an adverse influence on the reaction. Examples of the solvent include sulfuric acid, water, and the like. These solvents may be used alone or as a mixture of two or more.

As the ester used in this reaction, for example, esters such as methyl pyruvate, ethyl pyruvate and the like can be referred to. The ester is used in an amount of 0.1–10 mol and preferably 0.2–5 mol per mol of the compound of formula [21k] or salt thereof.

As the catalyst used in this reaction according to the need, for example, copper sulfate, aqueous hydrogen peroxide and the like can be referred to. The catalyst is used in an amount of 0.01–10 mol and preferably 0.1–5 mol per mol of the compound of formula [21k] or salt thereof.

This reaction is carried out usually at −50° C. to 150° C. and preferably at −20° C. to 100° C., for a period of 5 minutes to 72 hours and preferably 30 minutes to 24 hours.

dimethylformamide and the like; water; etc. These solvents may be used alone or as a mixture of two or more. As the catalyst used in the reaction (1) according to the need, for example, activated alumina, organic acids such as aromatic sulfonic acids, etc. can be referred to. The catalyst is used in an amount of 0.01–20 mol and preferably 0.1–10 mol per mol of the compound of formula [21n] or salt thereof. As the dehydrating agent used in the reaction (1), for example, carbodiimides such as dicyclohexyl carbodiimide, diisopropyl carbodiimide and the like can be referred to. As the amidating agent used in the reaction (2), for example,

[ProductionProcess II-7]

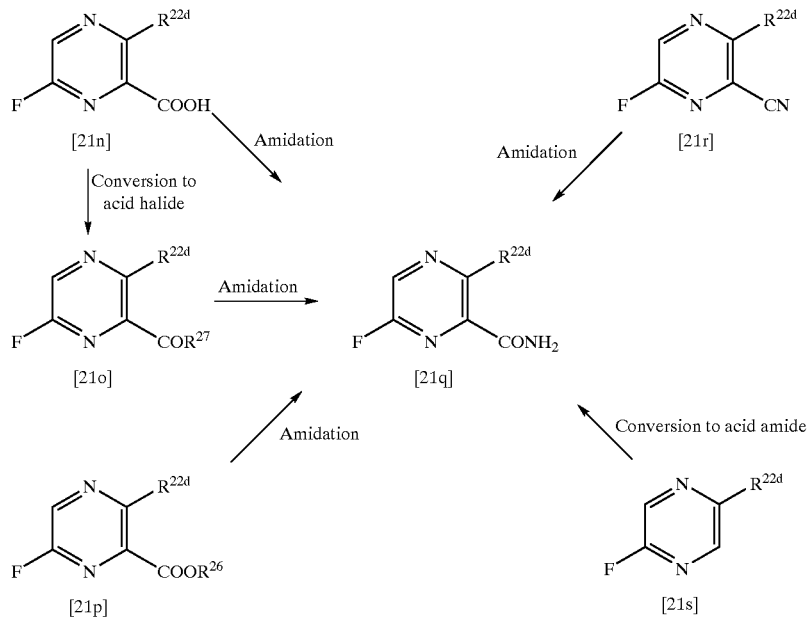

wherein $R^{26}$ and $R^{27}$ are as defined above; and $R^{22d}$ represents a protected hydroxyl group, a protected or unprotected amino group, a halogen atom, a nitro group or an azido group.

(7-1)

The compound of general formula [21q] or salt thereof can be obtained by amidating a compound of general formula [21n] or salt thereof according to the method described in Shin Jikken Kagaku Koza, Vol. 14, Pages 1,106–1,119 and 1,136–1,147 (edited by Chemical Society Japan (corporate juridical person), 1977).

Concretely saying, the methods adoptable include (1) dehydration of compound [21n] or salt thereof with ammonia in the presence or absence of a catalyst or a dehydrating agent, (2) a method of reacting compound [21 n] or salt thereof with an amidating agent, (3) a method of reacting compound [21n] or salt thereof with a halogen compound to form an active intermediate such as an acid halide compound [21o] or the like, followed by a reaction with ammonia, etc.

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride and the like; ethers such as dioxane, tetrahydrofuran, anisole, diethylene glycol diethyl ether, dimethyl cellosolve and the like; ketones such as acetone and the like; amides such as N,N- amidating agents such as urea and the like can be referred to. As the halogen compound used in the reaction (3), for example, halogenating agents such as oxalyl chloride, thionyl chloride and the like can be referred to. In these reactions, the dehydrating agent, amidating agent and halogen compound are used at least in an equimolar amount and preferably in an amount of 1–20 mol per mol of the compound of formula [21n] or salt thereof.

These reactions are carried out usually at −20° C. to 200° C. and preferably at 0–180° C., for a period of 5 minutes to 72 hours and preferably 30 minutes to 48 hours.

(7-2)

The compound of general formula [21q] or salt thereof can be obtained by subjecting a compound of general formula [21p] or salt thereof to an ammonolysis reaction of carboxylic ester in the presence or absence of a catalyst according to the method described in, for example, Shin Jikken Kagaku Koza, Vol. 14, Pages 1,147–1,151 (edited by Chemical Society Japan (corporate juridical person), 1977).

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; nitriles such as acetonitrile and the like; amides such as N,N-dimethylformamide, N,N-dimethylacetamide and the like; alcohols such as methanol, ethanol, propanol and the like;

sulfoxides such as dimethyl sulfoxide and the like; water; etc. These solvents may be used alone or as a mixture of two or more. Although this reaction may be carried out under the conventionally used conditions for ammonolysis of aromatic carboxylic esters, a method of using gaseous ammonia, liquid ammonia or aqueous ammonia is preferable. As the catalyst used in this reaction according to the need, ammonium salts of acids such as ammonium chloride and the like; bases such as sodium methoxide, butyllithium and the like; alkali metal amides such as sodium amide and the like; etc. can be referred to. The catalyst is used in an amount of 0.01–100 mol and preferably 0.01–20 mol, per mol of the compound of formula [21p] or salt thereof.

This reaction is carried out usually at −100° C. to 250° C. and preferably at −78° C. to 100° C., for a period of one minute to 72 hours and preferably 30 minutes to 50 hours.

(7-3)

The compound of general formula [21q] or salt thereof can be obtained by amidating a compound of general formula [21r] or salt thereof either (1) under an acidic condition, (2) under a basic condition in the presence or absence of a peracid, or (3) under a neutral condition, according to the method described in Shin Jikken Kagaku Koza, Vol. 14, Pages 1,151–1,154 (edited by Chemical Society Japan (corporate juridical person), 1977).

In the method (1), the solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; inorganic acids such as hydrochloric acid, sulfuric acid, polyphosphoric acid and the like; organic acids such as acetic acid, formic acid and the like; water; etc. These solvents may be used alone or as a mixture of two or more.

As the acid used in this reaction, for example, inorganic acids such as hydrochloric acid, sulfuric acid, polyphosphoric acid and the like; organic acids saturated with a Lewis acid such as hydrogen chloride, hydrogen bromide, boron trifluoride and the like; etc. can be referred to. The acid is used in an amount of 0.1–100 mL and preferably 0.5–50 mL per gram of the compound of formula [21r] or salt thereof, as expressed in terms of volume/weight ratio (mL/g). If desired, these acids may be used as a solvent.

This reaction is carried out usually at 0–200° C. and preferably 0–160° C., for a period of one minute to 72 hours and preferably 5 minutes to 48 hours.

In the method (2), the solvent used in this reaction is not particularly limited unless exercising an adverse influence on the reaction. Examples of the solvent include alcohols such as methanol, ethanol, propanol and the like; sulfoxides such as dimethyl sulfoxide and the like; esters such as ethyl acetate and the like; water; etc. These solvents may be used alone or as a mixture of two or more.

The base used in this reaction is not particularly limited, so far as it is conventionally used for carbamoylation of aromatic nitrites. Preferable examples thereof include alkali metal bases such as sodium hydroxide and the like and aqueous solutions of amines such as aqueous ammonia and the like. The base is used in an amount of 0.1–20 mol and preferably 0.5–10 mol per mol of the compound of formula [21r] or salt thereof.

As the peracid used in this reaction, hydrogen peroxide and the like can be referred to. The peracid is used in an amount of 0.1–20 mol and preferably 0.5–10 mol per mol of the compound of formula [21r] or salt thereof.

This reaction is carried out usually at −20° C. to 170° C. and preferably at 0–160° C. for a period of one minute to 72 hours and preferably 5 minutes to 48 hours.

In the method (3), the solvent used in this reaction is not particularly limited, unless exercising an adverse influence on the reaction. Examples of the solvent include halogenated hydrocarbons such as methylene chloride and the like; ethers such as dioxane, tetrahydrofuran, anisole, diethylene glycol diethyl ether, dimethyl cellosolve and the like; nitrites such as acetonitrile and the like; water; etc. These solvents may be used alone or as a mixture of two or more.

The reagent used in this reaction is not particularly limited, so far as it is a reagent conventionally used in the carbamoylation of aromatic nitrites. Preferable examples thereof include manganese dioxide and the like. The reagent is used at least in an equimolar amount and preferably in an amount of 1–100 mol per mol of the compound of formula [21r] or salt thereof.

This reaction is carried out usually at −20° C. to 170° C. and preferably at 0–160° C., for a period of 5 minutes to 72 hours and preferably 30 minutes to 48 hours.

(7-4)

The compound of general formula [21q] or salt thereof can be obtained by reacting a compound of general formula [21s] or salt thereof with an amide in the presence or absence of a catalyst, according to the method described in, for example, Collect. Czech. Chem. Commun., Vol. 54, No. 5, Pages 1,306–1,310 (1989).

The solvent used in this reaction is not particularly limited, unless exercising an adverse influence on the reaction. Examples of the solvent include sulfuric acid, water, etc. These solvents may be used alone or as a mixture of two or more.

As the amide used in this reaction, for example, formamides and the like can be referred to. The amide is used in an amount of 0.1–100 mol and preferably 0.2–50 mol, per mol of the compound of general formula [21s] or salt thereof.

As the catalyst which may be used in this reaction according to the need, for example, copper sulfate, aqueous hydrogen peroxide and the like can be referred to. The catalyst is used in an amount of 0.01–10 mol and preferably 0.1–5 mol, per mol of the compound of formula [21s] or salt thereof.

This reaction is carried out usually at −50° C. to 150° C. and preferably at −20° C. to 100° C., for a period of 5 minutes to 72 hours and preferably 30 minutes to 24 hours.

[Production Process II-8]

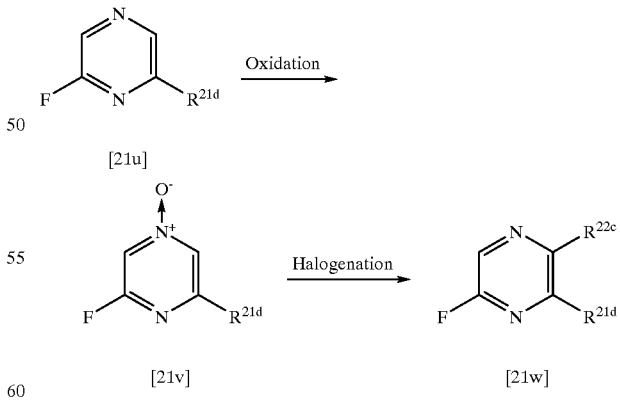

wherein $R^{22c}$ is as defined above; and $R^{21d}$ represents a methyl group, a protected or unprotected hydroxymethyl, aminomethyl, carbamoyl or carboxyl group, a methyl group substituted with a protected or unprotected mercapto group, a halogeno-methyl group, a formyl group, a nitrile group or a halogenated carbonyl group.

(8-1)

The compound of general formula [21v] or salt thereof can be obtained by reacting a compound of general formula [21u] or salt thereof with an oxidant in the presence or absence of a catalyst, according to the method described in, for example, Jikken Kagaku Koza, Fourth Edition, Vol. 23, (edited by Chemical Society Japan (corporate juridical person), 1991).

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; ketones such as acetone and the like; amides such as N,N-dimethylformamide, N,N-dimethylacetamide and the like; alcohols such as methanol, ethanol, propanol and the like; nitrites such as acetonitrile, benzonitrile and the like; organic acids such as acetic acid, trifluoroacetic acid and the like; water; etc. These solvents may be used alone or as a mixture of two or more.

The oxidant used in this reaction is not particularly limited, so far as it is conventionally used for oxidation of tertiary amines. Preferable examples thereof include inorganic peracids such as hydrogen peroxide and the like; organic peracids such as m-chloroperbenzoic acid, peracetic acid, per-trifluoroacetic acid and the like; dioxysilanes such as dimethyldioxysilane and the like; peroxides such as potassium peroxodisulfate, sodium peroxoborate and the like; ozone; gaseous oxygen; etc. These oxidants may be synthesized in the reaction system, if desired. The oxidant is used in an amount of 0.01–10 mol and preferably 1.0–5.0 mol per mol of the compound of formula [21u] or salt thereof.

As the catalyst which may be used in this reaction according to the need, for example, molybdenum oxide, iron (III) oxide and the like can be referred to. The catalyst is used in an amount of 0.01–100 parts by weight and preferably 0.1–10 parts by weight per part by weight of the compound of formula [21u] or salt thereof.

This reaction is carried out usually at −78° C. to 200° C. and preferably at 0–150° C., for a period of one minute to 24 hours and preferably 30 minutes to 8 hours.

(8-2)

The compound of general formula [21w] or salt thereof can be obtained by reacting a compound of general formula [21v] or salt hereof with a halogenating agent according to the method described in Heterokan Kagoubutsu no Kagaku, Pages 177–201 (edited by Kodansha Scientific, 1988).

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; ethers such as dioxane, tetrahydrofuran, anisole, diethylene glycol diethyl ether, dimethyl cellosolve and the like; amides such as N,N-dimethylformamide, N,N-dimethylacetamide and the like; etc. These solvents may be used alone or as a mixture of two or more.

The reagent used in this reaction is not limited, so far as it is a halogenating agent. Preferable examples of the halogenating agent include phosphorus oxychloride, thionyl chloride and the like. The halogenating agent is used in an amount of 0.3–100 mol and preferably 1–30 mol per mol of the compound of general formula [21v] or salt thereof.

The reaction is carried out usually at −20° C. to 200° C. and preferably at 0–120° C., for a period of one minute to 24 hours and preferably 30 minutes to 6 hours.

[Production Process II-9]

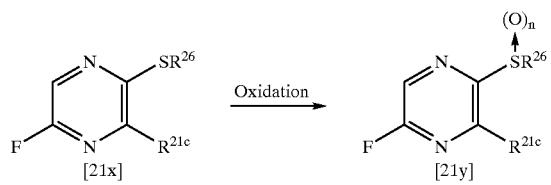

wherein $R^{21c}$ is as defined above; $R^{26}$ represents a substituted or unsubstituted phenyl group; and n represents 1 or 2.

The compound of general formula [21y] or salt thereof can be obtained by reacting a compound of general formula [21x] or salt thereof with an oxidant according to the method described in Shin Jikken Kagaku Koza, Vol. 14, Pages 1,749–1,756 and 1,759–1,763 (edited by Chemical Society Japan (corporate juridical person), 1978).

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; ketones such as acetone and the like; amides such as N,N-dimethylformamide, N,N-dimethylacetamide and the like; alcohols such as methanol, ethanol, propanol and the like; nitriles such as acetonitrile, benzonitrile and the like; organic acids such as acetic acid, trifluoroacetic acid and the like; organic bases such as pyridine, quinoline and the like; water; etc. These solvents may be used alone or as a mixture of two or more.

The oxidant used in this reaction is not particularly limited, so far as it is a reagent conventionally used in the oxidation of sulfides. Preferable examples thereof include peracids such as hydrogen peroxide, peracetic acid, perbenzoic acid, m-chloroperbenzoic acid and the like; sodium metaperiodate, hydroperoxides, ozone, selenium dioxide, chromic acid, dinitrogen tetraoxide, acyl nitrate, iodine, bromine, N-bromosuccinimide, iodosylbenzene, sulfuryl chloride plus hydrated silica gel, tert-butyl hypochlorite, ruthenium oxide, osmium (VIII) oxide and the like. These oxidants may be synthesized in the reaction system if desired. These oxidants are used in an amount of 0.01–10 mol and preferably 1.0–5.0 mol per moll of the compound of general formula [21x] or salt thereof. This reaction is carried out usually at −78° C. to 200° C. and preferably at 0–150° C., for a period of one minute to 24 hours and preferably 30 minutes to 8 hours.

Next, the methods for synthesizing the compounds of general formulas [25] and [27] or salts thereof used in Production Processes II-1 and II-2 will be described.

[Production Process II-A]

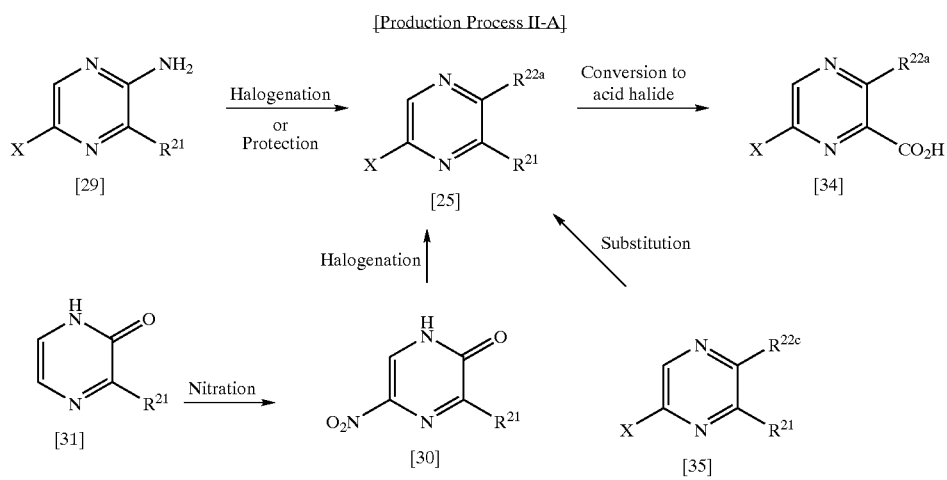

wherein $R^{21}$, $R^{22a}$, $R^{22c}$ and X are as defined above.

(A-1)

The compound of general formula [25] or salt thereof can be obtained (1) by de-aminating the amino group of a compound of general formula [29] or salt thereof with a diazotizing agent in the presence of an additive according to the method described in Shin Jikken Kagaku Koza, Vol. 14, Pages 383–387 (edited by Chemical Society Japan (corporate juridical person), 1977), followed by subjecting the de-aminated product to halogenation, or (2) by reacting a compound of general formula [29] or salt thereof with a protecting agent in the presence or absence of an additive according to the method described in Theodora W. Greene: PROTECTIVE GROUPS IN ORGANIC SYNTHESIS, Third Edition, Pages 503–615 (1999).

In the method (1), the solvent used in this reaction is not particularly limited, unless exercising an adverse influence on the reaction. Examples of the solvent include inorganic acids such as sulfuric acid, hydrochloric acid, hydrobromic acid, nitric acid and the like; ethers such as dioxane, tetrahydrofuran, anisole, diethylene glycol diethyl ether, dimethyl cellosolve and the like; halogenated hydrocarbons such as dichloromethane, chloroform, dichloroethane and the like; nitriles such as acetonitrile and the like; amides such as N,N-dimethylacetamide, N-methyl-2-pyrrolidone and the like; sulfoxides such as dimethyl sulfoxide and the like; amines and amine oxides such as triethylamine, N,N-dimethylaniline, pyridine-N-oxide and the like; ketones such as acetone and the like; water; etc. These solvents may be used as a mixture, if desired.

The diazotizing agent used in this reaction is not particularly limited, so far as it is a reagent conventionally used for diazotization of aromatic amino compounds. Preferable examples thereof include alkali metal nitrites such as sodium nitrite and the like. The diazotizing agent is used at least in an equimolar amount, preferably in an amount of 1.0–5.0 mol, and further preferably 1.0–2.0 mol, per mol of the compound of formula [29] or salt thereof.

As the additive used in this reaction, for example, copper salts such as cuprous chloride, cuprous bromide and the like; iron salts such as iron chloride, iron bromide and the like; etc. can be referred to. The additive is used in an amount of 0.01–100 mol and preferably 1–50 mol, per mol of the compound of formula [29] or salt thereof.

This reaction is carried out usually at −70° C. to 200° C. and preferably −50° C. to 100° C., for a period of one minute to 24 hours and preferably 30 minutes to 10 hours.

In the method (2), the solvent used in this reaction is not particularly limited, unless exercising an adverse influence on the reaction. Examples of the solvent include water; alcohols such as methanol, ethanol, propanol and the like; aliphatic hydrocarbons such as n-hexane and the like; aromatic hydrocarbons such as benzene, toluene, xylene and the like; halogenated hydrocarbons such as methylene chloride, chloroform, dichloroethane and the like; ethers such as dioxane, tetrahydrofuran, anisole, diethylene glycol diethyl ether, dimethyl cellosolve and the like; thio ethers such as dimethyl sulfide and the like; ketones such as acetone, methyl ethyl ketone and the like; nitrites such as acetonitrile and the like; amides such as N,N-dimethylformamide, N,N-dimethylacetamide and the like; sulfoxides such as dimethyl sulfoxide and the like; acetals such as N,N-dimethylformamide dimethyl acetal and the like; inorganic acids such as sulfuric acid, hydrochloric acid and the like; carboxylic acids such as acetic acid, trifluoroacetic acid and the like; organic bases such as pyridine, triethylamine and the like; water; etc. These solvents may be used alone or as a mixture of two or more.

The protecting agent used in this reaction is not particularly limited, so far as it is a reagent conventionally used for protection of aromatic amino compounds. Preferable examples thereof include organic halogen compounds such as benzoyl chloride, benzyl chloroformate, trityl chloride and the like; organic acid anhydrides such as acetic anhydride, di-tert-butyl dicarbonate and the like; aldehydes such as benzaldehyde and the like; acetals such as N,N-dimethylformamide dimethyl acetal and the like; etc. The protecting agent is used at least in an equimolar amount and preferably in an amount of 1.0–5.0 mol and further preferably 1.0–3.0 mol, per mol of the compound of formula [29] or salt thereof, except for a case where the protecting agent is used as a solvent as in the case of N,N-dimethylformamide dimethyl acetal.

As the additive used in this reaction, for example, inorganic bases such as sodium hydrogen carbonate, sodium hydride, sodium hydroxide and the like; carboxylic acid salts such as sodium acetate and the like; organic bases such as pyridine, triethylamine and the like; organolithium compounds such as n-butyllithium and the like; organo-silicon compounds such as trimethylsilyl chloride and the like; alkali metal salts such as sodium sulfate and the like; ortho acids such as ethyl orthoformate and the like; organic acids such as acetic acid, p-toluenesulfonic acid, N-hydroxysuccinimide and the like; inorganic acids such as hydrochloric acid, tetrafluoroboric acid and the like; alkali metals such as sodium and the like; carbodiimides such as N,N'-dicyclohexyl carbodiimide and the like; N,N'-carbonyl diimidazole and the like; crown ethers such as 18-crown-6 and the like; ammonium salts such as tetra-n-butylammonium iodide and the like; copper salts such as copper chloride and the like; palladium salts such as palladium chloride and the like; etc. The additive is used in an amount of 0.01–100 mol and preferably 1–50 mol per mol of the compound of formula [29] or salt thereof.

This reaction is carried out usually at –70° C. to 200° C. and preferably at –50° C. to 160° C., for a period of one minute to 24 hours and preferably 10 minutes to 10 hours.

The compound of general formula [29] or salt thereof which is a starting compound of the above-mentioned reaction can be produced according to the method described in, for example, J. Med. Chem., Vol. 8, Pages 638–642 (1965).

(A-2)

The compound of general formula [25] or salt thereof can be obtained by halogenating a compound of general formula [30] in the presence or absence of an additive.

The solvent used in this reaction is not particularly limited, unless exercising an adverse influence on the reaction. Examples of the solvent include aromatic hydrocarbons such as toluene and the like; ethers such as tetrahydrofuran and the like; etc. These solvents may be used as a mixture, if desired.

The halogenating agent used in this reaction is not particularly limited, so far as it is a conventional halogenating agent. Examples thereof include phosphorus halogenides such as phosphorus oxychloride, phosphorus oxybromide, phosphorus pentachloride, dichlorotriphenylphosphorane and the like; compounds having a halide ion such as phosgene, thionyl chloride, benzenesulfonyl chloride and the like; etc. If desired, these reagents may be used as a mixture. Although the amount of the halogenating agent varies depending on the kind of halogenating agent, it is used at least in an equimolar amount to the compound of general formula [30] or salt thereof. If desired, the halogenating agent may be used as a solvent. For example, when phosphorus oxychloride is used, it may be used as a solvent, and its amount may be 2.0–100 mol and preferably 2.0–30 mol per mol of the compound of formula [30] or salt thereof.

As the additive which may be used in this reaction according to the need, for example, bases such as pyridine, N,N-diethylaniline and the like can be referred to. Although the amount of the additive varies depending on the kind of additive, it may be used in an amount of 0.1–30 mol and preferably 1.0–10 mol per mol of the compound of formula [30] or salt thereof.

This reaction is carried out usually at 0–300° C. and preferably at 20–120° C., for a period of 30 minutes to 48 hours and preferably one hour to 24 hours.

The compound of general formula [30] or salt thereof can be obtained by reacting a compound of general formula [31] or salt thereof with a nitrating agent according to the method described in, for example, Shin Jikken Kagaku Koza, Vol. 14(III), Pages 1,266–1,277 (edited by Chemical Society Japan (corporate juridical person), 1978).

The solvent used in this reaction is not particularly limited, unless exercising an adverse influence on the reaction. Examples of the solvent include inorganic acids such as sulfuric acid, hydrochloric acid, phosphoric acid and the like; aliphatic carboxylic acids such as acetic acid and the like and acid anhydrides; ethers such as diethyl ether and the like; halogenated hydrocarbons such as methylene chloride and the like; water; etc. These solvents may be used as a mixture, if desired. As the nitrating agent used in this reaction, for example, inorganic acids such as nitric acid; alkali metal nitrates such as potassium nitrate and the like; nitronium salts such as nitronium tetrafluoroborate, nitronium trifluoromethanesulfonate and the like; etc. can be referred to. These reagents may be used as a mixture, if desired.

Although the amount of the nitrating agent used in this reaction varies depending on the kind of nitrating agent, it may be used at least in an equimolar amount to the compound of general formula [31] or salt thereof, and preferably in an amount of 1.0–10 mol and further preferably 1.0–3.0 mol per mol of the compound of formula [31] or salt thereof.

This reaction is carried out usually at –60° C. to 200° C. and preferably at 0–100° C., for a period of 10 minutes to 48 hours and preferably one hour to 24 hours.

(A-3)

The compound of general formula [25] or salt thereof can be obtained by reacting a compound of general formula [34] or salt thereof with a halogenating agent in the presence or absence of a catalyst according to the method described in, for example, Shin Jikken Kagaku Koza, Vol.14, Pages 1,106–1,119 (edited by Chemical Society Japan (corporate juridical person), 1977).

The solvent used in this reaction is not particularly limited, unless exercising an adverse influence on the reaction. Examples of the solvent include aromatic hydrocarbons such as benzene, toluene, xylene and the like; halogenated hydrocarbons such as methylene chloride, chloroform and the like; ethers such as dioxane, tetrahydrofuran, anisole, diethylene glycol diethyl ether, dimethyl cellosolve and the like; ketones such as acetone and the like; etc. These solvents may be used alone or as a mixture of two or more.

The halogenating agent used in this reaction is not particularly limited, so far as it is a conventional halogenating agent. Examples thereof include inorganic halogen compounds such as thionyl chloride, phosphorus pentachloride, phosphorus trichloride, phosphoryl chloride and the like; oxalic acid halides such as oxalyl chloride, oxalyl bromide and the like; etc. The halogenating agent is used at least in an equimolar amount and preferably in an amount of 1–10 mol per mol of the compound of formula [34] or salt thereof.

As the catalyst which may be used in this reaction according to the need, for example, organic bases such as triethylamine, pyridine and the like; Lewis acids such as zinc chloride and the like; iodine; N,N-dimethylformamide; etc. can be referred to. The catalyst is used in an amount of 0.001–10 mol and preferably 0.001–0.5 mol per mol of the compound of formula [34] or salt thereof.

This reaction is carried out usually at –20° C. to 200° C. and preferably at –10° C. to 120° C., for a period of one minute to 72 hours and preferably 10 minutes to 24 hours.

(A-4)

The compound of general formula [25] or salt thereof can be obtained by reacting a compound of general formula [35] or salt thereof with a nucleophilic substituting agent in the presence of a base.

The solvent used in this reaction is not particularly limited, unless exercising an adverse influence on the reaction. Examples of the solvent include aromatic hydrocarbons such as benzene, toluene, xylene and the like; ethers such as dioxane, tetrahydrofuran, anisole, diethylene glycol diethyl ether, dimethyl cellosolve and the like; amides such as N,N-dimethylformamide, N,N-dimethylacetamide and the like; sulfoxides such as dimethyl sulfoxide and the like; etc.

These solvents may be used alone or as a mixture of two or more.

The nucleophilic substituting agent used in this reaction is not particularly limited, so far as it is a reagent conventionally used in a nucleophilic substitution of aromatic halogen compounds. Preferable examples thereof include substituted phenols such as hydroquinone, p-methoxyphenol and the like; aryl mercaptans such as thiophenol and the like; etc. The nucleophilic substituting agent is used at least in an equimolar amount and preferably in an amount of 1.0–5.0 mol per mol of the compound of formula [35] or salt thereof. The base used in this reaction is not particularly limited so far as it is a reagent conventionally used in the nucleophilic substitution of aromatic halogen compounds. Preferable examples thereof include organic bases such as triethylamine, pyridine and the like; and inorganic bases such as sodium carbonate, potassium carbonate and the like. The base is used in an amount of 0.01–30 mol and preferably 0.5–2 mol per mol of the compound of formula [35] or salt thereof.

This reaction is carried out usually at −70° C. to 200° C. and preferably −20° C. to 50° C., for a period of one minute to 24 hours and preferably 5 minutes to 6 hours.

[Production Process II-B]

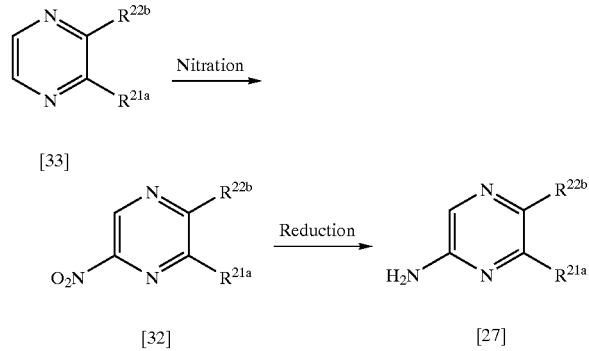

wherein $R^{21a}$ and $R^{22b}$ are as defined above.

(B-1)

The compound of general formula [27] or salt thereof can be obtained by subjecting a compound of general formula [32] or salt thereof to the same reaction as mentioned in Production Process II-4-1.

(B-2)

The compound of general formula [32] or salt thereof can be obtained by subjecting a compound of general formula [33] or salt thereof to the same reaction as mentioned in Production Process II-A-2.

Next, a method for producing the compound of general formula [23] by using a compound of general formula [21] or salt thereof as a starting compound will be described below.

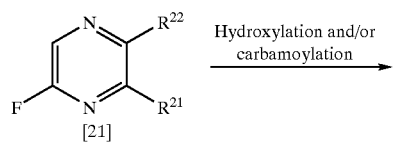 Hydroxylation and/or carbamoylation →

-continued

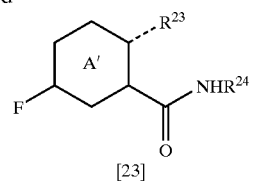

wherein A', $R^{21}$, $R^{22}$, $R^{23}$, $R^{24}$ and the broken line are as defined above; provided that a case that $R^{21}$ is a carbamoyl group or a carbamoyl group substituted with an acyl group and $R^{22}$ is a hydroxyl group is excepted.

The compound of general formula [23] or salt thereof can be produced by subjecting a compound of general formula [21] or salt thereof to a hydroxylation reaction and/or a carbamoylation reaction.

In this reaction, the hydroxylation can be carried out by subjecting a compound of formula [21] or salt thereof to a method well known in itself such as the reduction, substitution, Sandmeyer reaction, hydrolysis and/or de-protecting reaction, etc. mentioned in Production Processes II-4-1, II-4-2, II-4-3, II-4-4, II-5-1, II-5-1, II-5-3, II-4, etc., or by combining these methods appropriately.

In this reaction, the carbamoylation can be carried out by subjecting a compound of formula [21] or salt thereof to a reaction well known in itself such as the oxidation, reduction, substitution, addition, halogenation, dehydration and/or hydrolysis, etc. mentioned in Production Processes II-6-1, II-6-2, II-6-3, II-7-1, II-7-2, II-7-3, II-7-4, etc., or by combining these reactions appropriately.

In a case where both the hydroxylation and carbamoylation are carried out in these reactions, any of the hydroxylation and carbamoylation may be carried out in advance of the other.

As the salt of the compounds of formulas [21] to [35] in the above-mentioned methods for producing intermediate compounds, usually known salts at the site of basic group such as amino group and those at the site of acidic group such as hydroxyl group, carboxyl group and the like can be referred to. As the salt at the site of basic group, for example, salts formed with an inorganic acid such as hydrochloric acid, hydrobromic acid, sulfuric acid and the like; salts formed with an organic carboxylic acid such as tartaric acid, formic acid, citric acid, trichloroacetic acid, trifluoroacetic acid and the like; and salts formed with a sulfonic acid such as methanesulfonic acid, benzenesulfonic acid, p-toluenesulfonic acid, mesitylenesulfonic acid, naphthalenesulfonic acid and the like can be referred to. As the salt at the site of acidic group, for example, salts formed with an alkali metal such as sodium, potassium and the like; salts formed with an alkaline earth metal such as calcium, magnesium and the like; ammonium salts; and salts formed with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like can be referred to.

Further, in the production processes described above, salts of the compounds of general formulas [21] to [35] may be used in stead of the compounds of formulas [21] to [35], and as the salts, the same salts as mentioned above can be used.

In some cases, the compounds of general formulas [21] to [35] and salts thereof may have isomers such as tautomers, optical isomers, position isomers, etc. and solvated products.

In such cases, all those isomers and solvated products can be used in the present invention. After completion of the reaction, the objective compound of the reaction may be used in the next step of the process as it is, without isolation.

Particularly, in the compound of general formula [21] wherein $R^{22}$ is OH, there exist the following keto and enol forms of tautomers, and these tautomers are the same compound substantially.

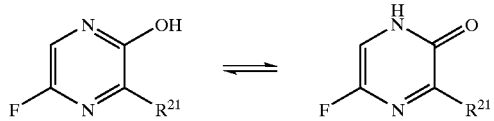

In the production processes mentioned above, the compounds of general formulas {21]–[35] or salts thereof may have an amino group, a carbamoyl group, a hydroxyl group, a mercapto group or a carboxyl group. In such cases, it is possible to protect these groups with a conventional protecting group previously, and after the reaction, to eliminate the protecting group according to the method well known in itself.

Next, the antiviral and cytotoxic activities of the pyrazine derivatives represented by general formula [1] of the present invention or salts thereof will be described.

Sample: A pyrazine derivative represented by general formula [1] or salt thereof was dissolved in dimethyl sulfoxide to prepare a solution having a concentration of 10 mg/mL. At the time of use, the solution was diluted to a desired concentration with a culture medium and put to use.

Culture medium: A 10% fetal bovine serum-added E'-MEM was used at the time of multiplying the cells of MDCK (originated from dog kidney), MA-104 (originated from monkey kidney) and HEp-2 (originated from human pharyngeal cancer) and a cytotoxicity test.

As host cells of influenza virus and at the time of a cytotoxicity test, MDCK cells were used. MA-104 cells were used as host cells of rotavirus, and HEp-2 cells were used as host cells of RS virus.

TEST EXAMPLE 1

Anti-influenza Virus Activity

MDCK cells were plated on a 6-well plate (manufactured by CORNING) at a density of $5\times10^5$ cells/well and cultured overnight at 35° C. under a condition of 5% carbon dioxide. An influenza virus (A/PR/8/34 strain) was diluted to 200 PFU/mL with a serum-free culture medium, and made to infect and adsorbed at a rate of 0.5 mL/well for one hour. After completion of infection and adsorption, an E'-MEM culture medium containing a test compound at a predetermined concentration together with 0.6% agar noble, 1% bovine serum albumin and 3 μg/mL acetylated trypsin was added. After a sufficient coagulation, the plate was turned upside down and a culture was continued for 3 days. After completion of the culture, alive cells were dyed with 1% Neutral Red, the cells were fixed with 10% formalin, the agar medium was removed by means of running water, and the number of plaques was counted. The plaque-inhibitory rate was expressed in terms of percentage based on control sample containing no test compound.

The results are shown in Table I-2, wherein the numbers of test compounds are the same as those in Examples.

TABLE I-2

| Example No. | Concentration of test compound added (μg/mL) | Inhibitory rate (%) |
|---|---|---|
| I-2 | 10 | 95 |
| I-4 | 100 | 80 |
| I-6 | 10 | 47 |
| I-7 | 100 | 42 |
| I-8 | 100 | 42 |
| I-9 | 100 | 31 |
| I-10 | 100 | 26 |
| I-12 | 100 | 28 |
| I-13 | 100 | 39 |

Further, anti-influenza virus activities of the nitrogen-containing heterocyclic carbamoyl derivatives represented by general formula [23] which can be derived from the compounds of the present invention or salt of said derivatives were also evaluated in the same manner as in Test Example 1. As the test compound, 6-fluoro-3-hydroxy-2-pyrazinecarboxamide dissolved in dimethyl sulfoxide to prepare a 10 mg/mL medium was used, which was diluted with culture solution to a predetermined concentration just before use. As the result, the anti-influenza virus activity was found to be 100% in terms of plaque inhibitory rate at a test compound concentration of 1 μg/mL, demonstrating excellency of the test compound as an anti-viral agent.

TEST EXAMPLE 2

Anti-rotavirus Activity

MA-104 cells were plated on a 6-well plate (manufactured by CORNING) at a density of $5\times10^5$ cells/well and cultured overnight at 37° C. under a condition of 5% carbon dioxide. Rotavirus (Ku strain) activated with 10 μg/mL acetylated trypsin for 30 minutes was diluted to 140 PFU/mL with a serum-free culture solution and made to infect and adsorbed for one hour at a rate of 0.5 mL/well. After completion of infection and adsorption, the infecting medium was removed, and an E'MEM culture medium containing 30 μg/mL of test compound, 5 μg/mL of trypsin and 1.4% agarose was added. The MA-104 cells infected with the rotavirus was cultured for 3 days at 37° C. under a condition of 5% carbon dioxide, after which 0.7% agarose containing 0.005% Neutral Red was superposed, and the culture was continued for an additional one day under the same conditions as above. After completion of the culture, the test plate was fixed with 3% formaldehyde solution, the test culture medium solidified with agar was removed, and thereafter the number of plaques was counted. The inhibitory rate against rotavirus was calculated from the numbers of plaques in the compound-treated group and untreated group.

As a result, it was found that the compound of Example I-1 shows an anti-rotavirus activity.

TEST EXAMPLE 3

Anti-RS Virus (Respiratory Syncytial Virus) Activity

HEp-2 cells were scattered on a 6-well plate (manufactured by CORNING) at a density of $5\times10^5$ cells/well and cultured overnight at 37° C. under a condition of 5% carbon dioxide. A RS virus (A-2 strain) was diluted to 140 PFU/mL with a serum-free culture medium, and made to infect and adsorbed for one hour at a rate of 0.5 mL/hole.

After completion of infection and adsorption, the infecting medium was removed, and an E'MEM culture medium containing 30 μg/mL of test compound, 0.12% of glutamine, 2% of fetal bovine serum and 1% of methyl cellulose was added. The HEp-2 cells infected with RS virus were cultured for 3 days at 35° C. under a condition of 5% carbon dioxide. After completion of the culture, the test plate was fixed with 3% formaldehyde solution, and the test culture medium containing methyl cellulose was removed. Thereafter, the test plate was dyed with 5% Giemza solution, and the number of plaques was counted. The inhibitory rate against RS virus was calculated from the plaque numbers in the compound-treated group and untreated group.

As a result, it was found that the compound of Example I-14 shows an anti-RS virus activity.

TEST EXAMPLE 4

Cytotoxic Activity

A culture medium containing a test compound at a predetermined concentration was added to a 96-well plate (manufactured by CORNING CO.) at a volume of 100 μL/well. Subsequently, MDCK cells were prepared into a dispersion having a concentration of $2 \times 10^4$ cells/mL in a culture medium, scattered at a rate of 100 μL/hole, and cultured for 3 days at 37° C. under a condition of 5% carbon dioxide. At the time of completing the culture, the number of alive cells was counted according to XTT method [for example, CANCER RESEARCH, Vol. 48, Pages 4,827–4, 833 (1988), etc.].

As a result, all the compounds listed in Table I-2 showed a 50% cell growth inhibitory concentration ($IC_{50}$) of 100 μg/mL or above.

BEST EMBODIMENT FOR CARRING OUT THE INVENTION

Next, the compounds of the present invention and the production intermediates of the present invention will be explained by referring to Referential Examples and Examples. The present invention is by no means limited thereby.

In the Referential Examples and Examples presented below, the mixing ratios referred to in eluents are all in terms of "ratio by volume". The carrier for column chromatography was Silica Gel BW-127ZH (manufactured by Fuji Silysia Chemical Co.); the carrier for reversed phase chromatography was YMC·GEL ODS-AM 120-S50 (YMC CO., LTD.); and the carrier for ion-exchange column chromatography was DEAE Cellulose (manufactured by Wako Pure Chemical Industries).

The mark used in the referential Examples and Examples has the following meaning:

DMSO-$d_6$: Deuterated dimethyl sulfoxide

REFERENTIAL EXAMPLE I-1

In 100 mL of concentrated sulfuric acid was dissolved 17.0 g of methyl 3-amino-6-bromo-2-pyrazinecarboxylate. At an ice-cooled temperature, 10.1 g of sodium nitrite was added and stirred for 30 minutes. The reaction mixture was poured into 920 mL of methanol and heated under reflux for 5 hours. After cooling the reaction mixture, the mixture thus concentrated under reduced pressure, the residue thus obtained was added to a mixture of 500 mL of ice water and 600 mL of chloroform, and the mixture thus obtained was separated into layers. The organic layer was washed successively with a saturated aqueous solution of sodium hydrogen carbonate, water and saturated aqueous solution of sodium chloride and dried on anhydrous magnesium sulfate, and the solvent was removed under reduced pressure. Thus, 6.30 g of methyl 6-bromo-3-methoxy-2-pyrazinecarboxylate was obtained as a light yellow oily product.

IR (KBr) cm$^{-1}$: 1735
$^1$H-NMR (CDCl$_3$) δ: 3.97 (3H,s), 4.06 (3H,s), 8.37 (1H,s)

REFERENTIAL EXAMPLE I-2

In an atmosphere of nitrogen gas, 11.4 g of methyl 6-bromo-3-methoxy-2-pyrazinecarboxylate was dissolved in 227 mL of toluene, and 10.3 g of benzophenoneimine, 0.42 g of tris(dibenzylideneacetone)dipalladium, 0.86 g of (s)-(−)-2,2'-bis(diphenylphosphino)-1,1'-binaphthyl and 6.20 g of sodium tert-butoxide were successively added. The mixture thus obtained was stirred at 80° C. for one hour. After cooling the reaction mixture, it was filtered. The filtrate was purified by column chromatography [eluent: toluene:ethyl acetate=20:1]. The oily product thus obtained was dissolved in 140 mL of tetrahydrofuran, 7 mL of 2 mol/L hydrochloric acid was added, and the mixture thus obtained was stirred at room temperature for 15 minutes. A mixture of 200 mL of chloroform and 50 mL of water was added to the reaction mixture and then 1 mol/L sodium hydroxide was added to alkalinize the mixture, and the organic layer was separated. The organic layer thus obtained was washed with a saturated aqueous solution of sodium chloride and dried on anhydrous magnesium sulfate, and the solvent was removed under reduced pressure. The residue was purified by column chromatography [eluent: toluene:ethyl acetate=1:1] to obtain 3.64 g of methyl 6-amino-3-methoxy-2-pyrazinecarboxylate as a yellow-colored oily product.

IR (KBr) cm$^{-1}$: 1716, 1670
$^1$H-NMR (DMSO-$d_6$) δ: 3.80(3H,s), 3.82(3H,s), 7.20(2H, brs), 7.77(1H,s)

REFERENTIAL EXAMPLE I-3

In 70 mL of methanol was dissolved 3.5 g of methyl 6-amino-3-methoxy-2-pyrazinecarboxylate. After introducing gaseous ammonia into the solution to prepare a saturated solution, and the solution was stirred at room temperature for 14 hours. By removing the solvent from the reaction mixture under reduced pressure, 3.1 g of 6-amino-3-methoxy-2-pyrazinecarboxamide was obtained as a solid product.

IR (KBr) cm$^{-1}$: 1684
$^1$H-NMR (DMSO-$d_6$) δ: 3.79(3H,s), 5.87(2H,brs), 7.30–7.75(3H,m)

REFERENTIAL EXAMPLE I-4

In an atmosphere of nitrogen gas, 1.50 g of 6-amino-3-methoxy-2-pyrazinecarboxamide was dissolved in 12 mL of 70% hydrogen fluoride-pyridine solution at an ice-cooled temperature. Then, 0.71 g of sodium nitrite was added at −50° C., and the mixture thus obtained was stirred at 10° C. for one hour. After stirring the reaction mixture for an additional one hour, a mixture of 50 mL of ice water and 100 mL of chloroform was added, and the mixture thus obtained was separated into layers. The organic layer was washed with saturated aqueous solution of sodium chloride and dried on anhydrous magnesium sulfate and the solvent was removed under reduced pressure. Thus, 1.29 g of 6-fluoro-3-methoxy-2-pyrazinecarboxamide was obtained as a solid product.

IR (KBr) cm$^{-1}$: 1707

$^1$H-NMR (DMSO-d$_6$) δ: 3.95(3H,s), 7.55–8.15(2H,m), 8.39(1H,d,J=8.3 Hz)

REFERENTIAL EXAMPLE I-5

In an atmosphere of nitrogen gas, 1.51 g of sodium iodide was dissolved in 22 mL of acetonitrile. After adding 1.10 g of trimethylsilyl chloride, the mixture thus obtained was stirred at room temperature for 20 minutes. Then, 0.43 g of 6-fluoro-3-methoxy-2-pyrazinecarboxamide was added, and the mixture thus obtained was stirred at the same temperature as above for 18 hours. The reaction mixture was added to a mixture of 10 mL of water and 200 mL of chloroform, and the mixture thus formed was separated into layers. The organic layer was washed successively with 5% aqueous solution of sodium thiosulfate and saturated aqueous solution of sodium chloride and dried on anhydrous magnesium sulfate, and the solvent was removed under reduced pressure. The residue was purified by column chromatography [eluent: hexane:ethyl acetate=2:1] to obtain 0.06 g of 6-fluoro-3-hydroxy-2-pyrazinecarboxamide as a white-colored solid product.

IR (KBr) cm$^{-1}$: 1685, 1658

$^1$H-NMR (CDCl$_3$) δ: 5.40–7.80(2H,m), 8.31 (1H,d,J=7.8 Hz), 12.33(1H,s)

REFERENTIAL EXAMPLE I-6

In 40 mL of dichloroethane was dissolved 1.0 g of methyl 6-chloro-3-oxo-3,4-dihydro-2-pyrazinecarboxylate. In an atmosphere of nitrogen gas, 1.0 mL of 1,1,1,3,3,3-hexamethyldisilazane and 0.54 mL of chlorotrimethylsilane were successively added and heated at 90° C. for 2 hours. The mixture was allowed to cool, and the solvent was removed under reduced pressure. The residue was dissolved in 30 mL of dichloroethane, 2.68 g of β-D-ribofuranose-1-acetate-2,3,5-tribenzoate and 1.24 ml of stannic (IV) chloride were successively added, and the mixture thus obtained was stirred at room temperature for 16 hours. The reaction mixture was added to 30 mL of ice water and adjusted to pH 8 with a saturated aqueous solution of sodium hydrogen carbonate, and separated into layers. The organic layer was washed successively with water and saturated aqueous solution of sodium chloride and dried on anhydrous magnesium sulfate, and the solvent was removed under reduced pressure. The residue thus obtained was purified by column chromatography [eluent: hexane:ethyl acetate=4:1] to obtain 1.76 g of methyl 4-{(2R,3R,4R,5R)-3,4bis(benzoyloxy)-5-[(benzoyloxy)methyl]tetrahydro-2-furanyl}-6-chloro-3-oxo-3,4-dihydro-2-pyrazinecarboxylate as a yellow-colored oily product.

IR (neat) cm$^{-1}$: 1728

$^1$H-NMR (CDCl$_3$) δ: 3.94(3H,s), 4.5–4.9(3H,m), 5.6–6.0 (2H,m), 6.3–6.5(1H, m), 7.1–8.2(16H,m)

REFERENTIAL EXAMPLE I-7

In 16 mL of methanol was suspended 0.80 g of methyl 4-{(2R,3R,4R,5R)-3,4-bis(benzoyloxy)-5-[(benzoyloxy) methyl]tetrahydro-2-furanyl} -6-chloro-3-oxo-3,4-dihydro-2-pyrazinecarboxylate. While cooling the suspension with ice, 0.73 g of a 28% methanol solution of sodium methoxide was added, and the mixture thus obtained was stirred at the same temperature as above for one hour. After stirring the mixture at room temperature for an additional 3 hours, the mixture was adjusted to pH 7 with 6 mol/L hydrochloric acid, and the solvent was removed under reduced pressure. The residue was purified by column chromatography [eluent: chloroform:methanol=10:1] to obtain 0.29 g, of methyl 6-chloro-4-[(2R,3R,4S ,5R)-3,4-dihydroxy-5-(hydroxymethyl)tetrahydro-2-furanyl]-3-oxo-3,4-dihydro-2-pyrazinecarboxylate as a yellow-colored oily product.

IR (neat) cm$^{-1}$: 1728

$^1$H-NMR (CDCl$_3$+DMSO-d$_6$) δ: 3.6–5.6(11H,m), 5.99 (1H,s), 8.67(1H,s)

REFERENTIAL EXAMPLE I-8

In 4.0 mL of N,N-dimethylformamide was dissolved 0.39 g of methyl 3-oxo-3,4-dihydro-2-pyrazinecarboxylate. In an atmosphere of nitrogen gas, 90 mg of sodium hydride was added and stirred at room temperature for 2 hours. Then, a suspension of 0.50 g of 4-[(trityloxy)methyl]-2-cyclopenten-1-yl acetate, 0.62 g of tetrakis-triphenylphosphine palladium and 50 mg of triphenylphosphine in 4 mL of tetrahydrofuran was added, and the mixture thus obtained was stirred at room temperature for one hour and thereafter at 60° C. for 4 hours. The reaction mixture was allowed to cool, diluted with 30 mL of ethyl acetate and 20 mL of water, adjusted to pH 4 with 1 mol/L hydrochloric acid, and separated into layers. The organic layer was washed successively with saturated aqueous solution of sodium hydrogen carbonate, water and saturated aqueous solution of sodium chloride and dried on anhydrous magnesium sulfate, and the solvent was removed under reduced pressure. The residue was purified by column chromatography [eluent: hexane:ethyl acetate=1:1] to obtain 0.23 g of methyl 3-oxo-4-{4-[(trityloxy)methyl]-2-cyclopenten-1-yl}-3,4-dihydro-2-pyrazinecarboxylate as a light yellow oily product.

IR (neat) cm$^{-1}$: 1735

$^1$H-NMR (CDCl$_3$) δ: 1.2–1.6(2H,m), 2.8–3.4(3H,m), 3.98 (3H,s), 5.6–5.8(1H,m), 5.8–6.1(1H,m), 6.2–6.4(1H,m), 7.0–7.6(17H,m)

REFERENTIAL EXAMPLE I-9

In 2.0 mL of 80% aqueous solution of acetic acid was dissolved 0.20 g of methyl 3-oxo-4-{4-[(trityloxy)methyl]-2-cyclopenten-1-yl}-3,4-dihydro-2-pyrazinecarboxylate, and the solution thus obtained was heated at 80° C. for one hour. The reaction mixture was allowed to cool and diluted with 10 mL of water, the deposited precipitate was filtered off, and the filtrate was concentrated under reduced pressure. The residue was purified by column chromatography [eluent: ethyl acetate] to obtain 77 mg of methyl 4-[4-(hydroxymethyl)-2-cyclopenten-1-yl]-3-oxo-3,4-dihydro-2-pyrazinecarboxylate as a light yellow oily product.

IR (neat) cm$^{-1}$: 1738

$^1$H-NMR (CDCl$_3$) δ: 1.4–1.7(1H,m), 2.2–3.2(3H,m), 3.5–3.9(2H,m), 3.96(3H,s), 5.6–5.8(1H,m), 5.8–6.1(1H,m), 6.2–6.5(1H,m), 7.43(1H,d,J=4.2 Hz), 7.70(1H,d,J=4.2 Hz)

REFERENTIAL EXAMPLE I-10

In 6.0 mL of N,N-dimethylformamide was dissolved 0.24 g of methyl 3-oxo-3,4-dihydro-2-pyrazinecarboxylate. After adding 82 mg of 18-crown-6-ether and 62 mg of sodium hydride, the mixture thus obtained was heated at 80° C. for one hour. Then, a solution of 0.30 g of (4aR,7R,8aS)-2-phenylhexahydropyrano[3,2-d][1,3]-dioxan-7-yl 4-methylbenzenesulfonate in 3.0 mL of N,N-dimethylformamide was dropwise added, and the mixture thus obtained was heated for 4 hours at 100° C. The reaction mixture was allowed to cool, diluted with 50 mL of ethyl acetate and 25 mL of water, and separated into layers. Further, the aqueous layer was extracted with three 25 ml portions of ethyl acetate. All the organic layers obtained were united and washed successively with saturated aqueous solution of sodium hydrogen carbonate and saturated aqueous solution of sodium chloride and dried on anhydrous magnesium sulfate, and the solvent was removed under reduced pressure. The residue thus obtained was purified by column chromatography [eluent: toluene:ethyl acetate=3:1]. Isopropyl ether and diethyl ether were added to the purified product, and the solid product was collected by filtration. Thus, 84 mg of methyl 4-[(4aR,7S,8aS)-2-phenylhexahydropyrano[3,2-d][1,3]dioxin-7-yl]-3-oxo-3,4-dihydro-2-pyrazinecarboxylate was obtained as a white-colored solid product.

R (KBr) cm$^{-1}$: 1732

H-NMR (DMSO-d$_6$) δ: 1.97–2.37(2H,m), 3.22–4.36(6H, m), 3.95(3H,s), 5.4–5.6(1H,m), 5.67(1H,s), 7.3–7.5(5H,m), 8.35(1H,d,J=10 Hz), 8.37(1H,d,J=10 Hz)

REFERENTIAL EXAMPLE I-11

In 5.7 mL of N,N-dimethylformamide was dissolved 0.38 g of methyl 3-oxo-3,4-dihydro-2-pyrazinecarboxylate. After adding 0.10 g of sodium hydride, the mixture thus obtained was heated at 80° C. for 30 minutes. Then, 0.19 g of (4aR,7S,8R,8aS)-8-hydroxy-2-phenylhexahydropyrano[3, 2-d][1,3]dioxan-7-yl 4-methylbenzenesulfonate was added and heated at 100° C. for an additional 4.5 hours. The reaction mixture was allowed to cool and diluted with 30 mL of ethyl acetate and 20 mL of water, and the mixture thus obtained was separated into layers. Further, the aqueous layer was extracted with 30 mL of ethyl acetate. All the organic layers thus obtained were united and washed successively with saturated aqueous solution of sodium hydrogen carbonate and saturated aqueous solution of sodium chloride and dried on anhydrous magnesium sulfate, and the solvent was removed under reduced pressure. The residue thus obtained was purified by column chromatography [eluent: toluene:ethyl acetate=2:1], isopropyl ether and diethyl ether was added, and the solid product was collected by filtration. Thus, 65 mg of methyl 4-[[(4aR,7R,8S,8aS)-8-hydroxy-2-phenyl-hexahydropyrano[3,2-d][1,3]dioxin-7-yl]-3-oxo-3,4-dihydro-2-pyrazinecarboxylate was obtained as a yellow-colored solid product.

IR (KBr) cm$^{-1}$: 3447, 1740

$^1$H-NMR (CDCl$_3$) δ: 2.69(1H,d,J=2.2 Hz), 3.98(3H,s), 3.52–4.62(7H,m), 4.6–5.0(1H,m), 5.59(1H,s), 7.2–7.6(5H, m), 7.52(1H,d,J=4.0 Hz), 8.17(1H,d,J=4.0 Hz)

REFERENTIAL EXAMPLE I-12

In 12.2 mL of 1,1,1,3,3,3-hexamethyldisilazane was suspended 1.52 g of methyl 3-oxo-3,4-dihydro-2-pyrazinecarboxylate. The suspension thus obtained was heated under reflux for one hour. The mixture was allowed to cool, and the solvent was removed under reduced pressure. In an atmosphere of nitrogen gas, the residue thus obtained was dissolved in 30 mL of dichloroethane, 4.98 g of β-D-ribofuranose-1-acetate-2,3,5-tribenzoate and 1.73 ml of stannic (IV) chloride were successively added, and the mixture thus obtained was stirred at room temperature for 14 hours. The reaction mixture was diluted with 30 ml of chloroform and 30 mL of saturated aqueous solution of sodium hydrogen carbonate, the precipitate was filtered off, and the organic layer was taken out. The organic layer was washed successively with water and saturated aqueous solution of sodium chloride and dried on anhydrous magnesium sulfate, and the solvent was removed under reduced pressure. The residue thus obtained was purified by column chromatography [eluent: n-hexane:ethyl acetate=1:1] to obtain 3.4 g of methyl 4-{(2R,3R,4R,5R)-3,4-bis (benzoyloxy)-5-[(benzoyloxy)methyl]tetrahydro-2-furanyl}-3-oxo-3,4-dihydro-2-pyrazinecarboxylate as a white-colored solid product.

IR(KBr) cm$^{-1}$: 1728

$^1$H-NMR (CDCl$_3$) δ: 3.95(3H,s), 4.55–5.00(3H,m), 5.75–6.00(2H,m), 6.42(1H,d,J=3.0 Hz), 7.20–8.20(17H,m)

REFERENTIAL EXAMPLE I-13

Methyl 4-{(2R,3R,4R,5R)-3,4-bis(benzoyloxy)-5-[(benzoyloxy)methyl]tetrahydro-2-furanyl}-3-oxo-3,4-dihydro-2-pyrazinecarboxylate was treated in the same manner as in Referential Example I-7 to obtain methyl 4-[(2R, 3R,4S,5R)-3,4-dihydroxy-5-(hydroxymethyl)tetrahydro-2-furanyl]-3-oxo-3,4-dihydro-2-pyrazinecarboxylate.

IR (KBr) cm$^{-1}$: 1740

$^1$H-NMR (DMSO-d$_6$) δ: 3.60–4.20(5H,m), 3.83(3H,s), 5.00–5.40(2H,m), 5.61(1H,d,J=4.6 Hz), 5.91(1H,s), 7.47 (1H,d,J=4.4 Hz), 8.29(1H,d,J=4.4 Hz)

REFERENTIAL EXAMPLE I-14

In 5 mL of acetone was suspended 0.50 g of methyl 4-[(2R,3R,4S,5R)-3,4-dihydroxy-5-(hydroxymethyl) tetrahydro-2-furanyl]-3-oxo-3,4-dihydro-2-pyrazinecarboxylate. Then, 1 ml of trimethyl orthoformate and 33 mg of p-toluenesulfonic acid monohydrate were successively added, the mixture thus obtained was heated under reflux for one hour, and the solvent was removed under reduced pressure. By purifying the residue by column chromatography [eluent: ethyl acetate], 0.49 g of methyl 4-[(3aR,4R,6R,6aR)-6-(hydroxymethyl)-2,2-dimethyltetrahydrofuro[3,4-d][1,3]dioxol-4-yl]-3-oxo-3,4-dihydro-2-pyrazinecarboxylate was obtained as a white-colored solid product.

IR (KBr) cm$^{-1}$: 1728

$^1$H-NMR (CDCl$_3$) δ: 1.34(3H,s), 1.59(3H,s), 3.10(1H, brs), 3.65–4.25(2H,m), 3.95(3H,s), 4.49(1H,s), 4.92(2H,s), 5.91(1H,s), 7.48(1H,d,J=4.3 Hz), 7.89(1H,d,J=4.3 Hz)

REFERENTIAL EXAMPLE I-15

In 4 mL of pyridine was dissolved 0.22 g of methyl 4-[(3aR,4R,6R,6aR)-6-(hydroxymethyl)-2,2-dimethyltetrahydrofuro[3,4-d][1,3]dioxol-4-yl]-3-oxo-3,4-dihydro-2-pyrazinecarboxylate. Then, 0.17 g of dibenzyl phosphate, 0.40 g of triphenylphosphine and 0.30 mL of diisopropyl azodicarboxylate were successively added and stirred at room temperature for 15 hours, and the solvent was removed under reduced pressure. By purifying the residue by column chromatography [eluent: ethyl acetate], 0.37 g of methyl 4-[(3aR,4R,6R,6aR)-6-({[bis(benzyloxy) phosphoryl]oxy}methyl)-2,2-dimethyltetrahydrofuro[3,4-d] [1,3]dioxol-4-yl]-3-oxo-3,4-dihydro-2-pyrazinecarboxylate was obtained as an orange-colored solid product.

R (KBr) cm$^{-1}$: 1734

H-NMR (CDCl$_3$) δ: 1.31(3H,s), 1.56(3H,s), 3.96(3H,s), 4.10–4.30(2H,m), 4.30–4.55(1H,m), 4.55–4.70(2H,m), 4.90–5.15(4H,m), 5.85–5.95(1H,m), 7.10–7.85(12H,m)

REFERENTIAL EXAMPLE I-16

In 33 ml of methanol was dissolved 1.1 g of 3-oxo-3,4-dihydro-2-pyrazinecarbonitrile synthesized according to the description of J. Heterocycl. Chem., Vol. 19, Pages 1,397–1,402 (1982). While cooling the solution with ice, gaseous hydrogen chloride was introduced until saturation, after which the solution was stirred at the same temperature as above for 8 hours. The solvent was removed under reduced pressure, the residue thus obtained and dissolved in 55 ml of a 7 mol/L solution of ammonia in methanol at an ice-cooled temperature, and the solution thus obtained was stirred at the same temperature as above for 5 minutes. The solid product formed was collected by filtration to obtain 1.1 g of 3-oxo-3,4-dihydro-2-pyrazinecarboximidamide as a light yellow-colored solid product.

R (KBr) cm$^{-1}$: 3379, 3000, 1698

H-NMR (DMSO-d$_6$) δ: 7.50(1H,d,J=2.0 Hz), 8.33(1H,brs), 8.18(1H,d,J=2.0 Hz), 8.33(2H,brs)

REFERENTIAL EXAMPLE I-17

In a mixture of 0.5 mL of ethanol and 1.9 mL of diethyl ether was dissolved 0.30 g of 6-fluoro-3-oxo-3,4-dihydro-2-pyrazinecaronitrile. While cooling the solution with ice, gaseous hydrogen chloride was introduced until saturation, and then the solution was stirred for 5 hours. The reaction mixture was mixed with 5.0 mL of diethyl ether, the deposited solid product was collected by filtration and washed successively with 10 mL of diethyl ether, a mixture consisting of 2.5 mL of ethanol and 2.5 mL of diethyl ether, and 5 mL of diethyl ether. Thus, 0.28 g of 6-fluoro-3-oxo-3,4-dihydro-2-pyrazinecarboximidoate was obtained as a yellow-colored solid product.

R (KBr) cm$^{-1}$: 3041, 1670

H-NMR (DMSO-d$_6$+D$_2$O) δ: 1.43(3H,t,J=7.0 Hz), 4.50 (2H,q,J=7.0 Hz), 8.49(1H,d,J=8.0 Hz)

REFERENTIAL EXAMPLE I-18

At an ice-cooled temperature, gaseous ammonia was introduced into 2.0 mL of ethanol to prepare a saturated solution, and then 0.10 g of 6-fluoro-3-oxo-3,4-dihydro-2-pyrazinecarboximidoate and 2.0 mL of ethanol were added. After elevating the temperature to room temperature, the mixture was left to stand for 17 hours. The deposited solid product was collected by filtration and washed with ethanol. The residue thus obtained was purified by silica gel column chromatography [eluent: chloroform:methanol=10:1], ethanol was added to the purified product, and the solid product was collected by filtration. Thus, 20 mg of 6-fluoro-3-oxo-3,4-dihydro-2-pyrazinecarboximidamide was obtained.

R (KBr) cm$^{-1}$: 3445, 3030, 1684

H-NMR (DMSO-d$_6$+D$_2$O) δ: 8.26(1H,d,J=8.5 Hz)

EXAMPLE I-1

In 5.0 mL of ,1,1,1,3,3,3-hexamethyldisilazane was suspended 1.0 g of 3-hydroxy-2-pyrazinecarboxamide. The suspension was heated under reflux for 30 minutes and allowed to cool, and the solvent was removed under reduced pressure. The residue was dissolved in 5.0 mL of dichloroethane in an atmosphere of nitrogen gas, 3.11 g of β-D-ribofuranose-1-acetate-2,3,5-tribenzoate and 0.50 mL of stannic (IV) chloride were successively added, and the mixture thus obtained was stirred at room temperature for 22 hours. The reaction mixture was diluted with 30 mL of ethyl acetate and 20 mL of water, pH was adjusted to 8 with saturated aqueous solution of sodium hydrogen carbonate, the precipitate was filtered off, and the organic layer was separated. The organic layer was washed successively with water and saturated aqueous solution of sodium chloride and dried on anhydrous magnesium sulfate, and the solvent was removed under reduced pressure. The residue was purified by column chromatography [eluent: ethyl acetate:methanol= 10:1], then isopropyl ether was added, and the solid matter was collected by filtration. Thus, 0.41 g of [(2R,3R,4R,5R)-5-[3-(aminocarbonyl)-2-oxo-1(2H)-pyrazinyl]-3,4-bis(benzoyloxy)tetrahydro-2-furanyl]methyl benzoate was obtained as a white-colored solid product.

R (KBr) cm$^{-1}$: 1734, 1685

H-NMR (CDCl$_3$) δ: 4.6–5.1(3H,m), 5.8–6.2(3H,m), 6.39 (1H,d,J=2.5 Hz), 7.2–8.2(17H,m), 8.95(1H,brs)

EXAMPLE I-2

In 4 mL of methanol was dissolved 0.37 g of [(2R,3R,4R,5R)-5-[3-(aminocarbonyl)-2-oxo-1(2H)-pyrazinyl]-3,4-bis(benzoyloxy)tetrahydro-2-furanyl]methyl benzoate. While cooling the solution with ice, gaseous ammonia was introduced until saturation. The reaction mixture was stirred at room temperature for 15 hours, and the solvent was removed under reduced pressure. Methanol was added to the residue, and the precipitate was collected by filtration to obtain 0.12 g of 4-[(2R,3R,4S,5R)-3,4-dihydroxy-5-(hydroxymethyl)tetrahydro-2-furanyl]-3-oxo-3,4-dihydro-2-pyrazinecarboxamide as a light brown-colored solid product.

R (KBr) cm$^{-1}$: 1654

H-NMR (DMSO-d$_6$) δ: 3.73(2H,dd,J=5.4,5.4 Hz), 3.8–4.2(3H,m), 5.08(1H,brs), 5.24(1H,t,J=5.4 Hz), 5.61(1H,brs), 5.92(1H,s), 7.54(1H,d,J=4.2 Hz), 7.71(1H,brs), 8.27 (1H,d,J=4.2 Hz), 8.30(1H,brs)

EXAMPLE I-3

In 5.0 mL of 1,1,1,3,3,3-hexamethyldisilazane was suspended 0.62 g of 3-hydroxy-2-pyrazinecarboxamide. The suspension was heated under reflux for one hour. The reaction mixture was allowed to cool, the solvent was removed under reduced pressure, and the residue was dissolved in 2.0 mL of dichloroethane in an atmosphere of nitrogen gas, to which was added a solution at room temperature, in 3.0 mL of dichloroethane, of a mixture of (2R,3S)-5-(acetyloxy)-2-[(acetyloxy)methyl]tetrahydro-3-furanyl acetate and (3R,4S)-4,6-bis(acetyloxy)tetrahydro-2H-pyran-3-yl acetate prepared elsewhere according to the procedure described in J. Med. Chem., Vol. 28, No. 7, Pages 904–910 (1985), together with 0.32 mL of titanium (IV) chloride. After additionally adding thereto 5.0 mL of dichloroethane, the mixture thus obtained was stirred for 17 hours. The reaction mixture was diluted with 100 mL of chloroform and 25 ml of saturated aqueous solution of sodium hydrogen carbonate, the precipitate was filtered off, and the organic layer was separated. The organic layer was washed successively with water and saturated aqueous solution of sodium chloride and dried on anhydrous magnesium sulfate, and the solvent was removed under reduced pressure. The residue thus obtained was purified by column chromatography [eluent: ethyl acetate:methanol=10:1] to obtain 0.43 g of {(2R,3S)-3-(acetyloxy)-5-[3-(aminocarbonyl)-2-oxo-1(2H)-pyrazinyl]tetrahydro-2-furanyl}methyl acetate as a light brown-colored oily product.

R (KBr) cm$^{-1}$: 1735, 1685

H-NMR (CDCl$_3$) δ: 2.07(3H,s), 2.14(3H,s), 1.8–2.6(2H, m), 4.0–4.6(2H,m), 5.0–5.4(2H,m), 6.33(1H,d,J=5.9 Hz), 6.64(1H,brs), 7.76(1H,d,J=4.2 Hz), 7.83(1H,d,J=4.2 Hz), 9.06(1H,brs)

EXAMPLE I-4

In 2 ml of methanol was dissolved 0.20 g of {(2R,3S)-3-(acetyloxy)-5-[3-(aminocarbonyl)-2-oxo-1(2H)-pyrazinyl]tetrahydro-2-furanyl}methyl acetate. While cooling the solution with ice, 0.23 g of 28% methanol solution of sodium methoxide was added, and stirred for 20 minutes. Then, 1.2 ml of 1 mol/L hydrochloric acid was added to the reaction mixture, and the solvent was removed under reduced pressure. The residue thus obtained was purified by column chromatography [eluent: chloroform:methanol= 10:1] to obtain 90 mg of 4-[(4S,5R)-4-hydroxy-5-(hydroxymethyl)tetrahydro-2-furanyl]-3-oxo-3,4-dihydro-2-pyrazinecarboxamide as a yellow oily product.

R (KBr) cm$^{-1}$: 1684

H-NMR (DMSO-d$_6$) δ: 1.8–2.2(2H,m), 3.0–4.4(4H,m), 4.50–5.20(2H,m), 6.13(1H,d,J=5.9 Hz), 7.59(1H,d,J=4.2 Hz), 7.70(1H,brs), 7.92(1H,d,J=4.2 Hz), 8.45(1H,brs)

EXAMPLE I-5

6-Fluoro-3-hydroxy-2-pyrazinecarboxamide was treated in the same manner as in Example I-1 to obtain [(2R,3R,4R,5R)-5-[3-(aminocarbonyl)-5-fluoro-2-oxo-1(2H)-pyrazinyl]-3,4-bis(benzoyloxy)tetrahydro-2-furanyl]methyl benzoate.

R (KBr) cm$^{-1}$: 1726, 1690

H-NMR (DMSO-d$_6$) δ: 4.6–5.0(3H,m), 5.9–6.1(2H,m), 6.33(1H,s), 7.3–8.2(17H,m), 8.53(1H,brs)

Example I-6

In 2.0 mL of methanol was dissolved 0.15 g of [(2R,3R,4R,5R)-5-[3-(aminocarbonyl)-5-fluoro-2-oxo-1(2H)-pyrazinyl]-3,4-bis(benzoyloxy)tetrahydro-2-furanyl]methyl benzoate. Then, 0.14 g of a 28% methanolic solution of sodium methoxide was added and stirred at an ice-cooled temperature for 20 minutes and thereafter at room temperature for 30 minutes. The reaction mixture was acidified with 0.75 mL of 1 mol/L hydrochloric acid and the solvent was removed under reduced pressure. After purifying the residue by column chromatography [eluent: chloroform:methanol= 5:1], isopropanol and diethyl ether were added and the solid product was collected by filtration to obtain 40 mg of 4-[(2R,3R,4S,5R)-3,4-dihydroxy-5-(hydroxymethyl) tetrahydro-2-furanyl]-6-fluoro-3-oxo-3,4-dihydro-2-pyrazinecarboxamide.

R (KBr) cm$^{-1}$: 1686

EXAMPLE I-7

In 4 mL of methanol was dissolved 0.26 g of methyl 6-chloro-4-[(2R,3R,4S,5S)-3,4-dihydroxy-5-(hydroxymethyl)tetrahydro-2-furanyl]-3-oxo-3,4-dihydro-2-pyrazinecarboxylate. While cooling the solution with ice, gaseous ammonia was introduced until saturation. The reaction mixture was stirred at an ice-cooled temperature for one hour and then the solvent was removed under reduced pressure. By purifying the residue thus obtained by column chromatography [eluent: chloroform:methanol=7:1], 0.06 g of 6-chloro-4-[(2R,3R,4S,5R)-3,4-dihydroxy-5-(hydroxymethyl)tetrahydro-2-furanyl]-3-oxo-3,4-dihydro-2-pyrazinecarboxamide was obtained as a light yellow-colored solid product.

R (KBr) cm$^{-1}$: 1693

EXAMPLE I-8

In 1 ml of methanol was dissolved 75 mg of methyl 4-[4-(hydroxymethyl)-2-cyclopenten-1-yl]-3-oxo-3,4-dihydro-2-pyrazinecarboxylate. At room temperature, 25% aqueous solution of ammonia was added and stirred for 13 hours, and then the solvent was removed under reduced pressure. Isopropanol was added to the residue, and the solid product was collected by filtration to obtain 20 mg of 4-[4-(hydroxymethyl)-2-cyclopenten-1-yl]-3-oxo-3,4-dihydro-2-pyrazinecarboxamide as a white-colored solid product.

R (KBr) cm$^{31\ 1}$: 1668

H-NMR (DMSO-d$_6$) δ: 1.2–3.8(5H,m), 4.92(1H,brs), 5.8–6.1(2H,m), 6.2–6.4(1H,m), 7.4–8.1(3H,m), 8.20(1H, brs)

EXAMPLE I-9

In 5.0 mL of 80% aqueous solution of acetic acid was dissolved 80 mg of methyl 4-[(4aR,7S,8aS)-2-phenylhexahydropyrano[3,2-d][1,3]dioxin-7-yl]-3-oxo-3,4-dihydro-2-pyrazinecarboxylate. The solution was heated at 80° C. for 2 hours and then allowed to cool, and the solvent was removed under reduced pressure. The residue was diluted with 20 mL of water and washed with diethyl ether, and water was distilled off from the aqueous layer. The residue thus obtained was dissolved in 4.0 mL of methanol, and gaseous ammonia was introduced until saturation at an ice-cooled temperature. After stirring the reaction mixture at room temperature for 2 hours, the solvent was removed under reduced pressure. The residue thus obtained was purified by column chromatography [eluent: chloroform:methanl=10:1] to obtain 24 mg of 4-[(3S,5S,6R)-5-hydroxy-6-(hydroxymethyl)tetrahydro-2H-pyran-3-yl]-3-oxo-3,4-dihydro-2-pyrazinecarboxamide as a solid product.

R (KBr) cm$^{-1}$: 3451, 1676

H-NMR (DMSO-d$_6$) δ: 1.45–1.85(1H,m), 2.10–2.30(1H, m), 2.95–4.05(6H,m), 4.47(1H,t,J=5.6 Hz), 4.83(1H,d,J=5.4 Hz), 5.20–5.30(1H,m), 7.68(1H,brs), 7.80(1H,brs), 8.24(1H, d,J=7.0 Hz), 8.27(1H,d,J=7.0 Hz)

EXAMPLE I-10

Methyl 4-[(4aR,7R,8S,8aS)-8-hydroxy-2-phenylhexahydropyrano[3,2-d][1,3]dioxin-7-yl]-3-oxo-3,4-dihydro-2-pyrazinecarboxylate was treated in the same manner as in Example I-9 to obtain 4-[(3R,4S,5S,6R)-4,5-dihydroxy-6-(hydroxymethyl)tetrahydro-2H-pyran-3-yl]-3-oxo-3,4-dihydro-2-pyrazinecarboxamide.

R (KBr) cm$^{-1}$: 3404, 1670

H-NMR (DMSO-d$_6$) δ: 3.42–3.67(4H,m), 3.95(1H,dd,J= 3.1,13 Hz), 3.90–3.95(1H,m), 4.02(1H,dd, J=3.7,13 Hz), 4.56(1H,t,J=6.1 Hz), 4.68(1H,q,J=4.8 Hz), 4.75(1H,d,J=6.1 Hz), 5.37(1H,d,J=4.5 Hz), 7.49(1H,d,J=4.3 Hz), 7.66(1H, brs), 8.21(1H,d,J=4.3 Hz), 8.34(1H,brs)

EXAMPLE I-11

Methyl 4-[(3aR,4R,6R,6aR)-6-({[bis(benzyloxy) phosphoryl]oxy}methyl)-2,2-dimethyltetrahydrofuro[3,4-d][1,3]dioxol-4-yl]-3-oxo-3,4-dihydro-2-pyrazinecarboxylate was treated in the same manner as in Example I-7 to obtain {(3aR,4R,6R,6aR)-6-[3-20 (aminocarbonyl)-2-oxo-1(2H)-pyrazinyl]-2,2-dimethyltetrahydrofuro[3,4-d}[1,3]dioxol-4-yl]methyl dibenzyl phosphate.

R (KBr) cm$^{-1}$: 1685, 1654

H-NMR (CDCl$_3$) δ: 1.35(3H,s), 1.59(3H,s), 4.00–4.65 (5H,m), 4.80–5.40(4H,m) 5.93(1H,d,J=2.2 Hz), 6.15(1H, brs), 7.10–7.80(10H,m), 7.59(1H,d,J=4.3 Hz), 7.67(1H,d,J= 4.3 Hz), 9.15(1H,brs)

EXAMPLE I-12

In 3 mL of 90% aqueous solution of trifluoroacetic acid was dissolved 60 mg of {(3aR,4R,6R,6aR)-6-[3-(aminocarbonyl)-2-oxo-1(2H)-pyrazinyl]-2,2-dimethyltetrahydrofuro[3,4-d][1,3]dioxol-4-yl]methyl dibenzyl phosphate at an ice-cooled temperature. After stirring the solution thus obtained at the same temperature as above for 30 minutes and further at room temperature for 2 hours, the solvent was removed under reduced pressure. Diethyl ether was added to the residue thus obtained, and the solid product was collected by filtration and washed with methanol. Thus, 15 mg of {(2R,3S,4R,5R)-5-[3-(aminocarbonyl)-2-oxo-1(2H)-pyrazinyl]-3,4-dihydroxytetrahydro-2-furanyl}methyl dihydrogen phosphate was obtained as a light red-colored solid product.

R (KBr) cm$^{-1}$: 1654

H-NMR (DMSO-d$_6$) δ: 2.80–4.80(9H,m), 5.90–6.00(1H, m), 7.47(1H,d,J=4.5 Hz), 7.68(1H,brs), 7.97(1H,d,J=4.5 Hz), 8.30(1H,brs)

EXAMPLE I-13

In a mixture of 2 mL of tetrahydrofuran and 1 mL of water was dissolved 100 mg of {(3aR,4R,6R,6aR)-6-[3-(aminocarbonyl)-2-oxo-1(2H)-pyrazinyl]-2,2-dimethyltetrahydrofuro[3,4-d][1,3]dioxol-4-yl]methyl dibenzyl phosphate. After adjusting the pH value to 0.5 with 6 mol/L hydrochloric acid, the mixture was left to stand at room temperature for 2 days. The deposited solid matter was collected by filtration and washed with ethanol to obtain 40 mg of {(2R,3S,4R,5R)-5-[3-(aminocarbonyl)-2-oxo-1(2H)-pyrazinyl]-3,4-dihydroxytetrahydro-2-furanyl}methyl dibenzyl phosphate as a solid product.

R (KBr) cm$^{-1}$: 1676, 1660

H-NMR (DMSO-d$_6$) δ: 3.70–4.60(5H,m), 5.04(2H,s), 5.12(2H,s), 5.30–5.45(1H,m), 5.71(1H,d,J=4.6 Hz), 5.85–6.00(1H,m), 7.10–7.60(11H,m), 7.76(1H,brs), 7.78 (1H,d,J=3.9 Hz), 8.30(1H,brs)

EXAMPLE I-14

In 2.0 mL of 1,1,1,3,3,3-hexamethyldisilazane were suspended 0.20 g of 3-oxo-3,4-dihydro-2-pyrazinecarboximidamide and 10 mg of ammonium sulfate. Under a stream of nitrogen gas, the suspension was heated under reflux for 10 minutes. After adding 9.0 mg of ammonium sulfate, the mixture was heated under reflux for an additional 2 hours. The reaction mixture was allowed to cool, and the solvent was removed under reduced pressure. The residue thus obtained was dissolved in 4.0 mL of acetonitrile, 0.46 g of β-D-ribofuranose-1,2,3,5-tetraacetate and 0.34 mL of stannic (IV) chloride were successively added, and the mixture thus obtained was stirred at room temperature for 3 hours. Then, 10 μL of trifluoroacetic acid and 1.0 mL of water were added to the reaction mixture, and the solvent was removed under reduced pressure. Further, the same reaction as above was repeated by using 0.05 g of 3-oxo-3,4-dihydro-2-pyrazinecarboximidamide. The reaction mixture thus obtained was united with the reaction mixture obtained above, and the product was purified by reversed phase silica gel column chromatography [eluent: acetonitrile:water=1:4] to obtain 0.34 g of (2R,3R,4R,5R)-4-(acetyloxy)-2-[(acetyloxy)methyl]-5-[3-[amino(imino) methyl]-2-oxo-1(2H)-pyrazinyl]tetrahydro-3-furanyl acetate as a light yellow-colored solid product.

IR(KBr) cm$^{-1}$: 3392, 1750, 1685

$^1$H-NMR (CDCl$_3$) δ: 2.11(3H,s), 2.16(6H,s), 4.4–4.7(3H, m), 5.31(1H,t,J=5.0 Hz), 5.5–5.6(1H,m), 6.22(1H,d,J=3.0 Hz), 7.8–8.0(1H,m), 8.1–8.3(1H,m), 8.67(1H,brs), 10.45 (2H,brs)

EXAMPLE I-15

To 5.0 mL of 25% aqueous solution of ammonia was added 0.10 g of (2R,3R,4R,5R)-4-(acetyloxy)-2-[(acetyloxy)methyl]-5-[3-[amino(imino)methyl]-2oxo-1 (2H)-pyrazinyl]tetrahydro-3-furanyl acetate at an ice-cooled temperature, and the mixture thus formed was stirred at the same temperature as above for 2 hours. After adding 4.9 mL of acetic acid to the reaction mixture, the solvent was removed under reduced pressure. Further, the same reaction as above was repeated by using 20 mg of (2R,3R,4R,5R)-4-(acetyloxy)-2-[(acetyloxy)methyl]-5-[3-[amino(imino) methyl]-2-oxo1(2H)-pyrazinyl]tetrahydro-3-furanyl acetate, and the reaction mixture thus obtained was united with the reaction mixture obtained above. The united mixture was purified by reversed phase silica gel column chromatography [eluent: water]. To the solid product thus obtained was added 5.0 mL of 1 mol/L hydrochloric acid, and the solvent was removed under reduced pressure. Further, 5.0 mL of 1 mol/L hydrochloric acid was added and the solvent was removed under reduced pressure. Ethanol was added to the residue thus obtained, and the solid product was collected by filtration to obtain 30 mg of 4-[(2R,3R,4S,5R)-3,4-dihydroxy-5-(hydroxymethyl)tetrahydro-2-furanyl]-3-oxo-3,4-dihydro-2-pyrazinecarboximidamide hydrochloride as a light yellow-colored solid product.

IR (KBr) cm$^{-1}$: 3374, 3281, 1690

$^1$H-NMR (DMSO-d$_6$) δ: 3.7–3.9(2H,m), 3.9–4.2(3H,m), 5.1–5.3(1H,m), 5.3–5.6(1H,m), 5.6–5.8(1H,m), 5.90(1H,s), 7.86(1H,d,J=4.0 Hz), 8.76(1H,d,J=4.0 Hz), 9.44(3H,brs)

EXAMPLE I-16

In 2.0 mL of trimethyl phosphate was suspended 0.11 g of 4-[(2R,3R,4S,5R)-3,4-dihydroxy-5-(hydroxymethyl) tetrahydro-2-furanyl]-3-oxo-3,4-dihydro-2-pyrazinecarboxamide. At an ice-cooled temperature, 0.11 mL of phosphorus oxychloride was added, and stirred at the same temperature as above for 2 hours. Then, a solution of 1.2 mL of tributylamine and 0.56 g of tributylammonium phosphate in 6.0 mL of dimethylformamide was added to the reaction mixture and stirred at the same temperature as above for one hour. Then, a 0.1 mol/L solution of triethylammonium hydrogen carbonate was added to the reaction mixture, and the mixture was allowed to stand at room temperature for 12 hours. The solvent was removed under reduced pressure, and the residue thus obtained was purified by ion exchange column chromatography to obtain a fraction containing triethylamine salt of {(2R,3S,4R,5R)-5-[3-(aminocarbonyl)-2-oxo-1(2H)-pyrazinyl]-3,4-dihydroxytetrahydro-2-furanyl}methyl diphosphate and a fraction containing a triethylamine salt of {(2R,3S,4R,5R)-5-[3-(aminocarbonyl)-5-fluoro-2-oxo-1(2H)-pyrazinyl]-3, 4-dihydroxytetrahydro-2-furanyl}methyl triphosphate, from which 143 mg of a solid product were obtained, respectively.

Of the 143 mg of triethylamine salt of {(2R,3S,4R,5R)-5-[3-(aminocarbonyl)-2-oxo-1(2H)-pyrazinyl]-3,4-dihydroxytetrahydro-2-furanyl}methyl diphosphate, a 110 mg portion was taken out and dissolved in 3.0 mL of methanol, to which was added a solution of 0.28 g of sodium perchlorate in 7.5 mL of acetone. The solid product was collected by centrifugation, and washed with acetone to obtain 64 mg of sodium salt of {(2R,3S,4R,5R)-5-[3-(aminocarbonyl)-2-oxo1(2H)-pyrazinyl]-3,4-dihydroxytetrahydro-2-furanyl}methyl diphosphate as a white-colored solid product.

IR (KBr) cm$^{-1}$: 3418, 1682, 1236, 983, 905

$^1$H-NMR (D$_2$O) δ: 4.2–4.5(5H,m), 6.12(1H,s), 7.83(1H, d,J=3.7 Hz), 8.35(1H,d,J=3.7 Hz)

EXAMPLE I-17

Of the 113 mg of triethylamine salt of {(2R,3S,4R,5R)-5-[3-(aminocarbonyl)-2-oxo-1(2H)-pyrazinyl]-3,4-dihydroxytetrahydro-2-furanyl}methyl triphosphate obtained in Example I-16, a 46 mg portion was taken out and dissolved in 1.0 mL of methanol, to which was added a solution of 92 mg of sodium perchlorate in 5.0 mL of acetone. The solid product was collected by centrifugation and washed with acetone to obtain 21 mg of a sodium salt of {(2R,3S,4R,5R)-5-[3-(aminocarbonyl)-2-oxo-1(2H)-pyrazinyl]-3,4-dihydroxytetraydro-2-furanyl}methyl triphosphate.

IR (KBr) cm$^{-1}$: 3436, 1692, 1284, 1103, 997

$^1$H-NMR (D$_2$O) δ: 4.2–4.5(5H,m), 6.14(1H,s), 7.85(1H, d,J=3.0 Hz), 8.36(1H,d,J=3.0 Hz)

EXAMPLE I-18

Under a stream of nitrogen gas, 5.3 g of 6-fluoro-3-hydroxy-2-pyrazinecarboxamide was suspended in 53 ml of acetonitrile. Then, 8.4 mL of N,O-bis(trimethylsilyl)acetamide was added at an ice-cooled temperature, and the mixture thus obtained was stirred at room temperature for 1.5 hours. While cooling the reaction mixture with ice, a solution of 9.4 g of (2R,3R,4R)-4,5-bis(acetyloxy)-2-(hydroxymethyl)tetrahydro-3-furanyl acetate prepared elsewhere according to the procedure mentioned in Carbohydr. Res., Vol. 203, No. 9, Pages 324–329 (1990) in 53 mL of acetonitrile and 7.2 mL of stannic (IV) chloride were successively added to the reaction mixture, and the mixture thus obtained was stirred at room temperature for 20 minutes. The reaction mixture was poured into a mixture of 100 mL of ethyl acetate and 300 mL of saturated aqueous solution of sodium hydrogen carbonate, the organic layer was separated, and the aqueous layer was extracted with 700 mL ethyl acetate. All the organic layers were united and dried on anhydrous magnesium sulfate, and 20 the solvent was removed reduced pressure. The residue was dissolved in 200 mL of methanol, 100 mL of 80% aqueous solution of acetic acid was added, and the mixture thus obtained was stirred at room temperature for 2 hours. The solvent was removed under reduced pressure, the residue was purified by silica gel column chromatography [eluent: chloroform:methanol= 40:1], chloroform and isopropyl ether were added, and the solid product was collected by filtration to obtain 9.3 g of (2R,3R,4R,5R)-4-(acetyloxy)-2-[3-(aminocarbonyl)-5-fluoro-2-oxo-1(2H)-pyrazinyl]-5-(hydroxymethyl)tetranydro-3-furanyl acetate as a light yellow-colored solid product.

IR (KBr) cm$^{-1}$: 3411, 1752, 1686

$^1$H-NMR (DMSO-d$_6$) δ: 2.04(3H,s), 2.10(3H,s), 3.64(1H, ddd,J=2.5,5.0,13 Hz), 3.86(1H,ddd,J=2.5,5.0,13 Hz), 4.29 (1H,d,J=6.0 Hz), 5.35(1H,t,J=6.0 Hz), 5.49(1H,dd,J=3.0,5.0 Hz), 5.65(1H,t,J=5.0 Hz), 6.11(1H,d,J=3.0 Hz), 7.96(1H, brs), 8.42(1H,d,J=5.0 Hz), 8.49(1H,brs)

EXAMPLE I-19

Under a stream of nitrogen gas, 1.5 g of (2R,3R,4R,5R)-4-(acetyloxy)-2-[3-(aminocarbonyl)-5-fluoro-2-oxo-1(2H)-pyrazinyl] -5-(hydroxymethyl)tetrahydro-3-furanyl acetate and 0.84 g of 1H-tetrazole in 30 mL of acetonitrile. While cooling the solution with ice, a solution of 1.4 ml of diallyl diisopropyl phosphoramidite in 20 mL of acetonitrile was added and stirred for 20 minutes. Then, a solution of 1.4 g of m-chloroperbenzoic acid in 10 mL of acetonitrile was added to the reaction mixture, and stirred for 10 minutes. Then, 60 mL of ethyl acetate was added into the reaction mixture, the reaction mixture thus obtained was poured into 60 ml of water, the organic layer was separated, and the aqueous layer was extracted with 90 mL of ethyl acetate. All the organic layers were united, 30 ml of water was added, pH was adjusted to 8 with a saturated aqueous solution of sodium hydrogen carbonate, and the aqueous layer was rejected. The organic layer was washed with saturated aqueous solution of sodium chloride and dried on anhydrous magnesium sulfate, and the solvent was removed under reduced pressure. The residue was purified by silica gel column chromatography [eluent: chloroform:methanol= 40:1] to obtain 1.3 g of (2R,3R,4R,5R)-4-(acetyloxy)-2-[3-(aminocarbonyl)-5-fluoro-2-oxo1(2H)-pyrazinyl]-5-({[bis (allyloxy)phosphoryl]oxy}methyl)tetrahydro-3-furanyl acetate as a yellow-colored solid product.

IR (KBr) cm$^{-1}$: 3403, 1753, 1694, 1244, 1024

$^1$H-NMR (CDCl$_3$) δ: 2.11(3H,s), 2.15(3H,s), 4.32–4.35 (1H,m), 4.47–4.52(2H,m), 4.58–4.64(4H,m), 5.27(2H,dt,J= 1.0,10.5 Hz), 5.37–5.44(4H,m), 5.90–6.00(2H,m), 6.28(1H, d,J=4.0 Hz), 6.32(1H,brs), 7.99(1H,d,J=6.0 Hz), 9.02(1H, brs)

EXAMPLE I-20

In 4.0 mL of methanol was dissolved 0.23 g of (2R,3R, 4R,SR)-4-(acetyloxy)-2-[3-(aminocarbonyl)-5-fluoro-2-oxo-1(2H)-pyrazinyl]-5-({[bis(allyloxy)-phosphoryl] oxy}methyl)tetrahydro-3-furanyl acetate. While cooling the solution with ice, 0.17 g of 28% methanol solution of sodium methoxide was added, and stirred for 5 minutes. Then, 0.15 mL of acetic acid was added, and the solvent was removed under reduced pressure. On the other hand, 1.0 g of (2R,3R,4R,5R)-4-(acetyloxy)-2-[3-(aminocarbonyl)-5-fluoro-2-oxo1(2H)-pyrazinyl]-5-({[bis(allyloxy) phosphoryl]oxy}methyl)tetrahydro-3-furanyl acetate was reacted in the same manner as above. Both the reaction mixtures were united and purified by silica gel column chromatography [eluent: chloroform:methanol=40:1]. Thus, 0.35 g of {(2R,3S,4R,5R)-5-[3-(aminocarbonyl)-5-fluoro-2-oxo-1(2H)-pyrazinyl]-3,4-dihydroxytetrahydro-2-furanyl}methyl diallyl phosphate was obtained as a yellow-colored solid product.

IR (KBr) cm$^{-1}$: 3417, 1684, 1264, 1025, 1000

$^1$H-NMR (DMSO-d$_6$,D$_2$O) δ: 3.1–4.7(10H,m), 5.1–5.5 (4H,m), 5.7–6.2(2H,m), 7.94(1H,d,J=6.0 Hz)

EXAMPLE I-21

In a mixture of 8.2 mL of methanol and 8.2 mL of tetrahydrofuran was dissolved 0.82 g of {(2R,3S,4R,5R)-5-[3-(aminocarbonyl)-5-fluoro-2-oxo-1(2H)-pyrazinyl]-3,4-dihydroxytetrahydro-2-furanyl}methyl diallyl phosphate under a stream of nitrogen gas. After adding 0.11 g of tetrakis-triphenylphosphine palladium (0) and 0.28 g of triphenylphosphine successively, the mixture thus obtained was stirred at room temperature for 30 minutes. While cooling the reaction mixture with ice, a solution of 0.68 mL of formic acid in 1.9 mL of tetrahydrofuran and a solution of 0.25 mL of n-butylamine in 8.2 mL of tetrahydrofuran were successively added. The mixture thus obtained was stirred at 30–35° C. for one hour and then at 40–45° C. for 2 hours. The reaction mixture was diluted with 10 mL of water, and the organic solvent was removed under reduced pressure. The aqueous solution thus obtained was washed with 20 mL of chloroform, and the washings were extracted with 30 mL of water. All the aqueous layers were united, and the solvent was removed under reduced pressure. The residue thus obtained was purified by reversed phase silica gel column chromatography [eluent: water]. Thus, 0.29 g of {(2R,3S,4R,5R)-5-[3-(aminocarbonyl)-5-fluoro-2-oxo-1(2H)-pyrazinyl]-3,4-dihydroxytetrahydro-2-furanyl}methyl dihydrogen phosphate n-butylamine salt was obtained as a yellow-colored solid product.

IR (KBr) cm$^{-1}$: 3382, 1685, 1183, 1110

$^1$H-NMR (DMSO-d$_6$) δ: 0.75–0.90(3H,m), 1.25–1.40 (2H,m), 1.45–1.70(2H,m), 2.70–2.80(2H,m), 3.3–4.7(9H, m), 5.33(1H,d,J=10 Hz), 5.42(1H,d,J=17 Hz), 5.90(2H,brs), 7.95(1H,brs), 8.34(1H,d,J=5.0 Hz), 8.63(1H,brs)

EXAMPLE I-22

In a mixture of 4.2 mL of acetonitrile and 8.4 mL of N,N-dimethylformamide was suspended 0.21 g of {(2R,3S,4R,5R)-5-[3-(aminocarbonyl)-5-fluoro-2-oxo-1(2H)-pyrazinyl]-3,4-dihydroxytetrahydro-2-furanyl}methyl dihydrogen phosphate n-butylamine salt. Then, 0.15 g of N,N-carbonyldiimidazole was added and stirred at room temperature for 2 hours. Then, 19 μL of methanol was added to the reaction mixture and stirred for 30 minutes. Then, a solution of 0.86 g of tri-n-butylammonium pyrophosphate in 2.0 mL of N,N-dimethylformamide was added and stirred for an additional 14 hours. The solvent was removed under reduced pressure, and the residue thus obtained was purified by ion exchange column chromatography [eluent: 0.10 mol/L solution of triethylammonium hydrogen carbonate] and by reversed phase column chromatography [eluent: water], successively. To the solid product thus obtained were added 0.90 mL of methanol and a solution of 0.17 g of sodium perchlorate in 4.5 mL of acetone, successively. The precipitate was collected by centrifugation and then washed with acetone to obtain 60 mg of sodium salt of {(2R,3S,4R,5R)-5-[3-(aminocarbonyl)-5-fluoro-2-oxo-1(2H)-pyrazinyl]-3,4-dihydroxytetrahydro-2-furanyl]methyl triphosphate as a light yellow-colored solid product.

IR (KBr) cm$^{-1}$: 3422, 1686, 1252, 1108

$^1$H-NMR (D$_2$O) δ: 4.3–4.5(5H,m), 6.09(1H,s), 8.41(1H, d,J=5.1 Hz)

EXAMPLE I-23

(2R,3R,4R)-5-(acetyloxy)-2-[(benzoyloxy)methyl]-4-fluorotetrahydro-3-furanyl benzoate prepared according to WO93/10137 was treated in the same manner as in Example I-1 to obtain (2R,3R,4R,5R)-5-[3-(aminocarbonyl)-2-oxo-1 (2H)-pyrazinyl]2-[(benzyloxy)methyl]-4-fluorotetrahydro-3-furanyl benzoate.

R (KBr) cm$^{-1}$: 3422, 1718, 1685

H-NMR (CDCl$_3$) δ: 4.1–6.2(6H,m), 7.3–8.2(12H,m), 8.1–8.3(1H,m), 8.8–9.1(2H,m)

EXAMPLE I-24

(2R,3R,4R,5R)-5-[3-(aminocarbonyl)-2-oxo-1(2H)-pyrazinyl]2-[(benzyloxy)methyl]-4-fluorotetrahydro-3-furanyl benzoate was treated in the same manner as in Example I-6 to obtain 4-[(2R ,3R,4R,5R)-3-fluoro-4-hydroxy-5-(hydroxymethyl)tetrahydro-2-furanyl]-3-oxo-3,4-dihydro-2-pyrazinecarboxamide.

R (KBr) cm$^{-1}$: 3376, 1684, 1654

H-NMR (CDCl$_3$,CD$_3$OD) δ: 3.7–4.4(4H,m), 4.96(1H,dd, J=4.0,52 Hz), 6.22(1H,d,J=16 Hz), 7.76(1H,d,J=4.0 Hz), 8.42(1H,d,J=4.0 Hz)

REFERENTIAL EXAMPLE II-1

In a mixture of 14 mL of 12 mol/L hydrochloric acid and 14 mL of tetrahydrofuran was suspended 8.0 g of methyl 3-amino-6-chloro-2-pyrazinecarboxylate. After adding 5.9 g of sodium nitrite at 5–12° C., the mixture thus obtained was stirred at an ice-cooled temperature for 50 minutes. Then, 8.4 g of cuprous (I) chloride suspended in 6 mol/L hydrochloric acid was added and stirred at the same temperature as above for 10 minutes. The reaction mixture was poured into a mixture of 100 mL of ethyl acetate and 100 mL of water, and the organic layer was separated. The organic layer thus obtained was washed successively with 50 mL of water and 50 mL of saturated aqueous solution of sodium chloride and dried on anhydrous magnesium sulfate, and the solvent was removed under reduced pressure. The residue was purified by silica gel chromatography [eluent: n-hexane:ethyl acetate=6:1] to obtain 6.0 g of methyl 3,6-dichloro-2-pyrazinecarboxylate as a colorless oily product.

R (neat) cm$^{-1}$: 1747

H-NMR (CDCl$_3$) δ: 4.04(3H,s), 8.54(1H,s)

REFERENTIAL EXAMPLE II-2

In 10 mL of methanol was dissolved 2.0 g of methyl 3,6-dichloro-2-pyrazinecarboxylate. Then, 10.2 mL of 1 mol/L aqueous solution of sodium hydroxide was added at an ice-cooled temperature and stirred at room temperature for one hour. The reaction mixture was poured into a mixture of 200 mL of ethyl acetate and 200 mL of water, and the organic layer was separated. The organic layer was washed successively with 50 mL of water and 50 mL of saturated aqueous solution of sodium chloride and dried on anhydrous magnesium sulfate, and the solvent was removed under reduced pressure. The residue thus obtained was washed with hexane to obtain 1.6 g of 3,6-dichloro-2-pyrazinecarboxylic acid as a white-colored solid product.

R (KBr) cm$^{-1}$: 1718

H-NMR (DMSO-d$_6$) δ: 2.50(1H,s), 8.84(1H,s)

REFERENTIAL EXAMPLE II-3

Into 1.2 L of 97% sulfuric acid was added and dissolved 208.0 g of 3-hydroxy-2-pyrazinecarboxamide, while keeping the solution at 10–25° C. by cooling it with ice. To the solution thus obtained was added 185.0 g of potassium nitrate at 30–35° C., and the mixture thus obtained was stirred at room temperature for 15 hours and then at 40° C. for 2 hours. After cooling the reaction mixture to 20° C., it was poured into 6 L of ice water and stirred at room temperature for one hour, and the deposited matter was collected by filtration and washed with two 500 mL portions of water. The solid product thus obtained was suspended in 1 L of water, pH was adjusted to 1.5 with 5 mol/L aqueous solution of sodium hydroxide, and then the solid matter was collected by filtration. The solid was washed successively with 500 mL of water and 500 mL of acetone to obtain 180.0 g of 3-hydroxy-6-nitro-2-pyrazinecarboxamide as a solid product.

R (KBr) cm$^{-1}$: 1707, 1685, 1654

H-NMR (DMSO-d$_6$) δ: 5.60(1H,brs), 8.10(1H,brs), 8.35 (1H,brs), 8.96(1H,s)

REFERENTIAL EXAMPLE II-4

To 400 mL of phosphorus oxychloride was added 88.7 g of 3-hydroxy-6-nitro-2-pyrazinecarboxamide at 55–60° C. After reacting the mixture at the same temperature as above for 15 minutes, 150 mL of pyridine was dropwise added thereto at 40–60° C. The reaction mixture was stirred first at 60° C. for one hour, then at 80° C. for one hour and finally at 100° C. for 4 hours, mixed with 600 mL of toluene, and then returned to room temperature. After filtering off the deposited precipitate, the filtrate was concentrated to dryness under reduced pressure. To the residue thus obtained were added 500 mL of toluene and 1 L of water successively, the mixture thus obtained was stirred at 40° C. for 30 minutes, and the organic layer was separated. The organic layer was washed first with two 500 mL portions of water and then with one 200 mL portion of saturated aqueous solution of sodium chloride and dried on anhydrous magnesium sulfate, and the solvent was removed under reduced pressure. The residue thus obtained was purified by silica gel chromatography [eluent: n-hexane:toluene=1:1] to obtain 64.5 g of 3,6-dichloro-2-pyrazinecanbonitrile as a solid product.

R (KBr) cm$^{-1}$: 2236, 2252

H-NMR (CDCl$_3$) δ: 8.60(1H,s)

REFERENTIAL EXAMPLE II-5

In 1.19 L of water were dissolved 80.0 g of 3-hydroxy-6-nitro-2-pyrazinecarboxamide and 47.5 g of sodium hydroxide. After heating under reflux for 1.5 hours, 400 mL of ethanol was added at 40° C. and stirred for 30 minutes, and then 400 mL of ethanol was added at 30° C. and stirred for 30 minutes. After adding 400 mL of ethanol additionally at 20° C., the mixture was cooled to 10° C. and the deposited matter was collected by filtration. The collected matter was washed with 160 mL of ethanol and dried at 40° C. for 15 hours to obtain 78.8 g of a solid product. The solid product (78.5 g) was suspended in 1.5 L of methanol, into which dry hydrogen chloride gas was introduced for one hour until saturation. The mixture was heated under reflux for one hour and cooled, the deposited salt was filtered off, and the filtrate was concentrated to dryness under reduced pressure. Ethanol (500 mL) was added to the residue and concentrated to dryness under reduced pressure, and the residue was washed with 250 mL of isopropyl alcohol to obtain 48.8 g of methyl 6-nitro-3-oxo-3,4-dihydro-2-pyrazinecarboxylate as a solid product.

R (KBr) cm$^{-1}$: 1736

$^1$H-NMR (CDCl$_3$) δ: 2.45(1H,brs), 3.87(3H,s), 8.98(1H, s)

REFERENTIAL EXAMPLE II-6

In 2.0 L of dioxane was suspended 48.7 g of methyl 6-nitro-3-oxo-3,4-dihydro-2-pyrazinecarboxylate, to which were successively added 42.4 mL of N-ethyldiisopropylamine and 9.9 mL of methanol. Then, 122 mL of a 2.0 mol/L solution of trimethylsilyldiazomethane in hexane was added at room temperature, the mixture thus obtained was stirred at the same temperature as above for 15 hours, and the solvent was removed under reduced pressure. Then, 500 mL of ethyl acetate and 250 mL of water were added to the residue obtained above, pH was adjusted to 1.5 with 6 mol/L hydrochloric acid, and the organic layer was separated. The remaining aqueous layer was extracted with two 200 mL portions of ethyl acetate. All the organic layers were united, washed successively with 200 ml of water and 200 mL of saturated aqueous solution of sodium chloride and dried on anhydrous magnesium sulfate, and the solvent was removed under reduced pressure. The residue thus obtained was purified by silica gel chromatography ]eluent: n-hexane:ethyl acetate=2:1] to obtain 24.3 g of methyl 3-methoxy-6-nitro-2-pyrazinecarboxylate as a solid product.

R (KBr) cm$^{-1}$: 1729

H-NMR (DMSO-d$_6$) δ: 4.03(3H,s), 4.22(3H,s), 9.25(1H, s)

REFERENTIAL EXAMPLE II-7

At room temperature and under a pressure of 1 atmosphere, hydrogen gas was introduced into a mixture of 24.3 g of methyl 3-methoxy-6-nitro-2-pyrazinecarboxylate, 480 mL of acetic acid and 1.2 g of lead-poisoned palladium-calcium carbonate until the mixture became showing no further absorption of hydrogen. After filtering off insoluble matter from the reaction mixture, the solvent was removed under reduced pressure, and the solid product thus obtained was washed with ethyl acetate and diethyl ether. Thus, 15.0 g of methyl 6-amino-3-metoxy-2-pyrazinecarboxylate was obtained as a solid product. Furthermore, the solvent was removed from the filtrate under reduced pressure to obtain a solid product, and the solid product was washed with ethyl acetate to obtain 2.3 g of methyl 6-amino-3-methoxy-2-pyrazinecarboxylate as a solid product.

R (KBr) cm$^{-1}$: 1717

H-NMR (CDCl$_3$) δ: 3.97(3H,s), 3.99(3H,s), 4.38(2H,brs), 7.79(1H,s)

REFERENTIAL EXAMPLE II-8

In 80 mL of tetrahydrofuran was dissolved 4.0 g of 3-amino-6-bromo-2-pyrazinecarbonitrile synthesized according to the procedure mentioned in U.S. Pat. No. 3,341,540. While cooling the solution with ice, 1.2 g of 60% sodium hydride and 2.8 mL of benzoyl chloride were successively added, and further 0.8 g of 60% sodium hydride was added. The mixture thus obtained was stirred at an ice-cooled temperature for one hour and thereafter at room temperature for 30 minutes. Then, 0.4 g of 60% sodium hydride was added additionally, and the mixture thus formed was stirred at room temperature for 30 minutes. After cooling the reaction mixture with ice, the mixture was poured into a liquid mixture consisting of 50 mL of ethyl acetate and 100 mL of water, and pH was adjusted to 5 with 6 mol/L hydrochloric acid. The deposited matter was collected by filtration, and the residue thus obtained was dissolved in a mixture of 50 mL of ethyl acetate and 100 mL of tetrahydrofuran, treated with active charcoal, and filtered, after which the solvent was removed under reduced pressure. The residue thus obtained was washed with diisopropyl ether to obtain 1.7 g of N-(5-bromo-3-cyano-2-pyrazinyl)-benzamide as a light yellow-colored solid product. Furthermore, organic layer was separated from the filtrate obtained above, and organic layer was washed successively with water and saturated aqueous solution of sodium chloride, treated with active charcoal and dried on anhydrous magnesium sulfate, and the solvent was removed under reduced pressure. The residue thus obtained was washed with diisopropyl ether to obtain 2.9 g of N-(5-bromo-3-cyano-2-pyrazinyl)-benzamide as a yellow-colored solid product.

R (KBr) cm$^{-1}$: 2238, 1667

H-NMR (CDCl$_3$) δ: 7.41–7.64(3H,m), 8.04–8.15(2H,m), 8.76(1H,s), 11.31(1H,brs)

REFERENTIAL EXAMPLE II-9

In 10 mL of tetrahydrofuran was dissolved 0.50 g of 3-amino-6-bromo-2-pyrazinecarbonitrile. After adding 0.15 g of 60% sodium hydride, the mixture was stirred at room temperature for 15 minutes. Then, 0.7 mL of di-t-butyl dicarbonate and 0.10 g of 60% sodium hydride were successively added, and the mixture thus formed was stirred at room temperature for one hour. The reaction mixture was added to a liquid mixture consisting of 30 mL of ethyl acetate and 60 mL of water, pH was adjusted to 5 with 2 mol/L hydrochloric acid, and the organic layer was separated. The organic layer was washed successively with water and saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=5:1] to obtain 0.30 g of t-butyl 5-bromo-3-cyano-2-pyrazinylcarbamate as a white-colored solid product.

IR(KBr) cm$^{-1}$: 2239, 1708

$^1$H-NMR (CDCl$_3$+DMSO-d$_6$) δ: 1.57(9H,s), 7.41(1H, brs), 8.62(1 H,s)

REFERENTIAL EXAMPLE II-10

In 10 mL of dimethylformamide was dissolved 1.0 g of 3,6-dichloro-2-pyrazinecarbonitrile. After adding 0.7 g of hydroquinone and 1.74 g of potassium carbonate, the mixture thus obtained was stirred at room temperature for 30 minutes. The reaction mixture was poured into a mixture of 10 mL of ethyl acetate and 30 mL of water, pH was adjusted to 7 with 2 mol/L hydrochloric acid, and the organic layer was separated. The organic layer thus obtained was washed successively with water and saturated aqueous solution of sodium chloride and dried on anhydrous magnesium sulfate, and the solvent was removed under reduced pressure. The residue was purified by silica gel column chromatography [eluent: n-hexane:ethyl acetate=3:1] to obtain 1.0 g of 6-chloro-3-(4-hydroxyphenoxy)-2-pyrazinecarbonitrile as a yellow-colored solid product.

R (KBr) cm$^{-1}$: 3384, 2250

H-NMR (CDCl$_3$) δ: 6.82–7.05(4H,m), 8.27(1H,s), 8.88 (1H,s)

REFERENTIAL EXAMPLE II-11

In 15 ml of dimethylformamide was dissolved 1.5 g of 3,6-dichloro-2-pyrazinecarbonitrile. After adding 1.2 g of 4-methoxyphenol and 1.8 g of potassium carbonate, the mixture thus obtained was stirred at room temperature for 30 minutes. A mixture of 20 mL of ethyl acetate and 60 mL of water was added to the reaction mixture, and the organic layer was separated. The organic layer was washed successively with water and saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=5:1] to obtain 2.1 g of 6-chloro-3-(4-methoxyphenoxy)-2-pyrazinecarbonitrile as a yellow-colored solid product.

R (KBr) cm$^{-1}$: 2236

H-NMR (CDCl$_3$) δ: 3.83(3H,s), 6.95(2H,d,J=9.2 Hz), 7.11(2H,d,J=9.2 Hz), 8.26(1H,s)

REFERENTIAL EXAMPLE II-12

In 25 mL of dimethylformamide was dissolved 2.5 g of 3,6-dichloro-2-pyrazinecarbonitrile. After adding 3.2 g of 4-(benzyloxy)phenol and 3.0 g of potassium carbonate, the mixture was stirred at room temperature for one hour. A mixture of 25 ml of ethyl acetate and 100 mL of water was added to the reaction mixture, and the organic layer was separated. The organic layer thus obtained was washed successively with water and saturated aqueous solution of sodium chloride and dried on anhydrous magnesium sulfate, and the solvent was removed under reduced pressure. Diisopropyl ether was added to the residue, the insoluble matter was filtered off, and the filtrate was concentrated. The residue thus obtained was washed with n-hexane to obtain 3.84 g of 3-[(4-(benzyloxy)phenoxy)]-6-chloro-2-pyrazinecarbonitrile as a light brown-colored solid product.

R (KBr) cm$^{-1}$: 2238

H-NMR (CDCl$_3$) δ: 5.12(2H,s), 7.03–7.48(9H,m), 8.65 (1H,s)

REFERENTIAL EXAMPLE II-13

In 8 mL of dimethylformamide was dissolved 0.4 g of 6-chloro-3-(4-hydroxyphenoxy)-2-pyrazinecarbonitrile. After adding 0.5 ml of iodomethane and 0.89 g of potassium carbonate, the mixture thus obtained was stirred at room temperature for 30 minutes. The reaction mixture was added to a mixture of 10 mL of ethyl acetate and 30 mL of water, and the organic layer was separated. The organic layer was washed successively with water and saturated aqueous solution of sodium chloride and dried on anhydrous magnesium sulfate, and the solvent was removed under reduced pressure. Thus, 0.43 g of 6-chloro-3-(4-methoxyphenoxy)-2-pyrazinecarbonitrile was obtained as a yellow-brown colored solid product.

R (KBr) cm$^{-1}$: 2236

H-NMR (CDCl$_3$) δ: 3.83(3H,s), 6.95(2H,d,J=9.2 Hz), 7.11(2H,d,J=9.2 Hz), 8.26(1H,s)

REFERENTIAL EXAMPLE II-14

In 5 mL of dimethylformamide dimethyl acetal was dissolved 1.0 g of 3-amino-6-bromo-2-pyrazinecarbonitrile. The solution was heated under reflux for 3 hours. The reaction mixture was returned to room temperature, and a mixture of 5 mL of n-hexane and 5 mL of diisopropyl ether was added and stirred at room temperature for 10 minutes. The deposited precipitate was collected by filtration and washed with a mixture of 5 mL of n-hexane and 5 mL of diisopropyl ether to obtain 1.0 g of N'-(5-bromo-3-cyano-2-pyrazinyl)-N,N-dimethyliminoformamide as a yellow-brown-colored solid product.

R (KBr) cm$^{-1}$: 2234

H-NMR (CDCl$_3$) δ: 3.21(6H,s), 8.32(1H,s), 8.60(1H,s)

REFERENTIAL EXAMPLE II-15

In 50 mL of N,N-dimethylformamide was dissolved 10.0 g of 3,6-dichloro-2-pyrazinecarbonitrile. After adding 6.49 mL of thiophenol and 11.91 g of potassium carbonate successively, the mixture thus obtained was stirred at 40° C.

for 3 hours. The reaction mixture was poured into a mixture of 100 mL of ethyl acetate and 100 mL of water, and pH was adjusted to 2 with 6 mol/L hydrochloric acid. The organic layer was separated, washed successively with water and saturated aqueous solution of sodium chloride, and dried on anhydrous magnesium sulfate, and then the solvent was removed under reduced pressure. The residue thus obtained was purified by silica gel column chromatography [eluent: toluene:n-hexane=1:3] to obtain 3.80 g of 6-chloro-3-(phenylsulfanyl)-2-pyrazinecarbonitrile as a light yellow-colored oily product.

R (neat) $cm^{-1}$: 2238

H-NMR (CDCl$_3$) δ: 7.00–7.70(5H,m), 8.39(1H,s)

EXAMPLE II-1

(a) In 20 mL of acetonitrile was dissolved 2.0 g of methyl 3,6-dichloro-2-pyrazinecarboxylate. After adding 2.8 g of potassium fluoride and 0.51 g of 18-crown-6-ether, the mixture thus obtained was heated under reflux for 9.5 hours in an atmosphere of nitrogen gas. After cooling, the solvent was removed under reduced pressure, and the residue was purified by silica gel chromatography [eluent: n-hexane:ethyl acetate=15:1] to obtain 1.1 g of methyl 3,6-difluoro-2-pyrazinecarboxylate as a colorless oily product.
R (neat) $cm^{-1}$: 1743
H-NMR (CDCl$_3$) δ: 4.05(3H,s), 8.28(1H,dd,J=1.6 Hz, 8.4 Hz)
(b) In 2.0 mL of methylene chloride was suspended 0.2 g of 3,6-dichloro-2-pyrazinecarboxylic acid. Then, 0.001 mL of N,N-dimethylformamide and 0.14 mL of oxalyl chloride were successively added at an ice-cooled temperature, and the mixture thus formed was stirred at room temperature for 40 minutes. The reaction mixture was concentrated to dryness under reduced pressure and then dissolved in 3.0 mL of acetonitrile. Then, 0.3 g of potassium fluoride and 0.056 g of 18-crown-6-ether were added and the mixture thus formed was stirred at 60° C. for 2.5 hours in an atmosphere of nitrogen gas. The reaction mixture was poured into 3.0 mL of methanol, the insoluble matter was filtered off, and then the filtrate was concentrated to dryness under reduced pressure. The residue was purified by silica gel chromatography [eluent: n-hexane:ethyl acetate-9:1] to obtain 0.15 g of methyl 3,6-difluoro-2-pyrazinecarboxylate as a colorless oily product.
Physical properties of this compound coincided with those of the compound obtained in Example II-1(a).

EXAMPLE II-2

In 3.0 mL of N,N-dimethylformamide was dissolved 0.3 g of methyl 3,6-difluoro-2-pyrazinecarboxylate. After adding 0.16 g of sodium acetate at an ice-cooled temperature, the mixture thus obtained was stirred at 50° C. for 2.5 hours. The reaction mixture was poured into a mixture of 50 mL of ethyl acetate and 30 mL of water, and the organic layer was separated. The remaining aqueous phase was extracted with three 25 mL portions of ethyl acetate. The organic layers were united, washed successively with 15 mL of water and 15 ml of saturated aqueous solution of sodium chloride and dried on anhydrous magnesium sulfate, and the solvent was removed under reduced pressure. The residue was purified by silica gel chromatography [eluent: n-hexane:ethyl acetate=1:2] to obtain 0.03 g of methyl 6-fluoro-3-oxo-3,4-dihydro-2-pyrazinecarboxylate as a colorless solid product.

R KBr $cm^{-1}$: 1677
H-NMR (CDCl$_3$) δ: 4.09(3H,s), 8.35(1H,d,J=8.3 Hz), 11.1(1H,brs)

EXAMPLE II-3

(a) In 1.1 L of dimethyl sulfoxide was suspended 90.1 g of 3,6-dichloro-2-pyrazinecarbonitrile. After adding 180.5 g of potassium fluoride and 66.8 g of tetra-n-butylammonium bromide, the mixture was stirred at 50–55° C. for 6 hours. The reaction mixture was returned to room temperature and added to a mixture of 1.1 L of ethyl acetate and 2.2 L of water, and the organic layer was separated. Water (1 L) was added to the organic layer, pH was adjusted to 2.5 with 1 mol/L hydrochloric acid, and the organic layer was separated. The organic layer was washed with saturated aqueous solution of sodium chloride and dried on anhydrous magnesium sulfate, and the solvent was removed under reduced pressure. The residue was purified by silica gel chromatography [eluent: n-hexane:ethyl acetate=10:1] to obtain 58.3 g of 3,6-difluoro-2-pyrazinecarbonitrile as a colorless solid product.
R (KBr) $cm^{-1}$: 2250
H-NMR (CDCl$_3$) δ: 8.34(1H,dd,J=1.3, 7.9 Hz)
(b) In 4 mL of dimethyl sulfoxide was dissolved 0.40 g of 6-fluoro-3-(phenylsulfonyl)-2-pyrazinecarbonitrile. After adding 0.44 g of potassium fluoride and 0.10 g of tetra-n-butylammonium bromide successively, the mixture thus obtained was stirred at 60° C. for 1.5 hours. The reaction mixture was poured into a mixture of 20 mL of ethyl acetate and 20 mL of water, and the organic layer was separated. The organic layer was washed successively with water and saturated aqueous solution of sodium chloride and dried on anhydrous magnesium sulfate, and the solvent was removed under reduced pressure. The residue was purified by silica gel column chromatography [eluent: n-hexane:ethyl acetate=20:1] to obtain 0.06 g of 3,6-difluoro-2-pyrazinecarbonitrile as a colorless solid product.

EXAMPLE II-4

In a mixture of 570 mL of 12 mol/L hydrochloric acid and 57 mL of tetrahydrofuran was suspended 57.3 g of 3,6-difluoro-2-pyrazinecarbonitrile. The suspension was stirred at 30–35° C. for 6.5 hours. The reaction mixture was concentrated to dryness under reduced pressure, 100 mL of ethanol was added, and then the solvent and hydrochloric acid were removed under reduced pressure. The residue thus obtained was washed with ethanol and diisopropyl ether to obtain 53.7 g of 3,6-difluoro-2-pyrazinecarboxamide as a colorless solid product.
R (KBr) $cm^{-1}$: 1708, 1692
H-NMR (DMSO-d$_6$) δ: 8.00(1H,brs), 8.25(1H,brs), 8.57 (1H,dd,J=1.7, 8.1 Hz)

EXAMPLE II-5

(a) In 10 mL of N,N-dimethylformamide was dissolved 1.0 g of 3,6-difluoro-2-pyrazinecarbonitrile. At an ice-cooled temperature, 0.64 g of sodium acetate was added and stirred for 6 hours. The reaction mixture was added to a mixture of 20 mL of ethyl acetate and 20 mL of water, pH was adjusted to 1.5 with 6 mol/L hydrochloric acid, and the organic layer was separated. The organic layer was washed with saturated aqueous solution of sodium chloride and dried on anhydrous magnesium sulfate, and the solvent was removed under reduced pressure. The residue thus obtained was purified by silica gel chromatography [eluent: n-hexane:ethyl acetate-: 1:1] to obtain 0.45 g of 6-fluoro-3-oxo-3,4-dihydro-2-pyrazinecarbonitrile as a yellow-colored solid product.

R (KBr) cm$^{-1}$: 2238, 1655

H-NMR (DMSO-d$_6$) δ: 8.52(1H,d,J=7.6 Hz), 12.70(1H, brs)

(b) In 10 mL of toluene was dissolved 1.0 g of 3-(benzyloxy)-6-fluoro-2-pyrazinecarbonitrile. Then, 0.64 g of aluminum chloride was added to the solution at an ice-cooled temperature, and the mixture thus formed was stirred at room temperature for 2 hours. Then, 10 mL of water was added to the reaction mixture, the aqueous layer was separated, and the organic layer was extracted with two 2 mL portions of water. The aqueous layers were united and extracted with two 5 mL portions of ethyl acetate. The organic layer thus obtained was washed with saturated aqueous solution of sodium chloride and dried on anhydrous magnesium sulfate, and the solvent was removed under reduced pressure. Thus, 0.51 g of 6-fluoro-3-oxo-3,4-dihydro-2-pyrazinecarbonitrile was obtained as a yellow-colored solid product.

Physical properties of this compound coincided with those of the compound obtained in Example II-5(a).

(c) In 5 mL of toluene was dissolved 1.0 g of 3-(allyloxy)-6-fluoro-2-pyrazinecarbonitrile. After adding 0.82 g of aluminum chloride, the mixture was stirred at room temperature for 1.5 hours. Water (5 mL) was added to the reaction mixture, the aqueous layer was separated, and the organic layer was extracted first with 3 mL of water and then with 2 ml of water. The aqueous layers were united and washed with 5 mL of toluene, and extracted with 15 mL of ethyl acetate. The organic layer thus obtained was washed with 3 mL of water and dried on anhydrous magnesium sulfate, and the solvent was removed under reduced pressure. Thus, 0.45 g of 6-fluoro-3-oxo-3,4-dihydro-2-pyrazinecarbonitrile was obtained as a yellow-colored solid product.

Physical properties of this compound coincided with those of the compound obtained in Example II-5(a).

(d) In a mixture of 30 mL of acetonitrile and 20 mL of water was dissolved 1.0 g of 6-fluoro-3-(4-methoxyphenoxy)-2-pyrazinecarbonitrile. After adding 11.2 g of diammonium cerium nitrate, the mixture was heated under reflux for 3 hours. The reaction mixture was returned to room temperature, a mixture consisting of 50 mL of toluene, 50 mL of water and 10 mL of 5% aqueous solution of sodium thiosulfate was added to the reaction mixture, and the aqueous layer was separated. Ethyl acetate (50 mL) was added to the aqueous layer thus obtained, and the organic layer was separated. The organic layer thus obtained was washed with saturated aqueous solution of sodium chloride, treated with active charcoal, and dried on anhydrous magnesium sulfate, and the solvent was removed under reduced pressure. Thus, 6-fluoro-3-oxo-3,4-dihydro-2-pyrazinecarbonitrile was obtained as a yellow-colored solid product.

(e) In a mixture of 30 mL of acetonitrile and 15 mL of water was dissolved 1.0 g of 3-[4-(benzyloxy)phenoxy]-6-fluoro-2-pyrazinecarbonitrile. After adding 8.5 g of diammonium cerium nitrate, the mixture thus obtained was heated under reflux for 3 hours. The reaction mixture was returned to room temperature, a mixture consisting of 50 mL of ethyl acetate, 5 ml of water and 5 mL of 5% aqueous solution of sodium thiosulfate was added, and the organic layer was separated. The organic layer thus obtained was washed with saturated aqueous solution of sodium chloride, treated with active charcoal and dried on anhydrous magnesium sulfate, and then the solvent was removed under reduced pressure. Thus, 6-fluoro-3-oxo-3,4-dihydro-2-pyrazinecarbonitrile was obtained as a yellow-colored solid product.

(f) In a mixture of 7.5 mL of acetonitrile and 3 mL of water was dissolved 0.45 g of 6-fluoro-3-(4-hydroxyphenoxy)-2-pyrazinecarbonitrile. Then, 1.17 g of diammonium cerium nitrate was added at room temperature, and stirred at the same temperature as above for 15 minutes. A mixture of 10 mL of ethyl acetate and 5 ml of 5% aqueous solution of sodium thiosulfate was added to the reaction mixture, and the organic layer was separated. The organic layer thus obtained was washed with saturated aqueous solution of sodium chloride, treated with active charcoal and dried on anhydrous magnesium sulfate, and then the solvent was removed under reduced pressure. Thus, 6-fluoro-3-oxo-3,4-dihydro-2-pyrazinecarbonitrile was obtained as a yellow-colored solid product.

(g) In a mixture of 5 ml of 6 mol/L hydrochloric acid and 1 ml of dioxane was suspended 0.5 g of 6-fluoro-3-[(2-methyl-3-oxo-1-cyclopenten-1-yl)oxy]-2-pyrazinecarbonitrile. The suspension was stirred at 50° C. for 15 minutes. The reaction mixture was returned to room temperature, 10 mL of ethyl acetate was added, and the organic layer was separated. The organic layer thus obtained was washed with saturated aqueous solution of sodium chloride and dried on anhydrous magnesium sulfate, and the solvent was removed under reduced pressure. Thus, 0.25 g of 6-fluoro-3-oxo-3,4-dihydro-2-pyrazinecarbonitrile was obtained as a yellow-colored solid product.

Physical properties of this compound coincided with those of the compound obtained in Example II-5(a).

EXAMPLE II-6

In 2.0 mL of N,N-dimethylformamide was dissolved 0.20 g of 3,6-difluoro-2-pyrazinecarbonitrile. At 5° C., 0.11 g of sodium azide was added and stirred at the same temperature as above for 10 minutes. The reaction mixture was added to a mixture of 20 mL of ether and 20 mL of water, and the organic layer was separated. The organic layer thus obtained was washed successively with 20 mL of water and 20 mL of saturated aqueous solution of sodium chloride and dried on anhydrous magnesium sulfate, and the solvent was removed under reduced pressure. Thus, 0.25 g of 3-azido-6-fluoro-2-pyrazinecarbonitrile was obtained as a yellow-colored oily product.

R (neat) cm$^{-1}$: 2140

H-NMR (CDCl$_3$) δ: 8.40(1H,d,J=8.2 Hz)

EXAMPLE II-7

(a) In a mixture of 1.5 mL of 25% aqueous ammonia and 500 mL of dioxane was dissolved 1.0 g of 3,6-difluoro-2-pyrazinecarbonitrile. The solution thus obtained was stirred at room temperature for 6 hours. Then, 20 mL of water was added to the reaction mixture and stirred for 20 minutes while cooling the mixture with ice. The deposited material was collected by filtration, washed successively with 5 mL of cold water and 5 mL of ethanol to obtain 0.84 g of 3-amino-6-fluoro-2-pyrazine-carbonitrile as a light yellow-colored solid product.

R (KBr) cm$^{-1}$: 3405, 2230

H-NMR (DMSO-d$_6$) δ: 7.34(2H,brs), 8.42(1H,d,J=7.8 Hz)

(b) In 5.0 mL of methanol was dissolved 0.24 g of 3-azido-6-fluoro-2-pyrazinecarbonitrile. After adding 0.075 g of lead-poisoned palladium-calcium carbonate at room temperature, hydrogen gas was introduced into the mixture at room temperature under a pressure of 1 atmosphere until the mixture became showing no further adsorption of hydrogen. After filtering off the insoluble matter from the reaction mixture, the filtrate was concentrated under reduced pressure. The residue thus obtained was purified by silica gel column chromatography [eluent: chloroform] to obtain 0.078 g of 3-amino-6-fluoro-2-pyrazinecarbonitrile as a yellow-colored solid product.

Physical properties of this compound coincided with those of the compound obtained in Example II-7(a).

(c) In 10.5 mL of dimethyl sulfoxide was dissolved 0.35 g of t-butyl 5-bromo-3-cyano-2-pyrazinylcarbamate. After adding 0.17 g of potassium fluoride, the mixture was stirred first at 70° C. for 30 minutes and then at 90° C. for 30 minutes to form t-butyl 3-cyano-5-fluoro-2-pyrazinylcarbamate in the reaction system. Then, 0.17 g of potassium fluoride was added and stirred at 90° C. for 40 minutes. The reaction mixture was returned to room temperature and added to a mixture of 30 ml of ethyl acetate and 60 mL of water, pH was adjusted to 8 with saturated aqueous solution of sodium hydrogen carbonate, and the organic layer was separated. The organic layer thus obtained was washed with saturated aqueous solution of sodium chloride and dried on anhydrous sodium sulfate, and the solvent was removed under reduced pressure. The residue thus obtained was purified by silica gel column chromatography [eluent: n-hexane:ethyl acetate=3:1] to obtain 20 mg of 3-amino-6-fluoro-2-pyrazinecarbonitrile as a yellow-colored solid product.

Physical properties of this compound coincided with those of the compound obtained in Example II-7(a).

(d) In 2 mL of 6 mol/L hydrochloric acid was suspended 60 mg of N'-(3-cyano-5-fluoro-2-pyrazinyl)-N,N-dimethyliminoformamide. The suspension thus formed was stirred at 80–90° C. for 5.5 hours. The reaction mixture was returned to room temperature, 5 mL of water was added, and pH was adjusted to 9 with 2 mol/L aqueous solution of sodium hydroxide. Then, 5 mL of ethyl acetate was added, the organic layer was separated, washed with saturated aqueous solution of sodium chloride and dried on anhydrous sodium sulfate, and the solvent was removed under reduced pressure. Thus, 20 mg of 3-amino-6-fluoro-2-pyrazinecarbonitrile was obtained as a yellow-colored solid product.

(e) In 15 mL of acetonitrile was dissolved 0.3 g of 3-amino-2-pyrazinecarbonitrile. While cooling the solution with ice, 10% fluorine gas (a fluorine gas diluted with nitrogen gas) was introduced into the solution at a rate of 45 mL per minute for a period of 20 minutes. Then, while elevating the temperature from the ice-cooled temperature to room temperature, nitrogen gas was introduced for one hour. The reaction mixture was concentrated under reduced pressure, and the oily product thus obtained was purified by silica gel column chromatography [eluent: n-hexane:ethyl acetate=3:1] to obtain 0.01 g of 3-amino-6-fluoro-2-pyrazinecarbonitrile as a yellow-colored solid product.

EXAMPLE II-8

(a) In 140 mL of 70% solution of hydrogen fluoride in pyridine was dissolved 17.3 g of methyl 6-amino-3-methoxy-2-pyrazinecarboxylate at an ice-cooled temperature. Then, 7.8 g of sodium nitrite was added at −50° C. in three portions. After the foaming had ceased, the temperature was slowly elevated, and the mixture was stirred at room temperature for 30 minutes. The reaction mixture was poured into a mixture of 300 mL of ice and 200 mL of chloroform, the deposited insoluble matter was filtered off, and then the organic layer was separated. The remaining aqueous layer was extracted with ten portions of chloroform, provided that the total quantity of liquid came to 500 mL. The organic layers thus obtained were united, pH was adjusted to 7 with a saturated aqueous solution of sodium hydrogen carbonate, and the organic layer was separated. The organic layer thus obtained was washed with saturated aqueous solution of sodium chloride and dried on anhydrous magnesium sulfate, and the solvent was removed under reduced pressure. The residue thus obtained was purified by silica gel chromatography [eluent: n-hexane:ethyl acetate=4:1] to obtain 14.3 g of methyl 6-fluoro-3-methoxy-2-pyrazinecarboxylate as a solid product.

R (KBr) cm$^{-1}$: 1734

H-NMR (CDCl$_3$) δ: 3.98(3H,s), 4.08(3H,s), 8.17(1H,d,J=8.5 Hz)

(b) In 4 mL of methanol was dissolved 0.2 g of methyl 3,6-difluoro-2-pyrazinecarboxylate. Then, a 28% methanol solution of sodium methoxide was added at −25° C., and the mixture thus obtained was stirred at 0° C. for 10 minutes. The reaction mixture was poured into a mixture of 30 mL of ethyl acetate and 30 mL of water, and the organic layer was separated. The organic layer thus obtained was washed successively with 15 ml of water and 15 mL of saturated aqueous solution of sodium chloride and dried on anhydrous magnesium sulfate, and the solvent was removed under reduced pressure. The residue thus obtained was purified by silica gel chromatography [eluent: n-hexane:ethyl acetate=5:1] to obtain 0.09 g of methyl 6-fluoro-3-methoxy-2-pyrazinecarboxylate as a colorless solid product.

Physical properties of this compound coincided with those of the compound obtained in Example II-8(a).

EXAMPLE II-9

In 2.0 mL of acetonitrile was dissolved 0.1 g of methyl 6-chloro-3-nitro-2-pyrazinecarboxylate. After adding 40 mg of potassium fluoride and 61 mg of 18-crown-6-ether successively, the mixture thus obtained was stirred at room temperature for 1.5 hours. Then, a mixture of 10 mL of ethyl acetate and 10 mL of water was added, pH was adjusted to 7.0 with saturated aqueous solution of sodium hydrogen carbonate, and the organic layer was separated. The organic layer thus obtained was washed with saturated aqueous solution of sodium chloride and dried on anhydrous magnesium sulfate, and the solvent was removed under reduced pressure. The residue thus obtained was purified by silica gel chromatography [eluent: n-hexane:ethyl acetate=7:1] to obtain 0.03 g of methyl 6-fluoro-3-nitro-2-pyrazinecarboxylate as a light yellow-colored oily product.

R (KBr) cm$^{-1}$: 1752, 1560

H-NMR (CDCl$_3$) δ: 4.06(3H,s), 8.50(1H,d,J=8.3 Hz)

EXAMPLE II-10

(a) In 1.0 mL of acetic acid was dissolved 20 mg of methyl 6-fluoro-3-nitro-2-pyrazinecarboxylate. After adding 6 mg of lead-poisoned palladium-calcium carbonate, hydrogen gas was introduced into the mixture at room temperature under a pressure of 1 atmosphere, until the mixture became absorbing no further quantity of hydrogen gas. The insoluble matter was filtered off from the reaction mixture, and the filtrate was concentrated under reduced pressure. The residue thus obtained was purified by silica gel column chromatography [eluent: n-hexane:ethyl acetate=5:1] to obtain 2 mg of methyl 3-amino-6-fluoro-2-pyrazinecarboxylate as a light yellow-colored solid product.

R (KBr) cm$^{-1}$: 1700

H-NMR (CDCl$_3$) δ: 3.98(3H,s), 6.29(2H,brs), 8.1 5(1H, d,J=8.3 Hz)

(b) In 10 mL of acetic acid was dissolved 0.5 g of methyl 3-amino-2-pyrazinecarboxylate. At room temperature, 10% fluorine gas (a fluorine gas diluted with nitrogen gas) was introduced into the solution at a rate of 23 mL per minute for a period of 32 minutes. After stirring the solution for 30 minutes at room temperature, the reaction mixture was added to a mixture of 50 mL of saturated aqueous solution of sodium hydrogen carbonate and 50 mL of ethyl acetate, and the organic layer was separated. The organic layer thus obtained was washed successively with 10 mL of water and 10 mL of saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=3:1] to obtain 0.01 g of methyl 3-amino-6-fluoro-2-pyrazinecarboxylate as a light yellow-colored solid product.

Physical properties of this compound coincided with those of the compound obtained in Example II-10(a).

EXAMPLE II-11

(a) In 1 mL of methanol was dissolved 10 mg of methyl 3-amino-6-fluoro-2-pyrazinecarboxylate. After adding 1 mL of 25% aqueous ammonia at room temperature, the mixture thus formed was stirred for 4.5 hours. After removing the solvent under reduced pressure, diethyl ether was added to the residue, and the deposited precipitate was filtered off. Thus, 4 mg of 3-amino-6-fluoro-2-pyrazinecarboxamide was obtained as a light yellow-colored solid product.

R (KBr) cm$^{-1}$: 1685

H-NMR (CDCl$_3$+CD$_3$OD) δ: 3.85(4H,brs), 8.10(1H,d,J= 7.3 Hz)

(b) In 2.0 mL of methylene chloride was suspended 0.2 g of 3,6-dichloro-2-pyrazinecarboxylic acid. Then, 0.001 mL of N,N-dimethylformamide and 0.14 mL of oxalyl chloride were successively added at an ice-cooled temperature, and the mixture thus formed was stirred at room temperature for one hour. The reaction mixture was concentrated to dryness under reduced pressure, the residue was dissolved in 3.0 mL of acetonitrile, 0.35 g of potassium fluoride and 0.054 g of 18-crown-6-ether were added, and the mixture thus obtained was stirred at 60° C. for 3 hours. Then, 3.0 mL of 25% aqueous ammonia was added to the reaction mixture at room temperature, and the mixture thus obtained was stirred at 50° C. for 2.5 hours. The reaction mixture was poured into a mixture of 30 mL of ethyl acetate and 30 mL of water, and the organic layer was separated. The organic layer thus obtained was washed successively with 15 ml of water and 15 ml of saturated aqueous solution of sodium chloride and dried on anhydrous magnesium sulfate, and the solvent was removed under reduced pressure. The deposited product was washed with diethyl ether, and there was obtained 0.12 g of 3-amino-6-fluoro-2-pyrazinecarboxamide as a yellow-colored solid product.

Physical properties of this compound coincided with those of the compound obtained in Example II-11(a).

(c) In 9 mL of trifluoroacetic acid was dissolved 0.3 g of 3-amino-2-pyrazinecarboxamide. At an ice-cooled temperature, 10% fluorine gas (a fluorine gas diluted with nitrogen gas) was introduced into the solution at a rate of 45 ml per minute for a period of 22 minutes. After stirring the mixture at an ice-cooled temperature for 17 minutes, the temperature was elevated to room temperature. The reaction mixture was added to a mixture of 30 mL of saturated aqueous solution of sodium hydrogen carbonate and 30 mL of ethyl acetate, and the organic layer was separated. The remaining aqueous layer was acidified with 6 mol/L hydrochloric acid and then extracted with 20 ml of ethyl acetate. The organic layers thus obtained were united, washed successively with 10 mL of water and 10 mL of saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=2:1] to obtain 0.015 g of 3-amino-6-fluoro-2-pyrazinecarboxamide as a light yellow-colored solid product.

Physical properties of this compound coincided with those of the compound obtained in Example II-11(a).

(d) In 5 mL of trifluoroacetic acid was dissolved 100 mg of 3-amino-2-pyrazinecarboxamide. At an ice-cooled temperature, 10% fluorine gas (a fluorine gas diluted with nitrogen gas) was introduced at a rate of 45 mL per minute for a period of 36 minutes. Then, while elevating the temperature from the ice-cooled temperature to room temperature, nitrogen gas was introduced for one hour. The reaction mixture was concentrated under reduced pressure to obtain 305 mg of an oily product. Of the oily product thus obtained, a 251 mg portion was dissolved in 9.3 mL of water and heated under reflux for 4 hours, The liquid reaction mixture was cooled to room temperature, and the deposited precipitate was filtered off. The filtrate was concentrated under reduced pressure, and the solid product thus obtained was purified by silica gel column chromatography [eluent: n-hexane:ethyl acetate=2:1] to obtain 9 mg of 3-amino-6-fluoro-2-pyrazinecarboxamide as a solid product.

Physical properties of this compound coincided with those of the compound obtained in Example II-11(a).

EXAMPLE II-12

In 200 mL of water was suspended 1.0 g of 3-hydroxy-2-pyrazinecarboxamide. At room temperature, 10% fluorine gas (a fluorine gas diluted with nitrogen gas) was introduced at a rate of 45 mL per minute for a period of 25 minutes. Then, nitrogen gas was introduced for 45 minutes, and the liquid reaction mixture was neutralized with calcium carbonate, the deposited precipitate was filtered off, the filtrate was concentrated under reduced pressure, and the solid product thus obtained was purified by silica gel column chromatography [eluent: n-hexane:ethyl acetate=5:1] to obtain 0.008 g of 6-fluoro-3-hydroxy-2-pyrazinecarboxamide as a white-colored solid product.

Physical properties of this compound coincided with those of the compound obtained in Production Example 1.

EXAMPLE II-13

In 5 ml of toluene was dissolved 0.5 g f 3,6-difluoro-2-pyrazinecarbonitrile. After adding 0.41 mL of benzyl alcohol and 0.74 mL of triethylamine successively, the mixture thus obtained was stirred at 80° C. for one hour. The reaction mixture was cooled to room temperature and then purified by silica gel column chromatography [eluent: n-hexane:ethyl acetate=10:1] to obtain 0.58 g of 3-(benzyloxy)-6-fluoro-2-pyrazinecarbonitrile as a white-colored solid product.

R (KBr) cm$^{-1}$: 2236

H-NMR (CDCl$_3$) δ: 5.53(2H,s), 7.3–7.6(5H,m), 8.20(1H, d,J=8.1 Hz)

EXAMPLE II-14

In 30 mL of dimethyl sulfoxide was dissolved 10.0 g of 3,6-difluoro-2-pyrazinecarbonitrile. After adding 50 mL of allyl alcohol and 14.8 mL of triethylamine successively, the mixture thus obtained was stirred at 60° C. for 40 minutes. The reaction mixture was cooled to room temperature and poured into a mixture of 50 mL of toluene and 50 mL of water, and the organic layer was separated. The organic layer thus obtained was washed successively with ten 50 mL portions of water and then with saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=10:1] to obtain 11.5 g of 3-(allyloxy)-6-fluoro-2-pyrazinecarbonitrile as a light yellow-colored oily product.

R (neat) cm$^{-1}$: 2238

$^1$H-NMR (CDCl$_3$) δ: 4.98(2H,d,J=5.6 Hz), 5.33(1H,dd, J=1.5,7.1 Hz), 5.48(1H,dd,J=1.5,13.9 Hz), 5.9–6.2(1H,m), 8.20(1H,d,J=8.1 Hz)

EXAMPLE II-15

In 25 mL of methanol was dissolved 2.5 g of 3,6-difluoro-2-pyrazinecarbonitrile. Then, 2.4 g of 28% methanolic solution of sodium methoxide was dropwise added at 5–15° C., and the mixture thus formed was stirred at an ice-cooled temperature for 2 hours. The reaction mixture was poured into a mixture of 50 mL of ethyl acetate and 50 mL of water, and the organic layer was separated. The organic layer thus obtained was washed successively with water and saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=10:1] to obtain 0.45 g of 6-fluoro-3-methoxy-2-pyrazinecarbonitrile as a colorless oily product.

IR (neat) cm$^{-1}$: 2237

$^1$H-NMR (CDCl$_3$) δ: 4.12(3H,s), 8.22(1H,d,J=8.1 Hz)

EXAMPLE II-16

In a mixture of 140 ml of acetonitrile and 280 ml of toluene were suspended 58 g of potassium fluoride (spray-dried) and 8.7 g f 18-crown-6-ether. After heating the suspension under reflux for one hour in an atmosphere of nitrogen gas, the acetonitrile and toluene were distilled off under atmospheric pressure. The residue thus obtained was suspended in 280 mL of acetonitrile, 23 g of 6-chloro-2-pyrazinecarbonitrile synthesized according to the method described in Acta Poloniae Pharmaceutica, Vol. 33, Pages 153–161 (1976) was added, and the mixture thus obtained was heated under reflux for one hour in an atmosphere of nitrogen. The reaction mixture was cooled to room temperature, 280 mL of ethyl acetate and 280 mL of water were added, and the organic layer was separated. The organic layer thus obtained was washed successively with water and saturated aqueous solution of sodium chloride and dried on anhydrous magnesium sulfate, and the solvent was distilled off under a reduce pressure. The residue was purified by silica gel column chromatography [eluent: n-hexane:ethyl acetate=10:1] to obtain 10 g of 6-fluoro-2-pyrazinecarbonitrile as a white-colored solid product.

IR (KBr) cm$^{-1}$: 2244

$^1$H-NMR (CDCl$_3$) δ: 8.72(1H,d,J=8.1 Hz), 8.88(1H,d, J=3.7 Hz)

EXAMPLE II-17

In 10 mL of concentrated hydrochloric acid was dissolved 1.6 g of 6-fluoro-2-pyrazinecarbonitrile. The solution thus obtained was stirred at 40° C. for 2 hours. The reaction mixture was cooled to room temperature, a mixture of 25 mL of ethyl acetate and 10 mL of water was added, and the organic layer was separated. The aqueous layer was extracted with ethyl acetate. The organic layers were united, washed with saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=1:1] to obtain 0.75 g of 6-fluoro-2-pyrazinecarboxamide as a light brown-colored solid product.

IR (KBr) cm$^{-1}$: 1713

$^1$H-NMR (DMSO-d$_6$) δ: 7.90(1H,brs), 8.22(1H,brs), 8.92 (1H,d,J=8.0), 9.14(1H,d,J=4.4)

EXAMPLE II-18

(a) In 1.5 mL of trifluoroacetic acid was dissolved 0.50 g of 6-fluoro-2-pyrazinecarboxamide. After adding 0.40 mL of 30% hydrogen peroxide, the mixture thus obtained was stirred at 50–60° C. for one hour. After cooling the reaction mixture to 5° C., 5 mL of isopropyl alcohol was added. The deposited product was collected by filtration and washed with 5 ml of isopropyl alcohol and 5 mL of diethyl ether to obtain 0.35 g of3-(aminocarbonyl)-5-fluoropyrazin-1-ium-1-olate as a white-colored solid product.

IR (KBr) cm$^{-1}$: 1708

$^1$H-NMR (DMSO-d$_6$) δ: 8.03(1H,brs), 8.25(1H,brs), 8.53 (1H,brs), 8.70(1H,dd,J=1.2,3.9 Hz)

(b) In 1.95 mL of phosphorus oxychloride was suspended 0.39 g of 3-(aminocarbonyl)-5-fluoropyrazin-1-ium-1-olate. The mixture was stirred at 100° C. for 1.5 hours. After concentrating the reaction mixture to dryness under reduced pressure, the residue was suspended in 20 mL of ethyl acetate and poured into 20 mL of ice water, and the organic layer was separated. To the organic layer thus obtained was added 20 mL of water, after which pH was adjusted to 8 with saturated aqueous solution of sodium hydrogen carbonate, the organic layer was separated and dried on anhydrous magnesium sulfate, and the solvent was removed under reduced pressure. The residue thus obtained was purified by silica gel column chromatography [eluent: toluene:n-hexane=3:1] to obtain 3-chloro-6-fluoro-2-pyrazinecarbonitrile as an oily product.

(c) In 15 mL of acetonitrile was dissolved 0.3 g of 3-chloro-2-pyrazinecarbonitrile. At an ice-cooled temperature, 10% fluorine gas (a fluorine gas diluted with nitrogen gas)

was introduced into the solution at a rate of 45 mL per minute for a period of 20 minutes. Then, while elevating the temperature from the ice-cooled temperature to room temperature, nitrogen gas was introduced over a period of one hour. The reaction mixture was concentrated under reduced pressure and the oily product thus obtained was purified by silica gel column chromatography [eluent: n-hexane:ethyl acetate=10:1] to obtain 0.12 g of 3-chloro-6-fluoro-2-pyrazinecarbonitrile as a colorless oily product.

IR (KBr) cm$^{-1}$: 2232

$^1$H-NMR (CDCl$_3$) δ: 8.50(1H,d,J=8.1 Hz)

EXAMPLE II-19

In 26 mL of dimethyl sulfoxide was dissolved 1.30 g of N'-(5-bromo-3-cyano-2-pyrazinyl)-N,N-dimethyliminoformamide. After adding 2.97 g of potassium fluoride, the mixture thus obtained was stirred for 1.5 hours at 145–150° C. The reaction mixture was returned to room temperature, a mixture of 30 mL of ethyl acetate and 100 mL of water was added, and the organic layer was separated. The organic layer thus obtained was washed with saturated aqueous solution of sodium chloride and dried on anhydrous sodium sulfate, and the solvent was removed under reduced pressure. The residue thus obtained was purified by silica gel column chromatography [eluent: toluene:ethyl acetate=5:1] to obtain 0.75 g of N'-(3-cyano-5-fluoro-2-pyrazinyl)-N,N-dimethyliminoformamide as a yellow-colored solid product.

IR (KBr) cm$^{-1}$: 2230

$^1$H-NMR (CDCl$_3$) δ: 3.19(6H,s), 8.18(1H,d,J=8.1 Hz), 8.54(1H,s)

EXAMPLE II-20

In 86 mL of dimethyl sulfoxide was dissolved 4.3 g of N-(5-bromo-3-cyano-2-pyrazinyl)benzamide. After adding 8.3 g of potassium fluoride, the mixture thus obtained was stirred at 110–115° C. for one hour. The reaction mixture was returned to room temperature, a mixture of 100 mL of ethyl acetate and 200 mL of water was added, and the organic layer was separated. The organic layer thus obtained was washed successively with water and saturated aqueous solution of sodium chloride, treated with active charcoal and dried on anhydrous magnesium sulfate, and the solvent was removed under reduced pressure. The residue thus obtained was purified by silica gel column chromatography [eluent: toluene:ethyl acetate=5:1] to obtain 0.47 g of N-(3-cyano-5-fluoro-2-pyrazinyl)benzamide as a white-colored solid product.

IR (KBr) cm$^{-1}$: 2238, 1670

$^1$H-NMR (CDCl$_3$) δ: 7.48–7.80(3H,m), 8.03–8.21(2H, m), 9.01(1H,d,J=8.1 Hz), 11.67(1H,s)

EXAMPLE II-21

In 39 mL of dimethyl sulfoxide was dissolved 1.95 g of 6-chloro-3-(4-methoxyphenoxy)-2-pyrazinecarbonitrile. After adding 2.16 g of potassium fluoride, the mixture thus obtained was stirred at 100–110° C. for 3 hours. The reaction mixture was returned to room temperature, a mixture of 40 mL of ethyl acetate and 200 mL of water was added, and the organic layer was separated. The organic layer thus obtained was washed with saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=5:1] to obtain 1.45 g of 6-fluoro-3-(4-methoxyphenoxy)-2-pyrazinecarbonitrile as a yellow-colored solid product.

IR (KBr) cm$^{-1}$: 2238

$^1$H-NMR (CDCl$_3$) δ: 3.83(3H,s), 6.95(2H,d,J=9.2 Hz), 7.12(2H,d,J=9.2 Hz), 8.15(1H,d,J=8.4 Hz)

EXAMPLE II-22

In 70 ml of dimethyl sulfoxide was dissolved 3.50 g of 3-[4-(benzyloxy)phenoxy]-6-chloro-2-pyrazinecarbonitrile. After adding 3.01 g of potassium fluoride, the mixture was stirred at 100–110° C. for 3 hours. The reaction mixture was returned to room temperature and added to a mixture of 70 mL of ethyl acetate and 350 mL of water, and the organic layer was separated. The organic layer thus obtained was washed with saturated aqueous solution of sodium chloride and dried on anhydrous magnesium sulfate, and the solvent was removed under reduced pressure. The residue thus obtained was purified by silica gel column chromatography [eluent: toluene:ethyl acetate=5:1] to obtain 1.88 g of 3-[4-(benzyloxy)phenoxy]-6-fluoro-2-pyrazinecarbonitrile as a white-colored solid product.

IR (KBr) cm$^{-1}$: 2237

$^1$H-NMR (CDCl$_3$) δ: 5.07(2H,s), 6.95–7.40(9H,m), 8.13 (1H,d,J=8.1 Hz)

EXAMPLE II-23

In 15 mL of acetonitrile was dissolved 0.3 g of methyl 3-chloro-2-pyrazinecarboxylate. At an ice-cooled temperature, 10% fluorine gas (a fluorine gas diluted with nitrogen gas) was introduced at a rate of 45 ml per minute for a period of 18 minutes. Then, while elevating the temperature from the ice-cooled temperature to room temperature, nitrogen gas was introduced for one hour, and the reaction product was concentrated under reduced pressure. The oily product thus obtained was purified by silica gel column chromatography (eluent: n-hexane:ethyl acetate=10:1] to obtain 0.03 g of methyl 3-chloro-6-fluoro-2-pyrazinecarboxylate as a colorless oily product.

IR (neat) cm$^{-1}$: 1736

$^1$H-NMR (CDCl$_3$) δ: 4.04(3H,s), 8.43(1H,d,J=8.3 Hz)

EXAMPLE II-24

In 30 mL of dimethylformamide was dissolved 3.0 g of 3,6-difluoro-2-pyrazinecarbonitrile. Then, 2.6 g of hydroquinone, followed by 6.5 g of potassium carbonate, was added at an ice-cooled temperature, and the mixture thus obtained was stirred at room temperature for 15 minutes. A mixture of 30 mL of ethyl acetate and 60 ml of water was added to the reaction mixture, pH was adjusted to 5 with 6 mol/L hydrochloric acid, and the organic layer was separated. The organic layer thus obtained was washed successively with water and saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=3:1] to obtain 0.75 g of 6-fluoro-3-(4-hydroxyphenoxy)-2-pyrazinecarbonitrile as a yellow-colored solid product.

IR (KBr) cm$^{-1}$: 3398, 2237

$^1$H-NMR (DMSO-d$_6$) δ: 6.82(2H,d,J=9.2 Hz), 7.05(2H,d, J=9.2 Hz), 7.40(1H,s), 8.68(1H,d,J=8.1 Hz)

EXAMPLE II-25

In 3.6 mL of dimethyl sulfoxide was dissolved 0.20 g of 6-chloro-3-(phenylsulfanyl)-2-pyrazinecarbonitrile. After adding 0.42 g of potassium fluoride and 0.16 g of tetra-n-butylammonium bromide successively, the mixture thus obtained was stirred at 50–60° C. for 2.5 hours. The reaction mixture was poured into a mixture of 20 mL of ethyl acetate and 20 mL of water, and the organic layer was separated. The organic layer was washed successively with water and saturated aqueous solution of sodium chloride and dried on anhydrous magnesium sulfate, and the solvent was removed under reduced pressure. The residue thus obtained was purified by silica gel column chromatography [eluent: toluene:n-hexane=1:2] to obtain 0.10 g of 6-fluoro-3-(phenylsulfanyl)-2-pyrazinecarbonitrile as a light yellow-colored oily product.

IR (neat) cm$^{-1}$: 2233

$^1$H-NMR (CDCl$_3$) δ: 7.10–7.70(5H,m), 8.34(1H,d,J=8.1 Hz)

EXAMPLE II-26

In 10 mL of methylene chloride was dissolved 1.00 g of 6-fluoro-3-(phenylsulfanyl)-2-pyrazinecarbonitrile. Then, 1.00 g of m-chloroperbenzoic acid was added at an ice-cooled temperature, and the mixture thus obtained was stirred at room temperature for 2 hours. The reaction mixture was poured into a mixture of 20 mL of chloroform and 20 ml of water, pH was adjusted to 10 with potassium carbonate, and the organic layer was separated. The organic layer thus obtained was washed successively with water and saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=2:1] to obtain 0.42 g of 6-fluoro-3-(phenylsulfnyl)-2-pyrazinecarbonitrile as a light yellow-colored oily product.

IR (neat) cm$^{-1}$: 2237

$^1$H-NMR (CDCl$_3$) δ: 7.35–7.75(3H,m), 7.75–8.10(2H, m), 8.68(1H,d,J=8.1 Hz)

EXAMPLE II-27

In 20 mL of methylene chloride was dissolved 1.00 g of 6-fluoro-3-(phenylsulfanyl)-2-pyrazinecarbonitrile. After adding 3.70 g of m-chloroperbenzoic acid at an ice-cooled temperature, the mixture thus obtained was stirred at room temperature for 4 hours. Insoluble matter was filtered off from the reaction mixture, and the filtrate was poured into a mixture of 50 mL of methylene chloride and 50 mL of water, pH was adjusted to 7.5 with a saturated aqueous solution of sodium hydrogen carbonate, and the organic layer was separated. The organic layer thus obtained was washed successively with water and saturated aqueous solution of sodium chloride and dried on anhydrous magnesium sulfate, and the solvent was removed under reduced pressure. Diisopropyl ether was added to the residue thus obtained, and the solid product was collected by filtration to obtain 0.66 g of 6-fluoro-3-(phenylsulfonyl)-2-pyrazinecarbonitrile as a colorless solid product.

IR (KBr) cm$^{-1}$: 2243

$^1$H-NMR (CDCl$_3$) δ: 7.40–7.90(3H,m), 7.95–8.30(2H, m), 8.65(1H,d,J=8.3 Hz)

EXAMPLE II-28

In 5.0 mL of methanesulfonic acid was dissolved 0.50 g of 3-amino-6-fluoro-2-pyrazinecarbonitrile. After adding 0.30 g of sodium nitrite at 7–9° C., the mixture thus formed was stirred at an ice-cooled temperature for 2.0 hours. While keeping the temperature at 10° C. or below, the reaction mixture was dropwise added to a mixture of 15 mL of ice water and 15 ml of ethyl acetate. The mixture thus formed was extracted with two 10 mL portions of ethyl acetate. The organic layer thus obtained was twice washed with saturated aqueous solution of sodium chloride and dried on anhydrous magnesium sulfate, and the solvent was removed under reduced pressure. The residue thus obtained was dissolved in a mixture of 100 mL of n-hexane and 50 mL of ethyl acetate, and the solution thus obtained was three times washed with saturated aqueous solution of sodium hydrogen carbonate and dried on anhydrous magnesium sulfate, and the solvent was removed under reduced pressure. Thus, 0.12 g of 3-cyano-5-fluoro-2-pyrazinylmethanesulfonate was obtained as a colorless oily product.

IR (neat) cm$^{-1}$: 2246

$^1$H-NMR (DMSO-d$_6$) δ: 3.40(3H,s), 8.95(1H,d,J=7.8 Hz)

EXAMPLE II-29

In 60 mL of dimethyl sulfoxide was dissolved 3.0 g of 3,6-dichloro-2-pyrazinecarbonitrile. After adding 3.0 g of potassium fluoride, the mixture thus obtained was stirred at 90–100° C. for 2 hours. The reaction mixture was returned to room temperature, to which were successively added 2.1 g of 2-methyl-1,3-cyclopentandione and 7.2 ml of triethylamine. The mixture thus obtained was stirred at room temperature for one hour. The reaction mixture was added to a mixture of 50 mL of ethyl acetate and 200 mL of water, and the organic layer was separated. The organic layer thus obtained was washed successively with water and saturated aqueous solution of sodium chloride and dried on anhydrous magnesium sulfate, and the solvent was removed under reduced pressure. The residue thus obtained was purified by silica gel column chromatography [eluent: n-hexane:ethyl acetate=2:1] to obtain 1.7 g of 6-fluoro-3-[(2-methyl-3-oxo-1-cyclopenten-1-yl)oxy]-2pyrazinecarbonitrile as a yellow-colored solid product.

IR (KBr) cm$^{-1}$: 2238, 1707, 1676

$^1$H-NMR (CDCl$_3$) δ: 1.72(3H,t,J=1.8 Hz), 2.58–2.68(2H, m), 2.76–2.91(2H,m), 8.29(1H,d,J=8.1 Hz)

PRODUCTION EXAMPLE 1

In 3.0 mL of methanol was dissolved 0.12 g of methyl 6-fluoro-3-oxo-3,4-dihydro-2-pyrazinecarboxylate. Then, gaseous ammonia was introduced into the solution at an ice-cooled temperature for a period of 10 minutes, after which the mixture thus obtained was allowed to stand at room temperature for 2 days. The solvent was removed under reduced pressure, the residue thus obtained was added to a mixture of 30 mL of ethyl acetate and 30 ml of water, pH was adjusted to 7.5 with saturated aqueous solution of sodium hydrogen carbonate, and the organic layer was separated. After adding 30 mL of ethyl acetate to the remaining aqueous layer, pH was adjusted to 1.0 with 1 mol/L hydrochloric acid, and the whole mixture was extracted with two 15 mL portions of ethyl acetate. The organic layers thus obtained were united, washed successively with 15 mL of water and 15 mL of saturated aqueous solution of sodium chloride and dried on anhydrous magnesium sulfate, and the solvent was removed under reduced pressure. The solid product thus obtained was washed with diisopropyl ether to obtain 0.015 g of 6-fluoro-3-hydroxy-2-pyrazinecarboxamide as a yellow-colored solid product.

IR (KBr) cm$^{-1}$: 1685, 1671, 1655

$^1$H-NMR (DMSO-d$_6$) δ: 8.46(1H,brs), 8.50(1H,d,J=7.8 Hz), 8.70(1H,brs), 13.39(1H,s)

PRODUCTION EXAMPLE 2

In a mixture of 3.44 ml of water and 0.5 mL of dioxane was suspended 0.17 g of 3,6-difluoro-2-pyrazinecarboxamide. After adding 0.45 g of sodium hydrogen carbonate, the mixture thus obtained was stirred at 50° C. for 8.5 hours. Then, 0.95 mL of 6 mol/L hydrochloric acid was added to the reaction mixture, pH was adjusted to 1.0, and the deposited solid product was collected by filtration to obtain 89 mg of 6-fluoro-3-hydroxy-2-pyrazinecarboxamide as a solid product.

Physical properties of this compound coincided with those of the compound obtained in Production Example 1.

PRODUCTION EXAMPLE 3

While keeping 285 ml of 97% sulfuric acid at 5–12° C. by cooling it with ice, 28.5 g of 3-amino-6-fluoro-2-pyrazinecarboxamide was added thereto to form a uniform solution. After adding 18.9 g of sodium nitrite to the solution at 5–12° C., the mixture thus obtained was stirred for 1.5 hours while cooling it with ice. While keeping the reaction mixture at a temperature not exceeding 10° C., the reaction mixture was dropwise added to 1.4 L of ice water, and the mixture thus formed was extracted first with one 850 mL portion and then two 200 mL portions of ethyl acetate. The organic layers thus obtained were united, 400 mL of water was added, then 160 mL of saturated aqueous solution of sodium hydrogen carbonate was added, pH was adjusted to 3.0, and the organic layer was separated. The organic layer thus obtained was washed with saturated aqueous solution of sodium chloride and dried on anhydrous magnesium sulfate, and the solvent was removed under reduced pressure. The residue thus obtained was washed with a mixture of diisopropyl ether and ethyl acetate to obtain 22.4 g of 6-fluoro-3-hydroxy-2-pyrazinecarboxamide as a solid product.

Physical properties of this compound coincided with those of the compound obtained in Production Example 1.

PRODUCTION EXAMPLE 4

At a water-cooled temperature, 2.2 g of 6-fluoro-3-oxo-3,4-dihydro-2-pyrazinecarbonitrile was dissolved in an aqueous solution of sodium hydroxide prepared from 1.27 g of sodium hydroxide and 24.2 ml of water. After adding 2.75 ml of 30% hydrogen peroxide at the same temperature as above, the mixture thus formed was stirred at 40° C. for 1.5 hours. After dropwise adding 2.77 mL of concentrated sulfuric acid to the reaction mixture obtained above while cooling it with ice, the mixture thus formed was cooled to 10° C. The deposited crystalline product was collected by filtration and washed with 2 mL of cold water to obtain 2.2 g of 6-fluoro-3-hydroxy-2-pyrazinecarboxamide as a light yellow-colored solid product.

Physical properties of this compound coincided with those of the compound obtained in Production Example 1.

INDUSTRIAL UTILIZABILITY

The pyrazine derivatives or salts thereof of the present invention, namely the compounds of the present invention, have an excellent antiviral activity and are useful as a pharmaceutical drug. Further, the intermediates of the present invention, namely the compounds represented by general formula [21], are useful as an intermediate for production of the pyrazine derivative or salts thereof of the present invention, namely the compounds of the present invention, and as an intermediate for production of known compounds useful as preventive and therapeutic agents for viral infections and especially influenza virus-infections.

What is claimed is:

1. A pyrazine derivative represented by the following formula:

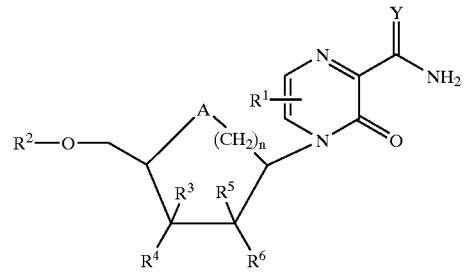

wherein R$^1$ represents a hydrogen atom or a halogen atom; R$^2$ represents a hydrogen atom or a protected or unprotected monophosphoric, diphosphoric or triphosphoric acid group; R$^3$, R$^4$, R$^5$ and R$^6$ which may be the same or different represent a hydrogen atom, a halogen atom, an azido group, a substituted or unsubstituted, protected or unprotected hydroxyl or amino group or R$^4$ and R$^6$, taken conjointly, represent a bond; A represents an oxygen atom or a methylene group; n represents 0 or 1; and Y represents an oxygen atom, a sulfur atom or an NH group, or a salt thereof.

2. A pyrazine derivative or a salt thereof according to claim 1, wherein R$^3$, R$^4$, R$^5$ and R$^6$ which may be the same or different represent a hydrogen atom, a halogen atom, a substituted or unsubstituted, protected or unprotected hydroxyl group, or R$^4$ and R$^6$ are taken conjointly to represent a bond.

3. A pyrazine derivative or a salt thereof according to claim 1, wherein R$^2$ represents a hydrogen atom or a protected or unprotected monophosphoric or triphosphoric acid group.

4. A pyrazine derivative or a salt thereof according to claim 1, wherein R$^2$ represents a hydrogen atom or a protected or unprotected monophosphoric acid group; R$^3$, R$^4$, R$^5$ and R$^6$ which may be the same or different represent a hydrogen atom or a protected or unprotected hydroxyl group; A represents an oxygen atom; and n represents 0.

5. A pyrazine derivative or a salt thereof according to claim 1, wherein R$^2$ is a hydrogen atom.

6. A pyrazine derivative or a salt thereof according to claim 1, wherein Y is an oxygen atom.

7. A pharmaceutical composition comprising a compound or a salt thereof according to claim 1 and at least one of a pharmaceutically acceptable carrier or excipient.

8. The pyrazine derivative or a salt thereof according to claim 1, selected from the group consisting of
4-[(2R,3R,4S,5R)-3, 4-dihydroxy-5-(hydroxymethyl)tetrahydro-2-furanyl]-3-oxo-3,4-dihydro-2-pyrazinecarboxamide,
4-[(4S,5R)-4-hydroxy-5-(hydroxymethyl)tetrahydro-2-furanyl]-3-oxo-3,4-dihydro-2-pyrazinecarboxamide, 4-[(2R,3R,4S,5R)-3,4-dihydroxy-5-(hydroxymethyl)
  tetrahydro-2-furanyl]-6-fluoro-3-oxo-3,4-dihydro-2-
  pyrazinecarboxamide,
6,chloro-4-[(2R,3R,4S,5R)-3,4-dihydroxy-5-
  (hydroxymethyl)tetrahydro-2-furanyl]-3oxo-3,4-dihydro-
  2-pyrazinecarboxamide,
4-[4-(hydroxymethyl)-2-cyclopenten-1-yl]-3-oxo-3,4-
  dihydro-2-pyrazinecarboxamide,
4-[(3S,5S,6R)-5-hydroxy-6-(hydroxymethyl)tetrahydro-
  2H-pyran-3-yl]-3-oxo-3,4-dihydro-2-
  pyrazinecarboxamide,
4-[(3R,4S,5S,6R)-4,5-dihydroxy-6-(hydroxymethyl)
  tetrahydro-2H-pyran-3-yl]-3-oxo-3,4-dihydro-2-
  pyrazinecarboxamide,
{(3aR,4R,6R,6aR)-6-[3-(aminocarbonyl)-2-oxo-1(2H)-
  pyrazinyl]-2,2-dimethyltetrahydrofuro[3,4-d][1,3]
  dioxol-4-yl}methyl dibenzyl phosphate,
{(2R,3S,4R,5R)-5-[3-(aminocarbonyl)-2-oxo-1(2H)-
  pyrazinyl]-3,4-dihydroxytetrahydro-2-furanyl}methyl
  dihydrogen phosphate,
{(2R,3S,4R,5R)-5-[3-(aminocarbonyl)-2-oxo-1(2H)-
  pyrazinyl]-3,4-dihydroxytetrahydro-2-furanyl}methyl
  dibenzyl phosphate,
(2R,3R,4R,5R)-4-(acetyloxy)-2-[(acetyloxy)methyl]-5-[3-
  [amino(imino)methyl]-2-oxo-1(2H)-pyrazinyl]
  tetrahydro-3-furanyl acetate,
4-[(2R,3R,4S,5R)-3,4-dihydroxy-5-(hydroxymethyl)
  tetrahydro-2-furanyl]-3-oxo-3,4-dihydro-2-
  pyrazinecarboximidamide hydrochloride,
{(2R,3S,4R,5R)-5-[3-(aminocarbonyl)-2-oxo-1(2H)-
  pyrazinyl]-3,4-dihydroxytetrahydro-2-furanyl}methyl
  diphosphate,
{(2R,3S,4R,5R)-5-[3-(aminocarbonyl)-2-oxo-1(2H)-
  pyrazinyl]-3,4-dihydroxytetrahydro-2-furanyl}methyl
  triphosphate,
(2R,3R,4R,5R)-4-(acetyloxy)-2-[3-(aminocarbonyl)-5-
  fluoro-2-oxo-1(2H)-pyrazinyl]-5-(hydroxymethyl)
  tetrahydro-3-furanyl acetate,
(2R,3R,4R,5R)-4-(acetyloxy)-2-[3-(aminocarbonyl)-5-
  fluoro-2-oxo-1(2H)-pyrazinyl]-5-({[bis(allyloxy)
  phosphoryl]oxy}methyl)tetrahydro-3-furanyl acetate,
{(2R,3S,4R,5R)-5-[3-(aminocarbonyl)-5-fluoro-2-oxo-1
  (2H)-pyrazinyl]-3,4-dihydroxytetrahydro-2-
  furanyl}methyl diallyl phosphate,
{(2R,3S,4R,5R)-5-[3-(aminocarbonyl)-5-fluoro-2-oxo-1
  (2H)-pyrazinyl]-3,4-dihydroxytetrahydro-2-
  furanyl}methyl dihydrogen phosphate n-butylamine,
{(2R,3S,4R,5R)-5-[3-(aminocarbonyl)-5-fluoro-2-oxo-1
  (2H)-pyrazinyl]-3,4-dihydroxytetrahydro-2-
  furanyl}methyl triphosphate, and
4-[(2R,3R,4R,5R)-3-fluoro-4-hydroxy-5-(hydroxymethyl)
  tetrahydro-2-furanyl]-3-oxo-3,4-dihydro-2-
  pyrazinecarboxamide.

9. The pyrazine derivative or a salt thereof according to claim 1 which is 4-[(2R,3R,4S,5R)-3,4-dihydroxy-5-(hydroxymethyl)
  tetrahydro-2-furanyl]3-oxo-3,4-dihydro-2-
  pyrazinecarboxamide or a salt thereof.

\* \* \* \* \*